(12) United States Patent
Koo et al.

(10) Patent No.: US 11,618,757 B2
(45) Date of Patent: Apr. 4, 2023

(54) POLYCYCLIC COMPOUND AND ORGANIC LIGHT EMITTING ELEMENT COMPRISING SAME

(71) Applicant: LG CHEM, LTD., Seoul (KR)

(72) Inventors: Ki Dong Koo, Daejeon (KR); Ki Kon Lee, Daejeon (KR); Moung Gon Kim, Daejeon (KR); Hyungjin Lee, Daejeon (KR); Dongheon Kim, Daejeon (KR); Kongkyeom Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 464 days.

(21) Appl. No.: 16/642,293

(22) PCT Filed: Oct. 22, 2018

(86) PCT No.: PCT/KR2018/012475
§ 371 (c)(1),
(2) Date: Feb. 26, 2020

(87) PCT Pub. No.: WO2019/078692
PCT Pub. Date: Apr. 25, 2019

(65) Prior Publication Data
US 2020/0181165 A1 Jun. 11, 2020

(30) Foreign Application Priority Data
Oct. 20, 2017 (KR) .................. 10-2017-0136798

(51) Int. Cl.
*H01L 51/00* (2006.01)
*C07D 495/04* (2006.01)
(Continued)

(52) U.S. Cl.
CPC .......... *C07D 495/04* (2013.01); *C07C 211/54* (2013.01); *C07D 487/04* (2013.01); *C07D 493/04* (2013.01); *C07D 493/22* (2013.01); *C07D 495/22* (2013.01); *H01L 51/0052* (2013.01); *H01L 51/006* (2013.01);
(Continued)

(58) Field of Classification Search
None
See application file for complete search history.

(56) References Cited

U.S. PATENT DOCUMENTS 9,112,157 B2 8/2015 Brown et al.
2010/0032658 A1 2/2010 Lee et al.
(Continued)

FOREIGN PATENT DOCUMENTS

CN 104673276 6/2015
IN 201917041006 11/2019
(Continued)

*Primary Examiner* — Robert S Loewe
(74) *Attorney, Agent, or Firm* — Dentons US LLP

(57) ABSTRACT

Provided is a compound of Chemical Formula 1:

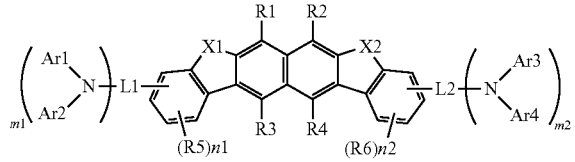

and an organic light emitting device comprising the same.

11 Claims, 3 Drawing Sheets

(51) Int. Cl.
  *C07C 211/54* (2006.01)
  *C07D 487/04* (2006.01)
  *C07D 493/04* (2006.01)
  *C07D 493/22* (2006.01)
  *C07D 495/22* (2006.01)
  *H01L 51/42* (2006.01)
  *H01L 51/50* (2006.01)

(52) U.S. Cl.
  CPC ...... *H01L 51/0072* (2013.01); *H01L 51/0073* (2013.01); *H01L 51/0074* (2013.01); *H01L 51/4273* (2013.01); *H01L 51/5072* (2013.01); *H01L 51/5092* (2013.01)

(56) References Cited

U.S. PATENT DOCUMENTS

| | | |
|---|---|---|
| 2016/0225992 A1 | 8/2016 | Ito et al. |
| 2019/0378992 A1 | 12/2019 | Skulason et al. |
| 2019/0393420 A1 | 12/2019 | Takeda et al. |
| 2021/0347782 A1* | 11/2021 | Takeda ................ C07D 495/00 |

FOREIGN PATENT DOCUMENTS

| | | |
|---|---|---|
| JP | 2010045281 | 2/2010 |
| JP | 2013232521 | 11/2013 |
| KR | 10-20100007780 | 1/2010 |
| KR | 20110108475 | 10/2011 |
| KR | 10-20130073700 | 7/2013 |
| KR | 10-20160089033 | 7/2016 |
| KR | 10-20190075009 | 6/2019 |
| KR | 10-20190129946 | 11/2019 |
| WO | 2018097937 | 5/2018 |
| WO | 2018167612 | 9/2018 |

* cited by examiner

【FIG. 1】
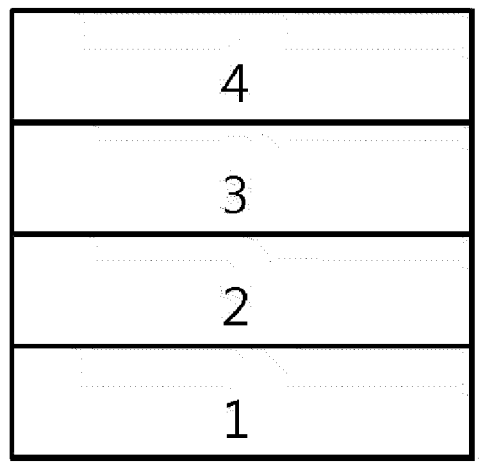
【FIG. 2】
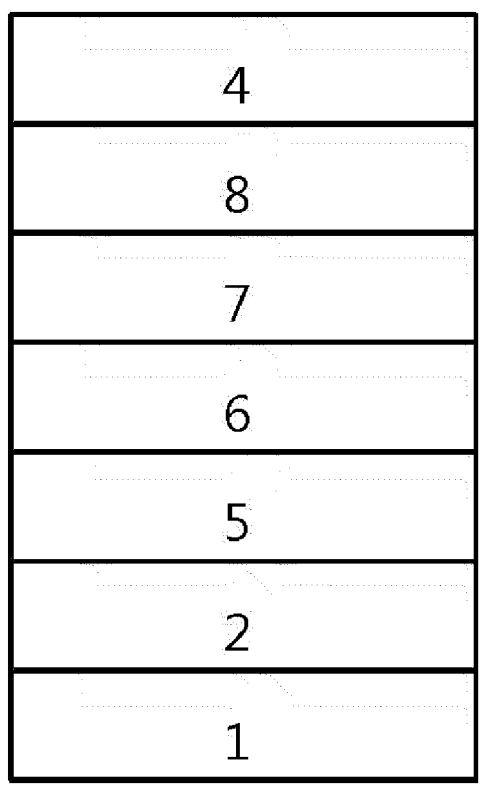

【FIG 4】
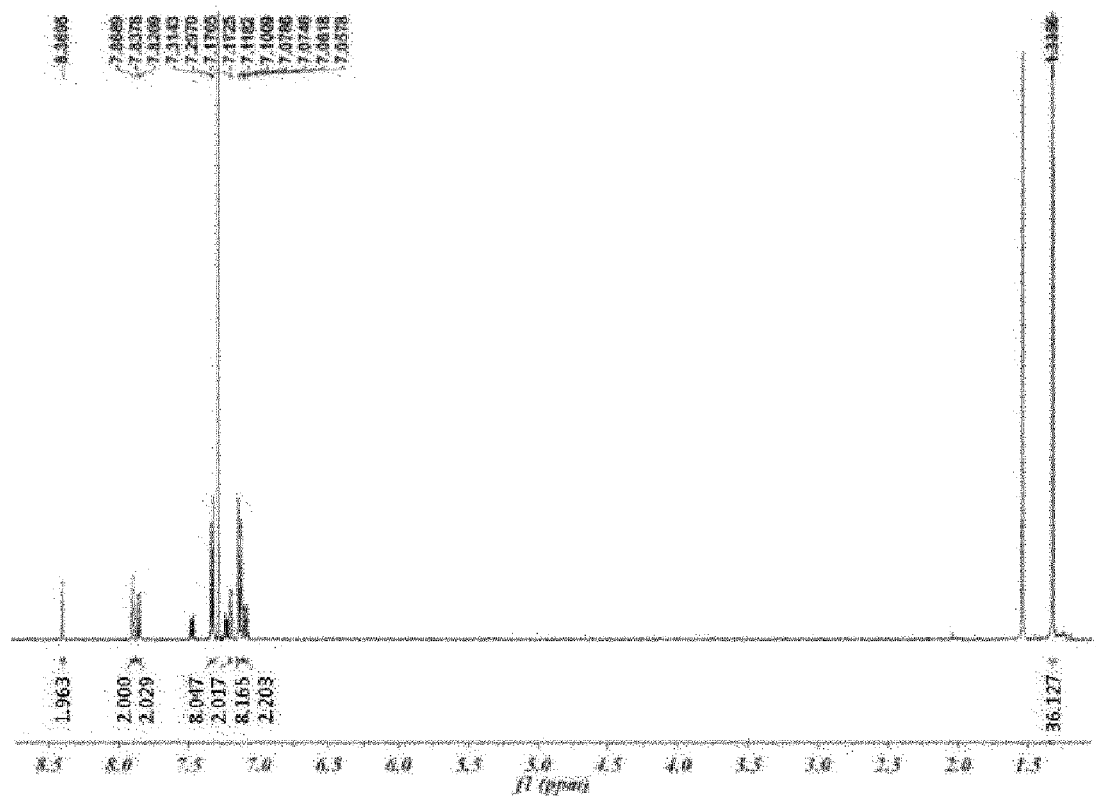

POLYCYCLIC COMPOUND AND ORGANIC LIGHT EMITTING ELEMENT COMPRISING SAME

CROSS-REFERENCE TO RELATED APPLICATION(S)

This application is a National Stage Application of International Application No. PCT/KR2018/012475 filed on Oct. 22, 2018, which claims priority to and the benefits of Korean Patent Application No. 10-2017-0136798, filed with the Korean Intellectual Property Office on Oct. 20, 2017, the entire contents of which are incorporated herein by reference.

TECHNICAL FIELD

The present specification relates to a compound and an organic light emitting device comprising the same.

BACKGROUND

An organic light emitting device in the present specification is a light emitting device using an organic semiconductor material, and requires an exchange of holes and/or electrons between an electrode and the organic semiconductor material. An organic light emitting device can be largely divided into two types as follows depending on the operation principle. The first is a light emitting device type in which excitons are formed in an organic material layer by photons introduced to a device from an external light source, these excitons are separated into electrons and holes, and these electrons and holes are each transferred to different electrodes and used as a current source (voltage source). The second is a light emitting device type in which, by applying a voltage or current to two or more electrodes, holes and/or electrons are injected into an organic semiconductor material layer forming an interface with the electrodes, and the light emitting device is operated by the injected electrons and holes.

An organic light emission phenomenon generally refers to a phenomenon converting electrical energy to light energy using an organic material. An organic light emitting device using an organic light emission phenomenon normally has a structure comprising an anode, a cathode, and an organic material layer therebetween. Herein, the organic material layer is often formed in a multilayer structure formed with different materials in order to increase efficiency and stability of the organic light emitting device, and for example, can be formed with a hole injection layer, a hole transfer layer, a light emitting layer, an electron transfer layer, an electron injection layer and the like. When a voltage is applied between the two electrodes in such an organic light emitting device structure, holes and electrons are injected to the organic material layer from the anode and the cathode, respectively, and when the injected holes and electrons meet, excitons are formed, and light emits when these excitons fall back to the ground state. Such an organic light emitting device is known to have properties such as self-emission, high luminance, high efficiency, low driving voltage, wide viewing angle and high contrast.

Materials used as an organic material layer in an organic light emitting device can be divided into a light emitting material and a charge transfer material, for example, a hole injection material, a hole transfer material, an electron transfer material, an electron injection material and the like depending on the function. The light emitting material comprises, depending on light emitting color, blue, green and red light emitting materials, and yellow and orange light emitting materials required for obtaining better natural colors.

In addition, in order to increase color purity and light emission efficiency through energy transition, a host/dopant-based can be used as the light emitting material. The principle is that light with high efficiency is produced when mixing a small amount of dopant having a smaller energy band gap and superior light emission efficiency compared to a host mainly consisting a light emitting layer into the light emitting layer by the transferring of excitons produced in the host to the dopant. Herein, the wavelength of the host is shifted to the wavelength band of the dopant, and therefore, light with a target wavelength can be obtained depending on the types of the dopant used.

In order to sufficiently exhibit excellent properties that the above-described organic light emitting device has, materials forming an organic material layer in the device, for example, a hole injection material, a hole transfer material, a light emitting material, an electron transfer material, an electron injection material and the like are supported by stable and efficient materials, and therefore, development of new materials has been continuously required.

PRIOR ART DOCUMENTS

Patent Documents (Patent Document 1) Korean Patent Application Laid-Open Publication No. 2011-108475

BRIEF DESCRIPTION

Technical Problem

The present specification describes a compound and an organic light emitting device comprising the same.

Technical Solution

One embodiment of the present specification provides a compound of Chemical Formula 1:

[Chemical Formula 1]

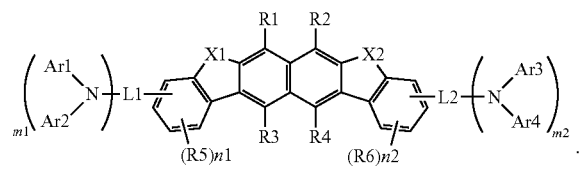

In Chemical Formula 1,

X1 and X2 are the same as or different from each other, and each independently is O, S, CRaRb or NRc, Ra, Rb, Rc and R1 to R6 are the same as or different from each other, and each independently is hydrogen, deuterium, a halogen group, a cyano group, a sulfide group, a sulfonyl group, a substituted or unsubstituted alkyl group, a substituted or unsubstituted cycloalkyl group, a substituted or unsubstituted arylamine group, a substituted or unsubstituted aryl group, or a substituted or unsubstituted heteroaryl group;

Ar1 to Ar4 are the same as or different from each other, and each independently is a substituted or unsubstituted aryl group, or a substituted or unsubstituted heteroaryl group, or adjacent groups bond to each other to form a substituted or unsubstituted ring, L1 and L2 are the same as or different from each other, and each independently is a direct bond or a substituted or unsubstituted arylene group, n1 and n2 are each an integer of 0 to 3, and when n1 and n2 are each 2 or greater, substituents in the parentheses are the same as or different from each other, and m1 and m2 are each an integer of 1 to 4, and m1+m2≥2 and n1+n2≤6.

Another embodiment of the present specification provides an organic light emitting device comprising a first electrode; a second electrode provided opposite to the first electrode; and one or more organic material layers provided between the first electrode and the second electrode, wherein one or more layers of the organic material layers comprise the compound.

Advantageous Effects

A compound described in the present specification can be used as a material of an organic material layer used in an organic light emitting device. The compound according to at least one embodiment exhibits high color purity and long lifetime properties particularly in a blue organic light emitting device. Particularly, the compound described in the present specification can be used as a material of a hole injection layer, a hole transfer layer, an electron blocking layer, a hole blocking layer, an electron transfer layer or an electron injection layer as well as a light emitting layer.

DESCRIPTION OF DRAWINGS

FIG. 1 illustrates an example of an organic light emitting device formed with a substrate (1), an anode (2), a light emitting layer (3) and a cathode (4).

FIG. 2 illustrates an example of an organic light emitting device formed with a substrate (1), an anode (2), a hole injection layer (5), a hole transfer layer (6), a light emitting layer (7), an electron transfer layer (8) and a cathode (4).

Figure 3:
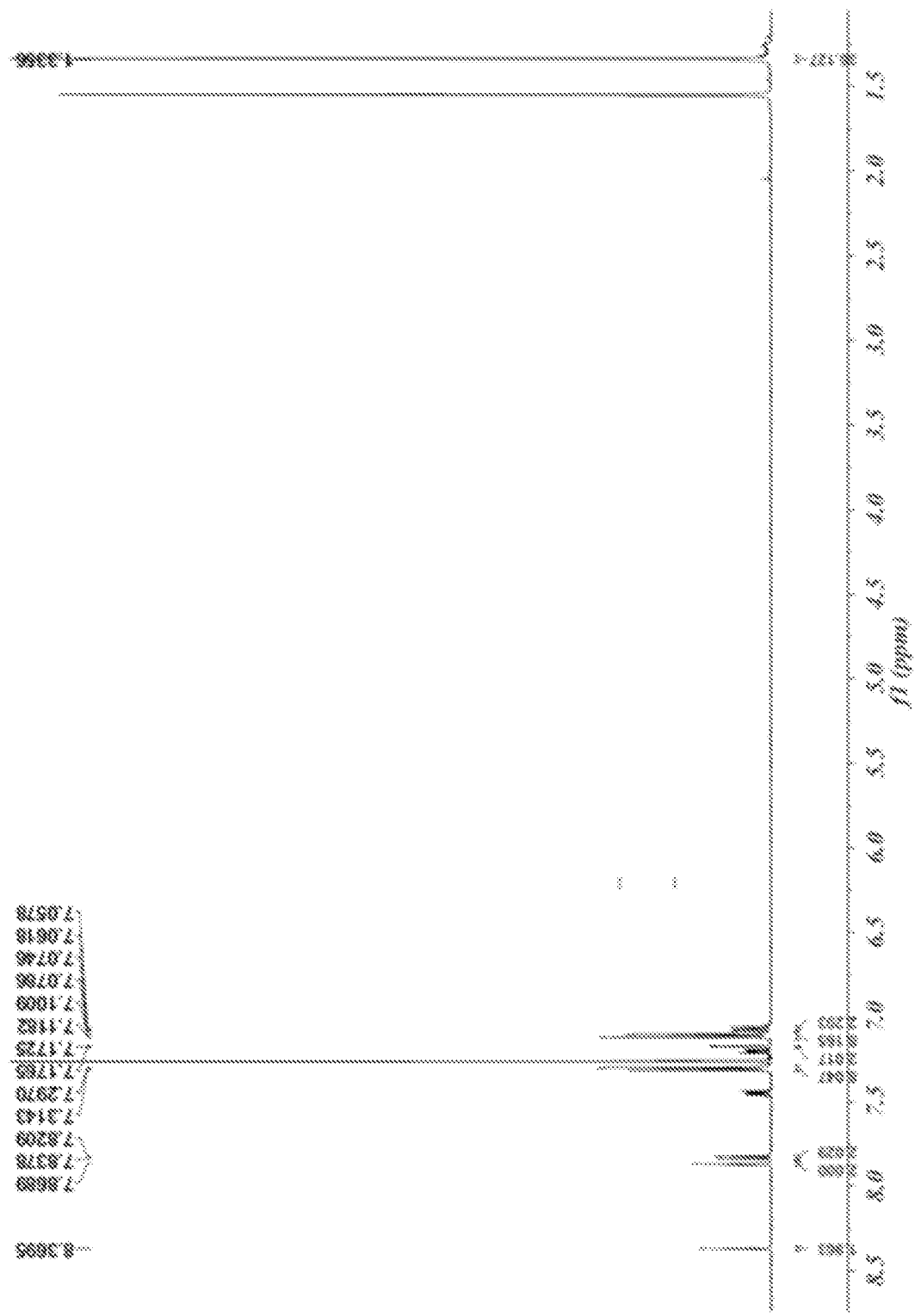
FIG. 3 is a diagram showing proton NMR data of Compound 1.

1: Substrate
2: Anode
3: Light Emitting Layer
4: Cathode
5: Hole Injection Layer
6: Hole Transfer Layer
7: Light Emitting Layer
8: Electron Transfer Layer

DETAILED DESCRIPTION

Hereinafter, the present specification will be described in more detail.

One embodiment of the present specification provides a compound of the following Chemical Formula 1. The compound of the following Chemical Formula 1 has a solid core structure by a fused 6-membered ring, and thereby has advantages of exhibiting long lifetime properties and having a small stokes shift, and as a result, high color gamut can be obtained as well as high efficiency.

[Chemical Formula 1]

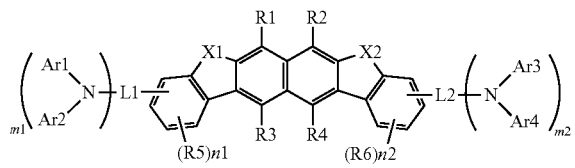

In Chemical Formula 1,

X1 and X2 are the same as or different from each other, and each independently is O, S, CRaRb or NRc, Ra, Rb, Rc and R1 to R6 are the same as or different from each other, and each independently is hydrogen, deuterium, a halogen group, a cyano group, a sulfide group, a sulfonyl group, a substituted or unsubstituted alkyl group, a substituted or unsubstituted cycloalkyl group, a substituted or unsubstituted arylamine group, a substituted or unsubstituted aryl group, or a substituted or unsubstituted heteroaryl group;

Ar1 to Ar4 are the same as or different from each other, and each independently is a substituted or unsubstituted aryl group, or a substituted or unsubstituted heteroaryl group, or adjacent groups bond to each other to form a substituted or unsubstituted ring;

L1 and L2 are the same as or different from each other, and each independently is a direct bond or a substituted or unsubstituted arylene group;

n1 and n2 are each an integer of 0 to 3, and when n1 and n2 are each 2 or greater, substituents in the parentheses are the same as or different from each other; and m1 and m2 are each an integer of 1 to 4, and m1+m2≥2 and n1+n2≤6.

In the present specification, a description of a certain part "comprising" certain constituents means capable of further comprising other constituents, and does not exclude other constituents unless particularly stated on the contrary.

In the present specification, a description of one member being placed "on" another member comprises not only a case of the one member adjoining the another member but a case of still another member being present between the two members.

Examples of substituents in the present specification are described below, however, the substituents are not limited thereto.

The term "substitution" means a hydrogen atom bonding to a carbon atom of a compound is changed to another substituent, and the position of substitution is not limited as long as it is a position at which a hydrogen atom is substituted, that is, a position at which a substituent can substitute, and when two or more substituents substitute, the two or more substituents can be the same as or different from each other.

In the present specification, the term "substituted or unsubstituted" means being substituted with one, two or more substituents selected from the group consisting of deuterium, a halogen group, a cyano group, a substituted or unsubstituted alkyl group, a substituted or unsubstituted cycloalkyl group, a substituted or unsubstituted arylamine group, a substituted or unsubstituted aryl group, and a substituted or unsubstituted heterocyclic group, or being substituted with a substituent linking two or more substituents among the substituents illustrated above, or having no substituents. For example, "a substituent linking two or more substituents" can comprise a biphenyl group. In other words, a biphenyl group can be an aryl group, or interpreted as a substituent linking two phenyl groups.

Examples of the substituents are described below, however, the substituents are not limited thereto.

In the present specification, examples of the halogen group can comprise fluorine (F), chlorine (Cl), bromine (Br) or iodine (I).

In the present specification, the sulfonyl group means —SO$_2$—R$_a$, and R$_a$ can be a substituted or unsubstituted aryl group having 6 to 30 carbon atoms.

In the present specification, the sulfide group means —S—R$_b$, and R$_b$ can be a substituted or unsubstituted aryl group having 6 to 30 carbon atoms.

In the present specification, the alkyl group can be linear or branched, and although not particularly limited thereto, the number of carbon atoms is preferably from 1 to 60. According to one embodiment, the number of carbon atoms of the alkyl group is from 1 to 30. According to another embodiment, the number of carbon atoms of the alkyl group is from 1 to 20. According to another embodiment, the number of carbon atoms of the alkyl group is from 1 to 10. Specific examples of the alkyl group can comprise a methyl group, an ethyl group, an n-propyl group, an isopropyl group, an n-butyl group, an isobutyl group, a tert-butyl group, an n-pentyl group, an n-hexyl group, an n-heptyl group, an n-octyl group and the like, but are not limited thereto.

In the present specification, the cycloalkyl group is not particularly limited, but preferably has 3 to 60 carbon atoms, and according to one embodiment, the number of carbon atoms of the cycloalkyl group is from 3 to 30. According to another embodiment, the number of carbon atoms of the cycloalkyl group is from 3 to 20. According to another embodiment, the number of carbon atoms of the cycloalkyl group is from 3 to 6. Specific examples thereof can comprise a cyclopropyl group, a cyclobutyl group, a cyclopentyl group, a cyclohexyl group, a cycloheptyl group, a cyclooctyl group and the like, but are not limited thereto.

In the present specification, examples of the arylamine group comprise a substituted or unsubstituted monoarylamine group, a substituted or unsubstituted diarylamine group, or a substituted or unsubstituted triarylamine group. The aryl group in the arylamine group can be a monocyclic aryl group or a polycyclic aryl group. The arylamine group comprising two or more aryl groups can comprise monocyclic aryl groups, polycyclic aryl groups, or both monocyclic aryl groups and polycyclic aryl groups.

Specific examples of the arylamine group can comprise a phenylamine group, a naphthylamine group, a biphenylamine group, an anthracenylamine group, a 3-methyl-phenylamine group, a 4-methyl-naphthylamine group, a 2-methyl-biphenylamine group, a 9-methyl-anthracenylamine group, a diphenylamine group, a phenylnaphthylamine group, a biphenylphenylamine group and the like, but are not limited thereto.

In the present specification, the aryl group is not particularly limited, but preferably has 6 to 60 carbon atoms, and can be a monocyclic aryl group or a polycyclic aryl group. According to one embodiment, the number of carbon atoms of the aryl group is from 6 to 30. According to one embodiment, the number of carbon atoms of the aryl group is from 6 to 20. When the aryl group is a monocyclic aryl group, examples thereof can comprise a phenyl group, a biphenyl group, a terphenyl group and the like, but are not limited thereto. Examples of the polycyclic aryl group can comprise a naphthyl group, an anthracenyl group, a phenanthrenyl group, a pyrenyl group, a perylenyl group, a triphenyl group, a chrysenyl group, a fluorenyl group, a benzofluorenyl group and the like, but are not limited thereto.

In the present specification, the fluorenyl group can be substituted, and two substituents can bond to each other to form a spiro structure.

When the fluorenyl group is substituted, spirofluorenyl groups such as

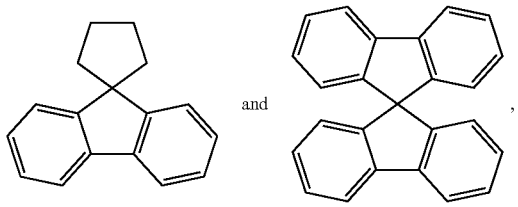

and or substituted fluorenyl groups such as

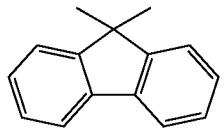

(9,9-dimethylfluorenyl group) and

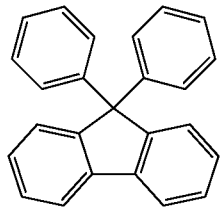 [SMILES: c1ccc(C2(c3ccccc3)c3ccccc3-c3ccccc32)cc1]

(9,9-diphenylfluorenyl group) can be included. However, the structure is not limited thereto.

In the present specification, the heterocyclic group is a cyclic group comprising one or more of N, O, P, S, Si and Se as a heteroatom, and although not particularly limited thereto, the number of carbon atoms is preferably from 2 to 60. According to one embodiment, the number of carbon atoms of the heterocyclic group is from 2 to 30. Examples of the heterocyclic group can comprise a pyridyl group, a pyrrole group, a pyrimidyl group, a pyridazinyl group, a furanyl group, a thiophenyl group, an imidazole group, a pyrazole group, a dibenzofuranyl group, a dibenzothiophenyl group, a naphthobenzofuranyl group, a naphthobenzothiophenyl group,

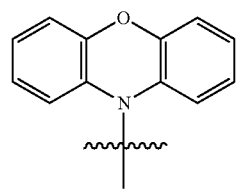 [SMILES: *N1c2ccccc2Oc2ccccc21]

and the like, but are not limited thereto.

In the present specification, descriptions on the heterocyclic group provided above can be applied to the heteroaryl group except that the heteroaryl group is aromatic.

In the present specification, descriptions on the aryl group provided above can be applied to the arylene group except that the arylene group is divalent.

In the present specification, descriptions on the heteroaryl group provided above can be applied to the heteroarylene group except that the heteroarylene group is divalent.

In the present specification, the "adjacent" group can mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring can be interpreted as groups "adjacent" to each other.

In the present specification, in the substituted or unsubstituted ring formed by adjacent groups bonding to each other, the "ring" means a hydrocarbon ring or a heteroring.

In the present specification, the hydrocarbon ring can be aromatic, aliphatic, or a fused ring of aromatic and aliphatic, and can be selected from among the examples of the cycloalkyl group or the aryl group except for those that are not monovalent.

In the present specification, descriptions on the aryl group provided can be applied to the aromatic hydrocarbon ring except for those that are not monovalent.

In the present specification, the heteroring comprises one or more atoms that are not carbon, that is, heteroatoms, and specifically, the heteroatom can comprise one or more atoms selected from the group consisting of N, O, P, S, Si, Se and the like. The heteroring can be monocyclic or polycyclic, aromatic, aliphatic, or a fused ring of aromatic and aliphatic, and the aromatic heteroring and can be selected from among the examples of the heteroaryl group except for those that are not monovalent.

According to one embodiment of the present specification, m1 and m2 are each an integer of 1 to 4, and m1+m2≥2 and n1+n2≤6.

In another embodiment, m1 and m2 are 1.

According to one embodiment of the present specification, Chemical Formula 1 can be the following Chemical Formula 2:

[Chemical Formula 2]

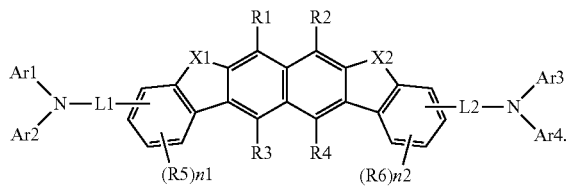

In Chemical Formula 2,

X1, X2, R1 to R6, L1, L2, n1, n2 and Ar1 to Ar4 have the same definitions as in Chemical Formula 1.

In one embodiment of the present specification, L1 and L2 are the same as or different from each other, and each independently is a direct bond or a substituted or unsubstituted arylene group having 6 to 60 carbon atoms.

According to another embodiment, L1 and L2 are the same as or different from each other, and each independently is a direct bond or a substituted or unsubstituted arylene group having 6 to 30 carbon atoms.

In another embodiment, L1 and L2 are a direct bond, a substituted or unsubstituted phenylene group, a substituted or unsubstituted biphenylene group, or a substituted or unsubstituted naphthylene group.

According to another embodiment, L1 and L2 are a direct bond, a phenylene group, a biphenylene group, or a naphthylene group.

According to one embodiment of the present specification, Ar1 to Ar4 are the same as or different from each other, and each independently is a substituted or unsubstituted aryl group having 6 to 60 carbon atoms, or a substituted or unsubstituted heteroaryl group having 2 to 60 carbon atoms, or adjacent groups bond to each other to form a substituted or unsubstituted ring.

According to another embodiment, Ar1 to Ar4 are the same as or different from each other, and each independently is a substituted or unsubstituted aryl group having 6 to 30 carbon atoms, or a substituted or unsubstituted heteroaryl group having 2 to 30 carbon atoms, or adjacent groups bond to each other to form a substituted or unsubstituted ring.

According to another embodiment, Ar1 to Ar4 are the same as or different from each other, and each independently is an aryl group having 6 to 30 carbon atoms unsubstituted or substituted with one or more selected from the group consisting of an alkyl group having 1 to 20 carbon atoms, or a heteroaryl group having 2 to 30 carbon atoms unsubstituted or substituted with one or more selected from the group consisting of an alkyl group having 1 to 20 carbon atoms and an aryl group having 6 to 30 carbon atoms, or adjacent groups bond to each other to form a substituted or unsubstituted ring.

According to another embodiment, Ar1 to Ar4 are the same as or different from each other, and each independently is a phenyl group unsubstituted or substituted with one or more selected from the group consisting of an alkyl group having 1 to 20 carbon atoms, a biphenyl group unsubstituted or substituted with one or more selected from the group consisting of an alkyl group having 1 to 20 carbon atoms, a naphthyl group unsubstituted or substituted with one or more selected from the group consisting of an alkyl group having 1 to 20 carbon atoms, a fluorenyl group unsubstituted or substituted with one or more selected from the group consisting of an alkyl group having 1 to 20 carbon atoms, a benzofluorenyl group unsubstituted or substituted with one or more selected from the group consisting of an alkyl group having 1 to 20 carbon atoms, a dibenzofuranyl group unsubstituted or substituted with one or more selected from the group consisting of an alkyl group having 1 to 20 carbon atoms and an aryl group having 6 to 30 carbon atoms, a dibenzothiophenyl group unsubstituted or substituted with one or more selected from the group consisting of an alkyl group having 1 to 20 carbon atoms and an aryl group having 6 to 30 carbon atoms, a carbazole group unsubstituted or substituted with one or more selected from the group consisting of an alkyl group having 1 to 20 carbon atoms and an aryl group having 6 to 30 carbon atoms, a naphthobenzofuranyl group unsubstituted or substituted with one or more selected from the group consisting of an alkyl group having 1 to 20 carbon atoms and an aryl group having 6 to 30 carbon atoms, or a naphthobenzothiophenyl group unsubstituted or substituted with one or more selected from the group consisting of an alkyl group having 1 to 20 carbon atoms and an aryl group having 6 to 30 carbon atoms, or adjacent groups bond to each other to form a substituted or unsubstituted ring.

In another embodiment, Ar1 to Ar4 are the same as or different from each other, and each independently is a phenyl group unsubstituted or substituted with one or more selected from the group consisting of a methyl group, an ethyl group, an n-propyl group, an isopropyl group, an n-butyl group and a tert-butyl group, a biphenyl group unsubstituted or substituted with one or more selected from the group consisting of a methyl group, an ethyl group, an n-propyl group, an isopropyl group, an n-butyl group and a tert-butyl group, a naphthyl group unsubstituted or substituted with one or more selected from the group consisting of a methyl group, an ethyl group, an n-propyl group, an isopropyl group, an n-butyl group and a tert-butyl group, a fluorenyl group unsubstituted or substituted with one or more selected from the group consisting of a methyl group, an ethyl group, an n-propyl group, an isopropyl group, an n-butyl group and a tert-butyl group, a benzofluorenyl group unsubstituted or substituted with one or more selected from the group consisting of a methyl group, an ethyl group, an n-propyl group, an isopropyl group, an n-butyl group and a tert-butyl group, a dibenzofuranyl group unsubstituted or substituted with one or more selected from the group consisting of a methyl group, an ethyl group, an n-propyl group, an isopropyl group, an n-butyl group, a tert-butyl group, a phenyl group, a biphenyl group and a naphthyl group, a dibenzothiophenyl group unsubstituted or substituted with one or more selected from the group consisting of a methyl group, an ethyl group, an n-propyl group, an isopropyl group, an n-butyl group, a tert-butyl group, a phenyl group, a biphenyl group and a naphthyl group, a carbazole group unsubstituted or substituted with one or more selected from the group consisting of a methyl group, an ethyl group, an n-propyl group, an isopropyl group, an n-butyl group, a tert-butyl group, a phenyl group, a biphenyl group and a naphthyl group, a naphthobenzofuranyl group unsubstituted or substituted with one or more selected from the group consisting of a methyl group, an ethyl group, an n-propyl group, an isopropyl group, an n-butyl group, a tert-butyl group, a phenyl group, a biphenyl group and a naphthyl group, or a naphthobenzothiophenyl group unsubstituted or substituted with one or more selected from the group consisting of a methyl group, an ethyl group, an n-propyl group, an isopropyl group, an n-butyl group, a tert-butyl group, a phenyl group, a biphenyl group and a naphthyl group, or adjacent groups bond to each other to form a substituted or unsubstituted ring.

According to another embodiment, Ar1 and Ar2 bond to each other to form a substituted or unsubstituted ring.

In another embodiment, Ar1 and Ar2 bond to each other to form a substituted or unsubstituted heteroring.

According to another embodiment, Ar1 and Ar2 bond to each other to form a substituted or unsubstituted aromatic heteroring.

In another embodiment, Ar1 and Ar2 bond to each other to form substituted or unsubstituted carbazole.

According to another embodiment, Ar3 and Ar4 bond to each other to form a substituted or unsubstituted ring.

In another embodiment, Ar3 and Ar4 bond to each other to form a substituted or unsubstituted heteroring.

According to another embodiment, Ar3 and Ar4 bond to each other to form a substituted or unsubstituted aromatic heteroring.

In another embodiment, Ar3 and Ar4 bond to each other to form substituted or unsubstituted carbazole.

According to one embodiment of the present specification, Chemical Formula 1 can be the following Chemical Formula 3 or 4:

[Chemical Formula 3]

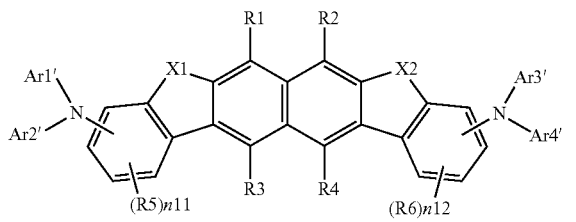

[Chemical Formula 4]

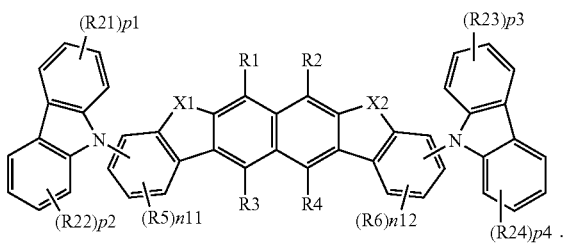

In Chemical Formulae 3 and 4,

X1, X2 and R1 to R6 have the same definitions as in Chemical Formula 1,

R21 to R24 are the same as or different from each other, and each independently is hydrogen, deuterium, a halogen group, a cyano group, a substituted or unsubstituted alkyl group, a substituted or unsubstituted cycloalkyl group, a substituted or unsubstituted aryl group, or a substituted or unsubstituted heteroaryl group;

Ar1' to Ar4' are the same as or different from each other, and each independently is a substituted or unsubstituted aryl group or a substituted or unsubstituted heteroaryl group;

n11 and n12 are each an integer of 0 to 3;

p1 to p4 are each an integer of 0 to 4; and when n11, n12 and p1 to p4 are 2 or greater, substituents in the parentheses are the same as or different from each other.

According to one embodiment of the present specification, Ar1' to Ar4' are the same as or different from each other, and each independently is a substituted or unsubstituted aryl group having 6 to 60 carbon atoms or a substituted or unsubstituted heteroaryl group having 2 to 60 carbon atoms.

According to another embodiment, Ar1' to Ar4' are the same as or different from each other, and each independently is a substituted or unsubstituted aryl group having 6 to 30 carbon atoms or a substituted or unsubstituted heteroaryl group having 2 to 30 carbon atoms.

According to another embodiment, Ar1' to Ar4' are the same as or different from each other, and each independently is an aryl group having 6 to 30 carbon atoms unsubstituted or substituted with one or more selected from the group consisting of an alkyl group having 1 to 20 carbon atoms or a heteroaryl group having 2 to 30 carbon atoms unsubstituted or substituted with one or more selected from the group consisting of an alkyl group having 1 to 20 carbon atoms and an aryl group having 6 to 30 carbon atoms.

According to another embodiment, Ar1' to Ar4' are the same as or different from each other, and each independently is a phenyl group unsubstituted or substituted with one or more selected from the group consisting of an alkyl group having 1 to 20 carbon atoms, a biphenyl group unsubstituted or substituted with one or more selected from the group consisting of an alkyl group having 1 to 20 carbon atoms, a naphthyl group unsubstituted or substituted with one or more selected from the group consisting of an alkyl group having 1 to 20 carbon atoms, a fluorenyl group unsubstituted or substituted with one or more selected from the group consisting of an alkyl group having 1 to 20 carbon atoms, a benzofluorenyl group unsubstituted or substituted with one or more selected from the group consisting of an alkyl group having 1 to 20 carbon atoms, a dibenzofuranyl group unsubstituted or substituted with one or more selected from the group consisting of an alkyl group having 1 to 20 carbon atoms and an aryl group having 6 to 30 carbon atoms, a dibenzothiophenyl group unsubstituted or substituted with one or more selected from the group consisting of an alkyl group having 1 to 20 carbon atoms and an aryl group having 6 to 30 carbon atoms, a carbazole group unsubstituted or substituted with one or more selected from the group consisting of an alkyl group having 1 to 20 carbon atoms and an aryl group having 6 to 30 carbon atoms, a naphthobenzofuranyl group unsubstituted or substituted with one or more selected from the group consisting of an alkyl group having 1 to 20 carbon atoms and an aryl group having 6 to 30 carbon atoms, or a naphthobenzothiophenyl group unsubstituted or substituted with one or more selected from the group consisting of an alkyl group having 1 to 20 carbon atoms and an aryl group having 6 to 30 carbon atoms.

In another embodiment, Ar1' to Ar4' are the same as or different from each other, and each independently is a phenyl group unsubstituted or substituted with one or more selected from the group consisting of a methyl group, an ethyl group, an n-propyl group, an isopropyl group, an n-butyl group and a tert-butyl group; a biphenyl group unsubstituted or substituted with one or more selected from the group consisting of a methyl group, an ethyl group, an n-propyl group, an isopropyl group, an n-butyl group and a tert-butyl group; a naphthyl group unsubstituted or substituted with one or more selected from the group consisting of a methyl group, an ethyl group, an n-propyl group, an isopropyl group, an n-butyl group and a tert-butyl group; a fluorenyl group unsubstituted or substituted with one or more selected from the group consisting of a methyl group, an ethyl group, an n-propyl group, an isopropyl group, an n-butyl group and a tert-butyl group; a benzofluorenyl group unsubstituted or substituted with one or more selected from the group consisting of a methyl group, an ethyl group, an n-propyl group, an isopropyl group, an n-butyl group and a tert-butyl group; a dibenzofuranyl group unsubstituted or substituted with one or more selected from the group consisting of a methyl group, an ethyl group, an n-propyl group, an isopropyl group, an n-butyl group, a tert-butyl group, a phenyl group, a biphenyl group and a naphthyl group; a dibenzothiophenyl group unsubstituted or substituted with one or more selected from the group consisting of a methyl group, an ethyl group, an n-propyl group, an isopropyl group, an n-butyl group, a tert-butyl group, a phenyl group, a biphenyl group and a naphthyl group; a carbazole group unsubstituted or substituted with one or more selected from the group consisting of a methyl group, an ethyl group, an n-propyl group, an isopropyl group, an n-butyl group, a tert-butyl group, a phenyl group, a biphenyl group and a naphthyl group; a naphthobenzofuranyl group unsubstituted or substituted with one or more selected from the group consisting of a methyl group, an ethyl group, an n-propyl group, an isopropyl group, an n-butyl group, a tert-butyl group, a phenyl group, a biphenyl group and a naphthyl group; or a naphthobenzothiophenyl group unsubstituted or substituted with one or more selected from the group consisting of a methyl group, an ethyl group, an n-propyl group, an isopropyl group, an n-butyl group, a tert-butyl group, a phenyl group, a biphenyl group and a naphthyl group.

According to one embodiment of the present specification, X1 and X2 are the same as or different from each other, and each independently is O, S, CRaRb or NRc. By the compound of Chemical Formula 1 comprising O, S, C or N as a central element (X1, X2) in the core structure, a device having long lifetime properties can be obtained when used in a device.

In another embodiment, X1 and X2 are O.

In another embodiment, X1 and X2 are S.

In another embodiment, X1 and X2 are CRaRb.

In another embodiment, X1 and X2 are NRc.

In another embodiment, any one of X1 and X2 is S, and the other one is O.

According to one embodiment of the present specification, Ra and Rb are the same as or different from each other, and each independently is hydrogen, a substituted or unsubstituted alkyl group, or a substituted or unsubstituted aryl group.

In another embodiment, Ra and Rb are the same as or different from each other, and each independently is hydrogen, a substituted or unsubstituted alkyl group having 1 to 60 carbon atoms, or a substituted or unsubstituted aryl group having 6 to 60 carbon atoms.

In another embodiment, Ra and Rb are the same as or different from each other, and each independently is hydrogen, a substituted or unsubstituted alkyl group having 1 to 30 carbon atoms, or a substituted or unsubstituted aryl group having 6 to 30 carbon atoms.

In another embodiment, Ra and Rb are the same as or different from each other, and each independently is a substituted or unsubstituted methyl group, a substituted or unsubstituted ethyl group, a substituted or unsubstituted n-propyl group, a substituted or unsubstituted isopropyl group, a substituted or unsubstituted n-butyl group, a substituted or unsubstituted tert-butyl group, a substituted or unsubstituted n-pentyl group, a substituted or unsubstituted n-hexyl group, a substituted or unsubstituted phenyl group, a substituted or unsubstituted biphenyl group, or a substituted or unsubstituted naphthyl group.

According to another embodiment, Ra and Rb are the same as or different from each other, and each independently is a methyl group, an ethyl group; an n-propyl group, an isopropyl group, an n-butyl group, a tert-butyl group, an n-pentyl group, an n-hexyl group, a phenyl group, a biphenyl group, or a naphthyl group.

In one embodiment of the present disclosure, Ra and Rb are a methyl group or a phenyl group.

According to one embodiment of the present specification, Rc is a substituted or unsubstituted aryl group.

In another embodiment, Rc is a substituted or unsubstituted aryl group having 6 to 60 carbon atoms.

According to another embodiment, Rc is a substituted or unsubstituted aryl group having 6 to 30 carbon atoms.

In another embodiment, Rc is an aryl group having 6 to 30 carbon atoms.

According to another embodiment, Rc is a phenyl group, a biphenyl group, or a naphthyl group.

In one embodiment of the present specification, R1 to R6 are the same as or different from each other, and each independently is hydrogen, a halogen group, a cyano group, a sulfide group, a sulfonyl group, a substituted or unsubstituted alkyl group having 1 to 20 carbon atoms, a substituted or unsubstituted cycloalkyl group having 3 to 60 carbon atoms, a substituted or unsubstituted arylamine group having 6 to 60 carbon atoms, a substituted or unsubstituted aryl group having 6 to 60 carbon atoms, or a substituted or unsubstituted heteroaryl group having 2 to 60 carbon atoms.

According to another embodiment, R1 to R6 are the same as or different from each other, and each independently is hydrogen, a cyano group, a sulfide group, a sulfonyl group, a substituted or unsubstituted alkyl group having 1 to 20 carbon atoms, a substituted or unsubstituted arylamine group having 6 to 60 carbon atoms, a substituted or unsubstituted aryl group having 6 to 60 carbon atoms, or a substituted or unsubstituted heteroaryl group having 2 to 60 carbon atoms.

According to another embodiment, R1 to R6 are the same as or different from each other, and each independently is hydrogen, a cyano group, a phenylsulfide group, a phenylsulfonyl group, a substituted or unsubstituted methyl group, a substituted or unsubstituted ethyl group, a substituted or unsubstituted n-propyl group, a substituted or unsubstituted isopropyl group, a substituted or unsubstituted n-butyl group, a substituted or unsubstituted tert-butyl group, a substituted or unsubstituted diphenylamine group, a substituted or unsubstituted phenyl group, a substituted or unsubstituted biphenyl group, a substituted or unsubstituted naphthyl group, a substituted or unsubstituted carbazole group, or

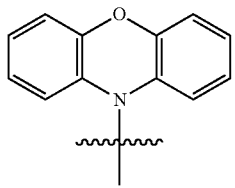

In another embodiment, R1 to R6 are the same as or different from each other, and each independently is hydrogen, a cyano group, a phenylsulfide group, a phenylsulfonyl group, a methyl group, an ethyl group, an n-propyl group, an isopropyl group, an n-butyl group, a tert-butyl group, a diphenylamine group, a phenyl group unsubstituted or substituted with a tert-butyl group, a biphenyl group, a naphthyl group, a carbazole group, or

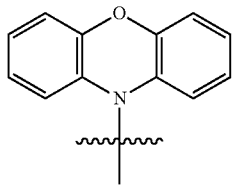

According to one embodiment of the present specification, n1 and n2 are 0 or 1.

In another embodiment, n11 and n12 are 0 or 1.

According to another embodiment, p1 to p4 are 0 or 1.

According to one embodiment of the present specification, R21 to R24 are the same as or different from each other, and each independently is hydrogen, a substituted or unsubstituted alkyl group, or a substituted or unsubstituted aryl group.

In another embodiment, R21 to R24 are the same as or different from each other, and each independently is hydrogen, a substituted or unsubstituted alkyl group having 1 to 60 carbon atoms, or a substituted or unsubstituted aryl group having 6 to 60 carbon atoms.

According to another embodiment, R21 to R24 are the same as or different from each other, and each independently is hydrogen, a substituted or unsubstituted alkyl group having 1 to 30 carbon atoms, or a substituted or unsubstituted aryl group having 6 to 30 carbon atoms.

In another embodiment, R21 to R24 are the same as or different from each other, and each independently is hydrogen or a substituted or unsubstituted alkyl group.

According to another embodiment, R21 to R24 are the same as or different from each other, and each independently is hydrogen or a substituted or unsubstituted alkyl group having 1 to 20 carbon atoms.

In another embodiment, R21 to R24 are the same as or different from each other, and each independently is hydrogen, a substituted or unsubstituted methyl group, a substituted or unsubstituted ethyl group, a substituted or unsubstituted n-propyl group, a substituted or unsubstituted isopropyl group, a substituted or unsubstituted n-butyl group, or a substituted or unsubstituted tert-butyl group.

According to another embodiment, R21 to R24 are the same as or different from each other, and each independently is hydrogen, a methyl group, an ethyl group, an n-propyl group, an isopropyl group, an n-butyl group, or a tert-butyl group.

According to one embodiment of the present specification, Chemical Formula 1 can be any one of the following Chemical Formulae 5 to 8:

[Chemical Formula 5]

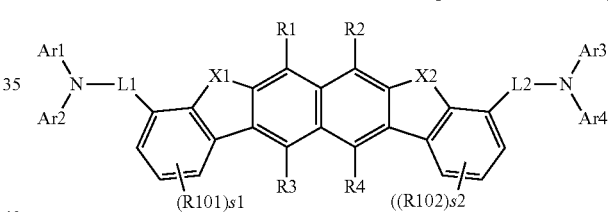

[Chemical Formula 6]

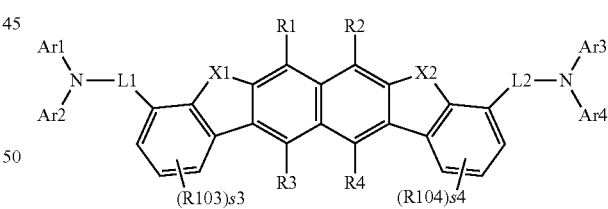

[Chemical Formula 7]

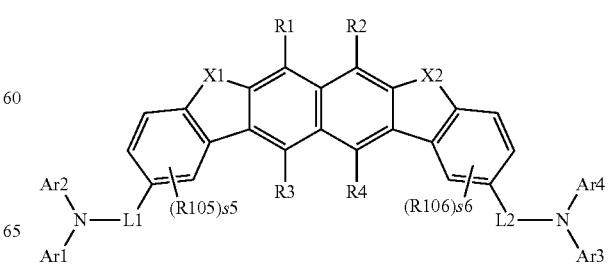

-continued

[Chemical Formula 8]

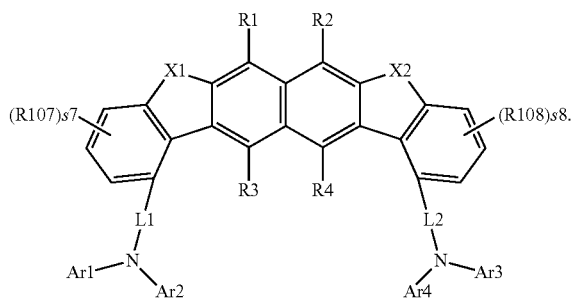

In Chemical Formulae 5 to 8,

X1, X2, R1 to R4, L1, L2 and Ar1 to Ar4 have the same definitions as in Chemical Formula 1, R101 to R108 are the same as or different from each other, and each independently is hydrogen, deuterium, a halogen group, a cyano group, a sulfide group, a sulfonyl group, a substituted or unsubstituted alkyl group, a substituted or unsubstituted cycloalkyl group, a substituted or unsubstituted arylamine group, a substituted or unsubstituted aryl group, or a substituted or unsubstituted heteroaryl group, and s1 to s8 are each an integer of 0 to 3, and when s1 to s8 are each an integer of 2 or greater, substituents in the parentheses are the same as or different from each other.

According to one embodiment of the present specification, R101 to R108 are the same as or different from each other, and each independently is hydrogen, a cyano group, a substituted or unsubstituted alkyl group having 1 to 30 carbon atoms, or a substituted or unsubstituted aryl group having 6 to 30 carbon atoms.

According to another embodiment, R101 to R108 are the same as or different from each other, and each independently is hydrogen, a cyano group, a substituted or unsubstituted methyl group, a substituted or unsubstituted propyl group, or a substituted or unsubstituted phenyl group.

In another embodiment, R101 to R108 are the same as or different from each other, and each independently is hydrogen, a cyano group, a substituted or unsubstituted methyl group, a substituted or unsubstituted isopropyl group, or a substituted or unsubstituted phenyl group.

According to another embodiment, R101 to R108 are the same as or different from each other, and each independently is hydrogen, a cyano group, a methyl group, an isopropyl group, or a phenyl group.

According to one embodiment of the present specification, s1 to s8 are each 0 or 1.

In one embodiment of the present specification, Chemical Formula 1 can be any one of the following Compound 1 to Compound 72:

Compound 1

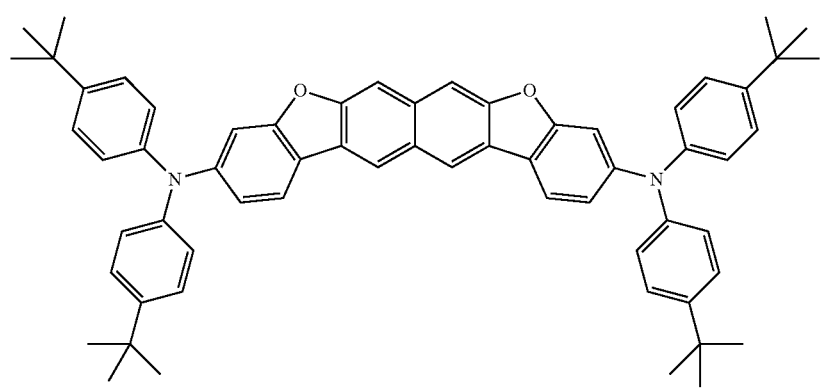

Compound 2

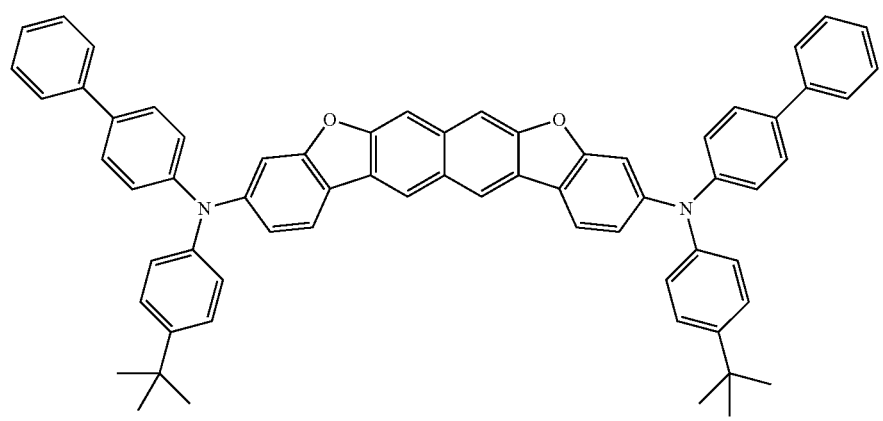

-continued
Compound 3
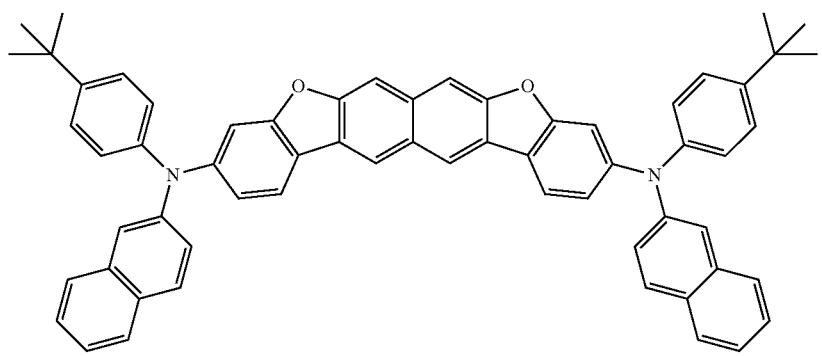
Compound 4
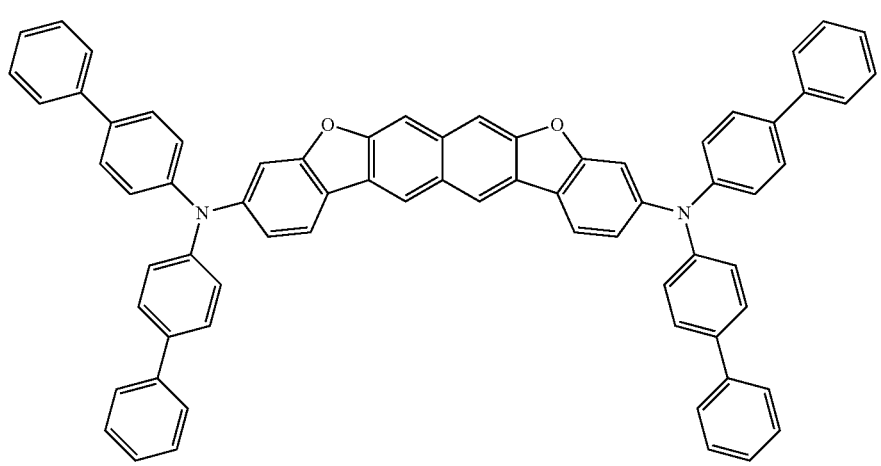
Compound 5
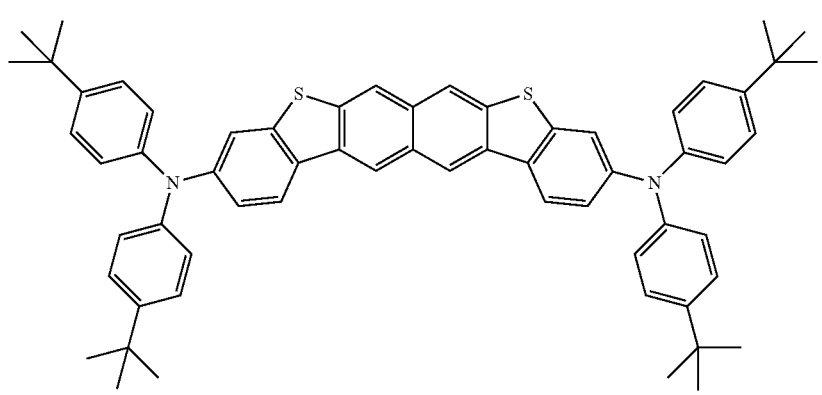
Compound 6
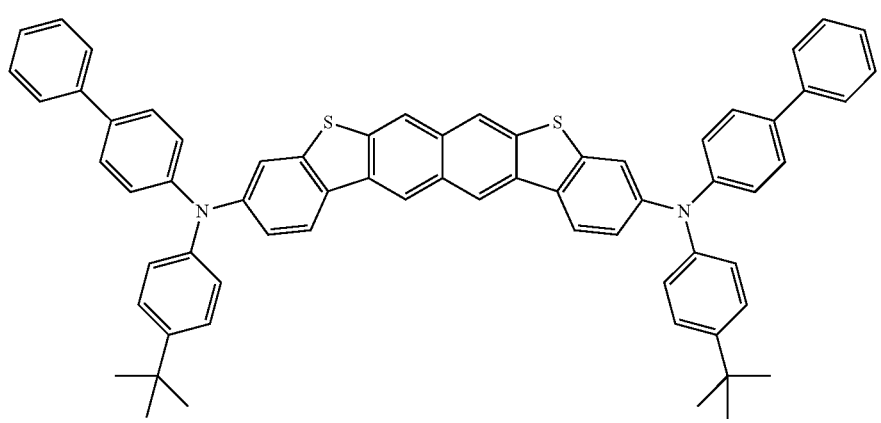

Compound 7
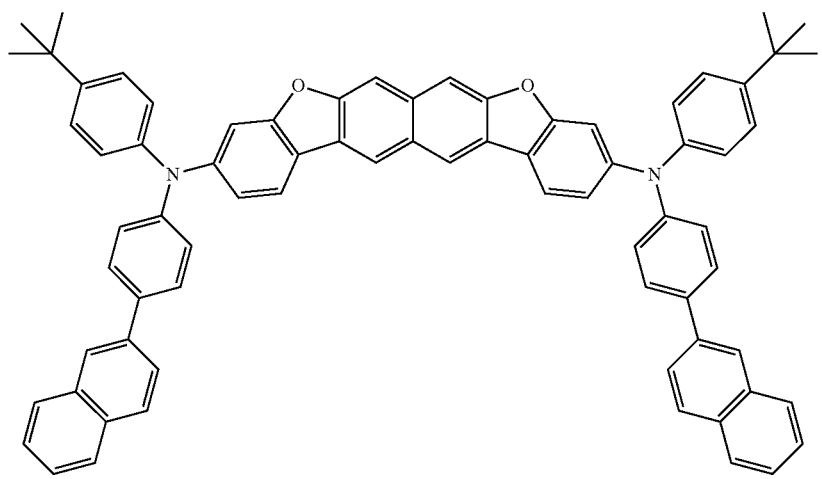
Compound 8
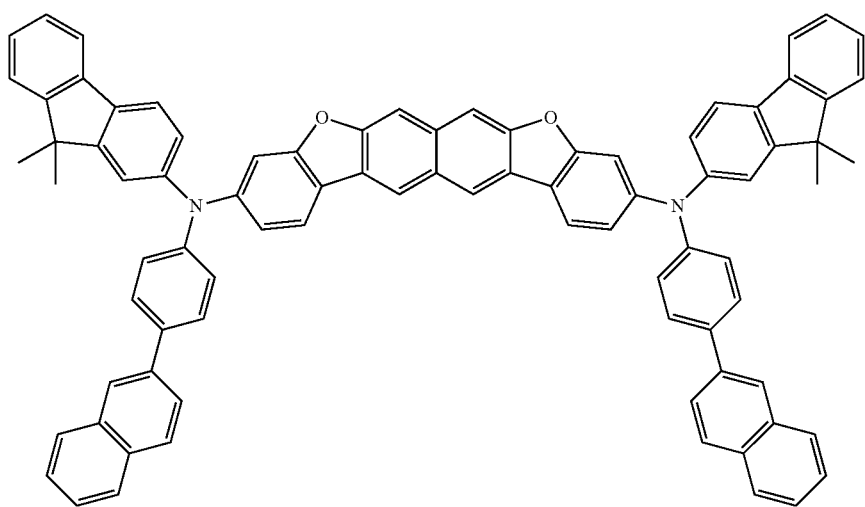
Compound 9
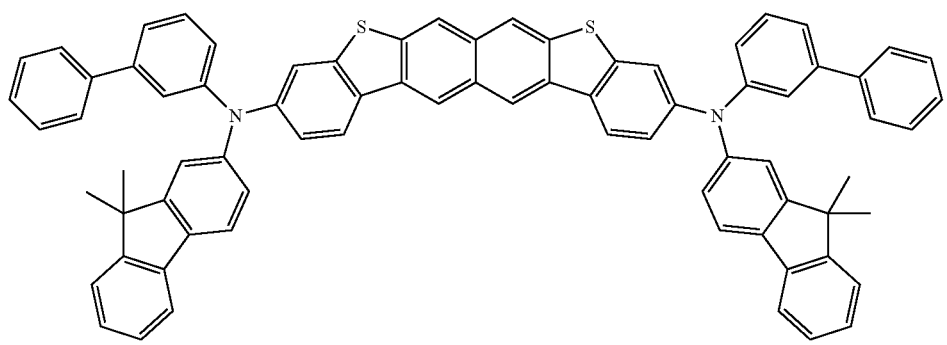

Compound 10
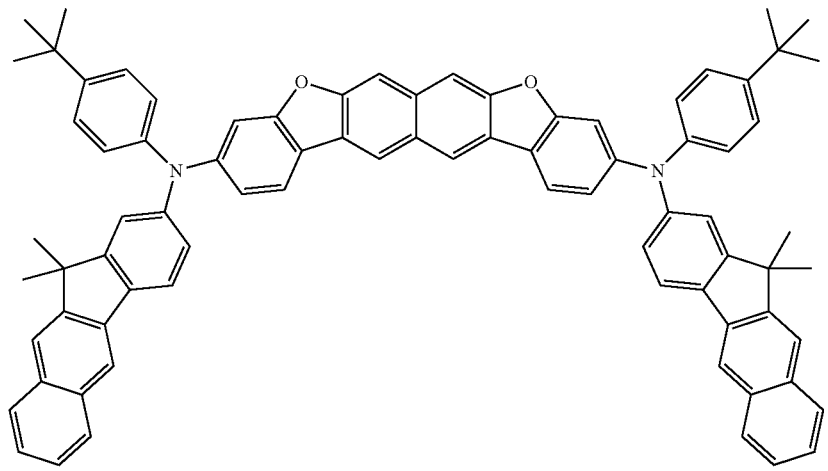
Compound 11
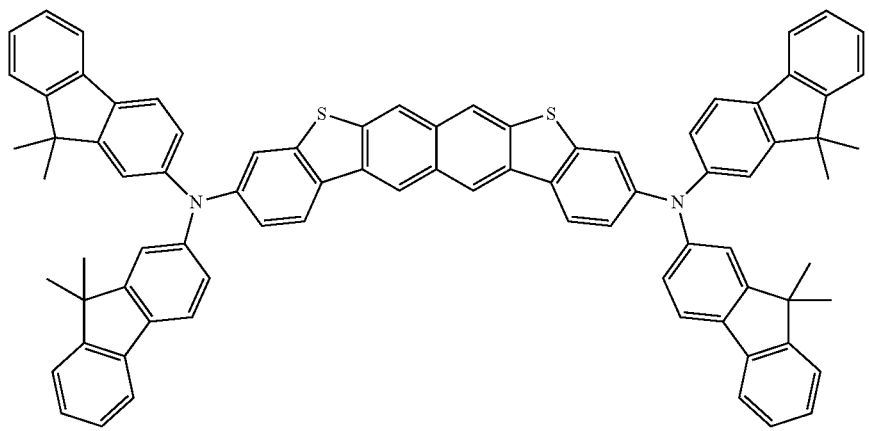
Compound 12
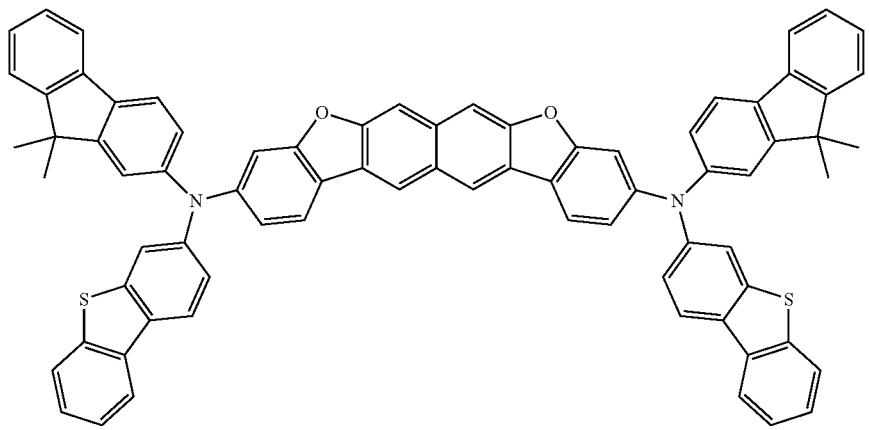

Compound 13
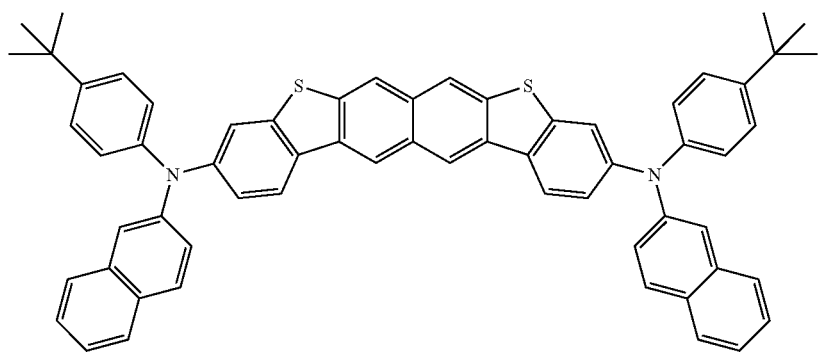
Compound 14
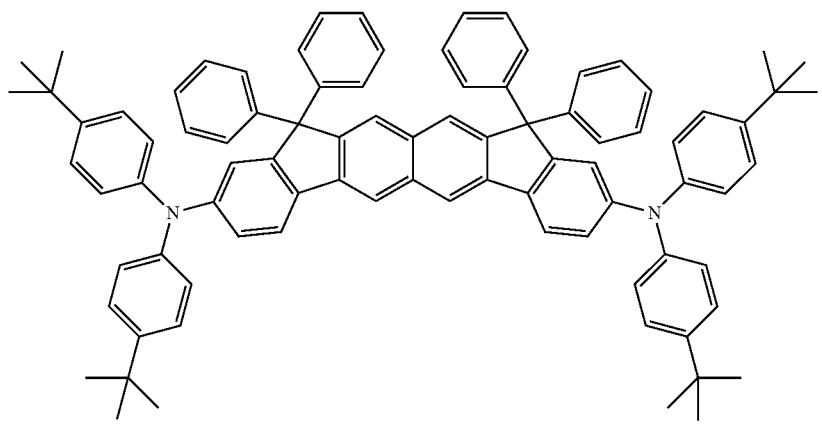
Compound 15
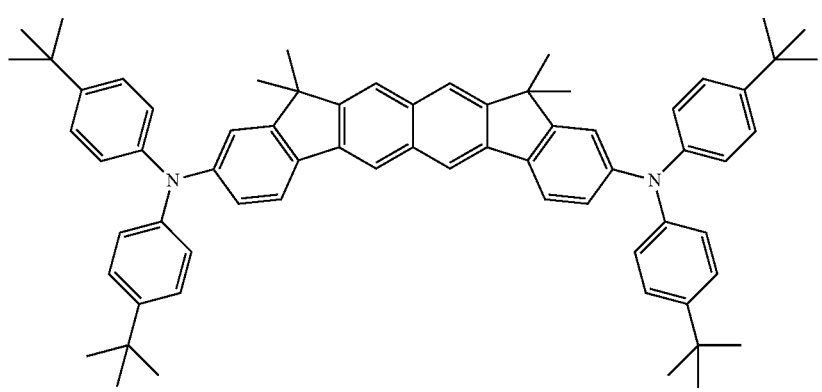
Compound 16
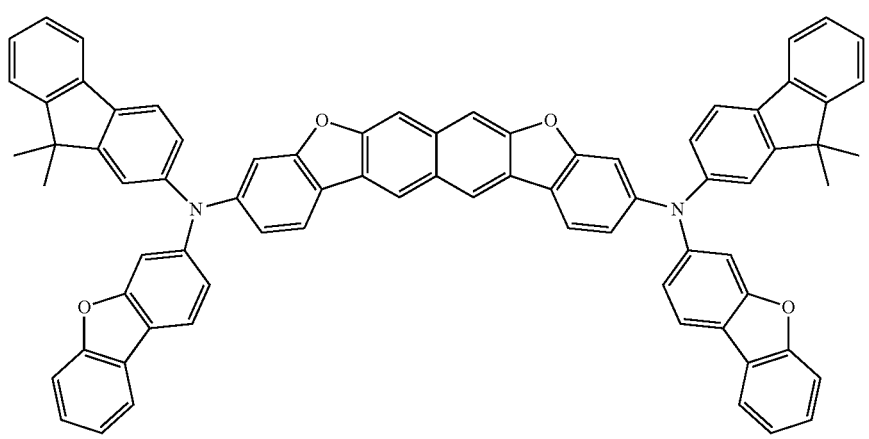

Compound 17
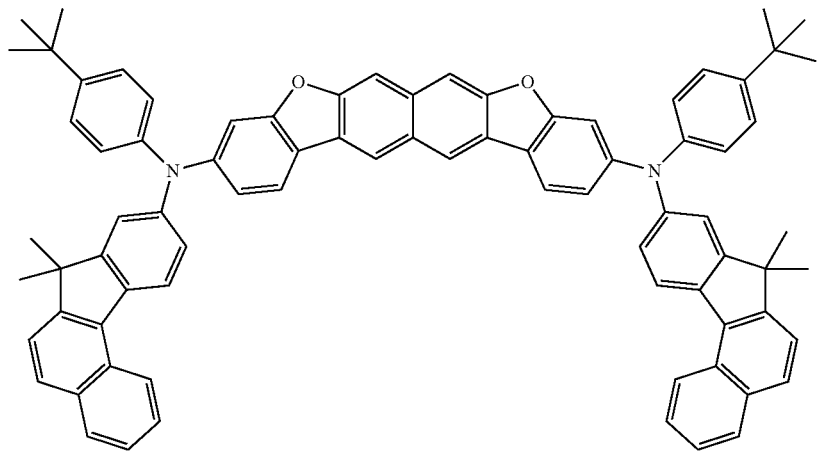
Compound 18
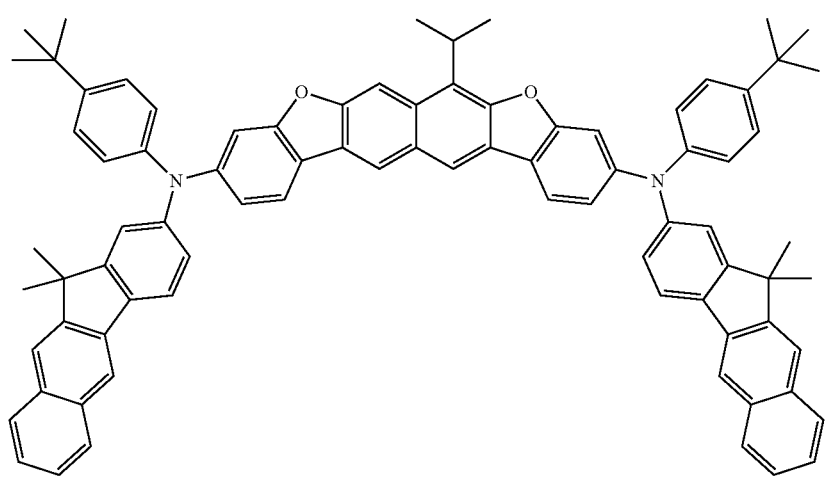
Compound 19
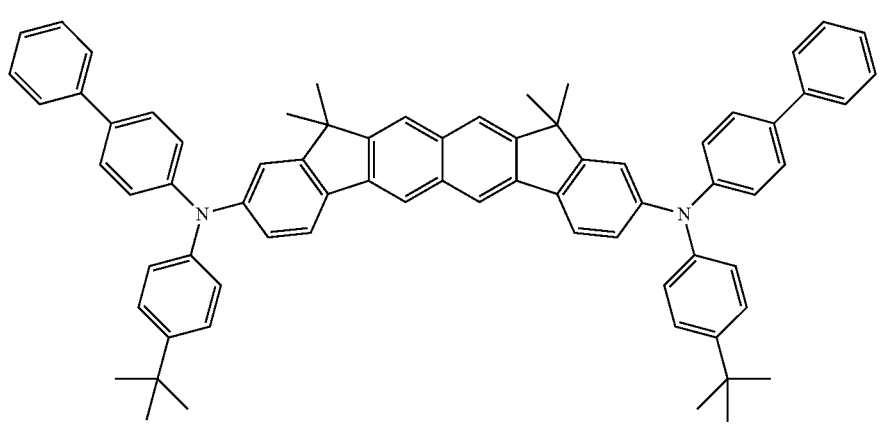

-continued
Compound 20
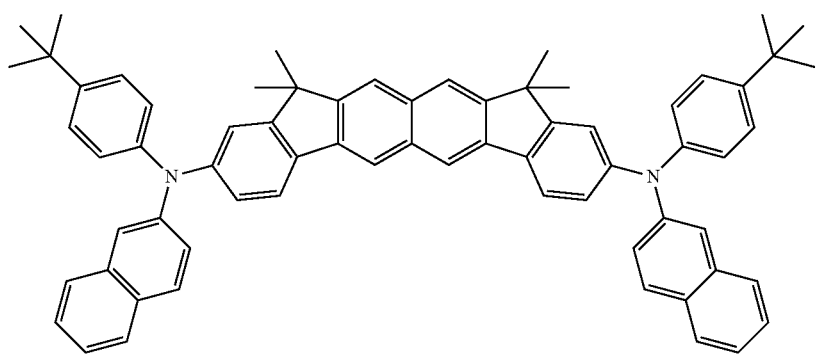
Compound 21
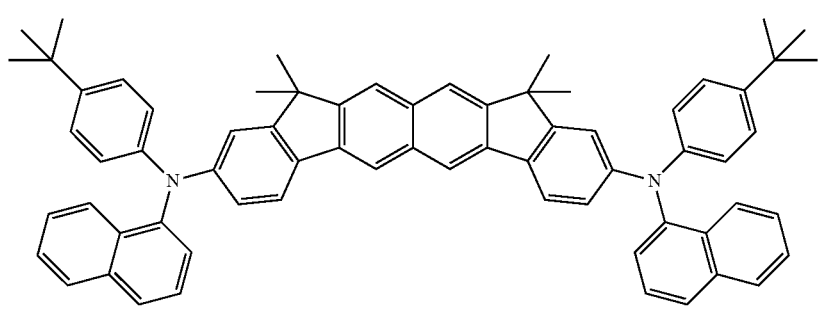
Compound 22
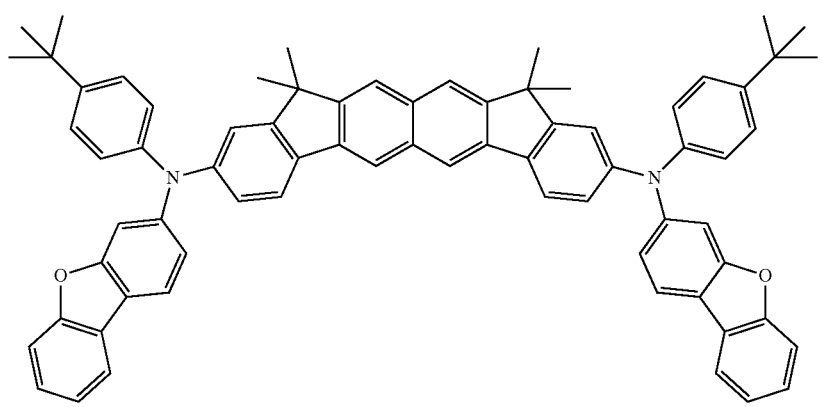
Compound 23
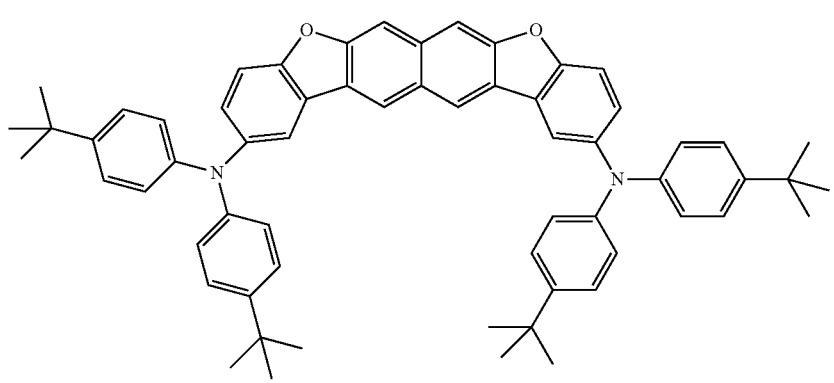

-continued
Compound 24
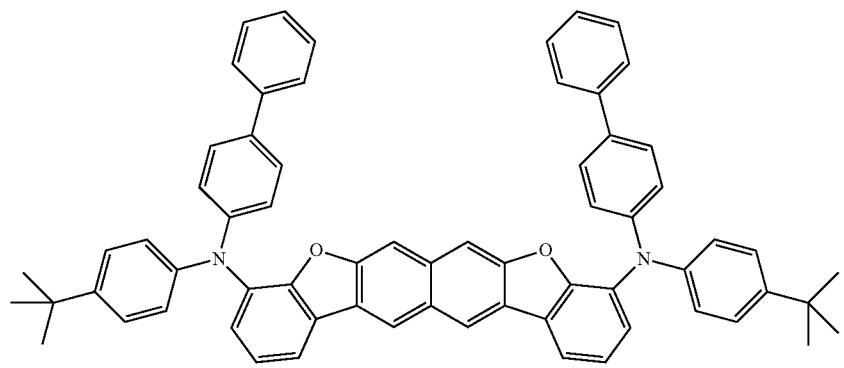
Compound 25
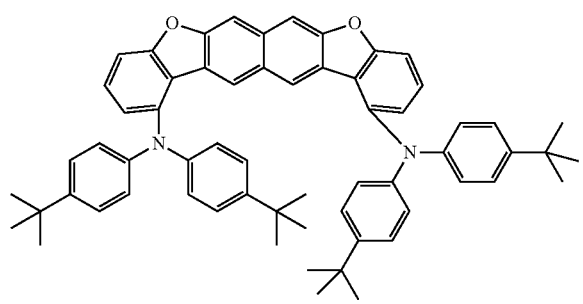
Compound 26
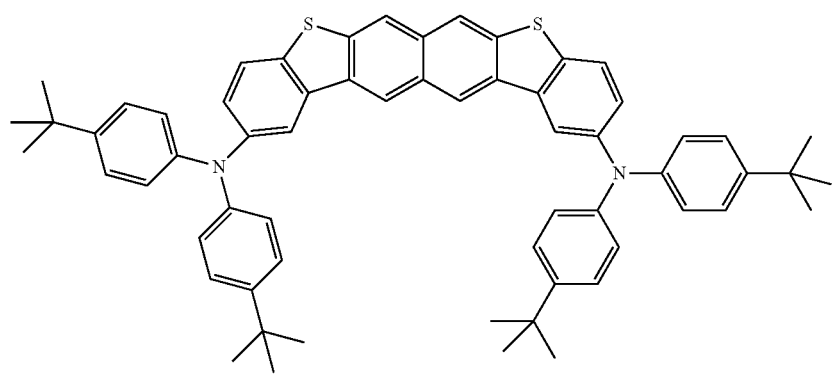
Compound 27
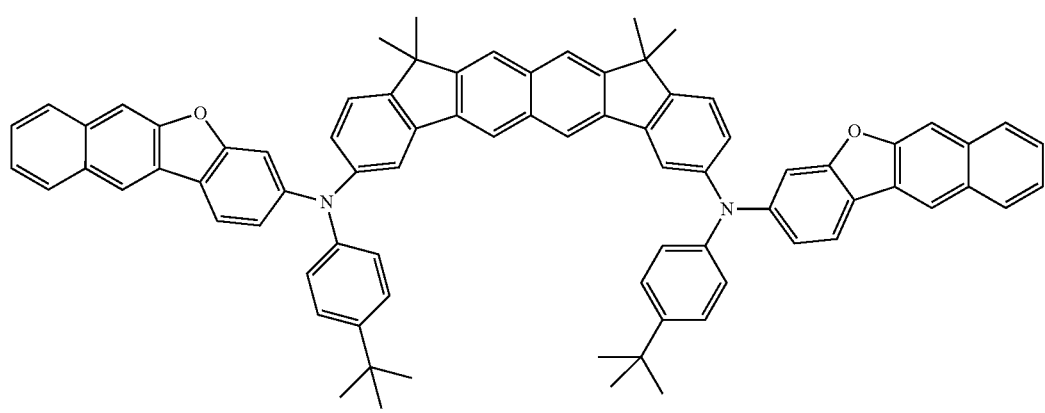

Compound 28
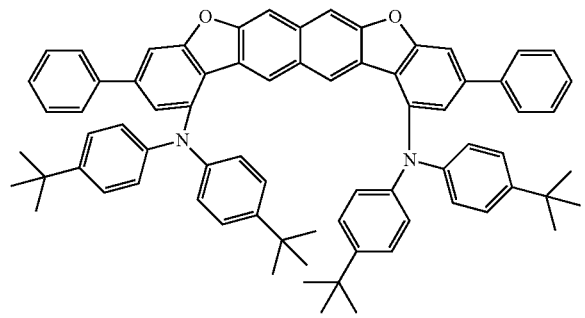
Compound 29
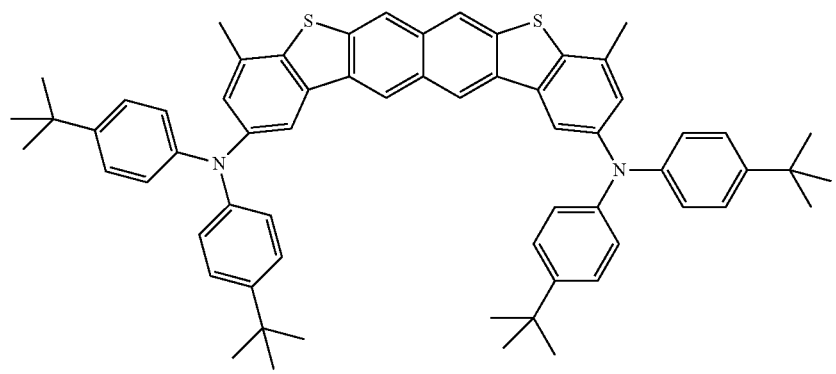
Compound 30
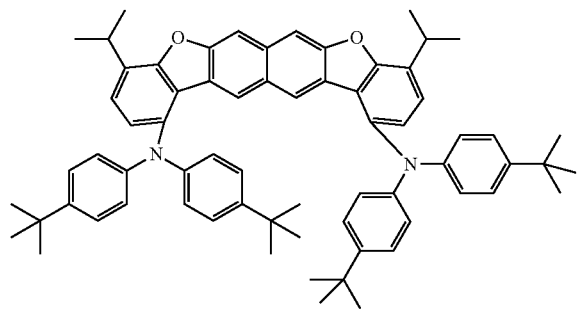
Compound 31
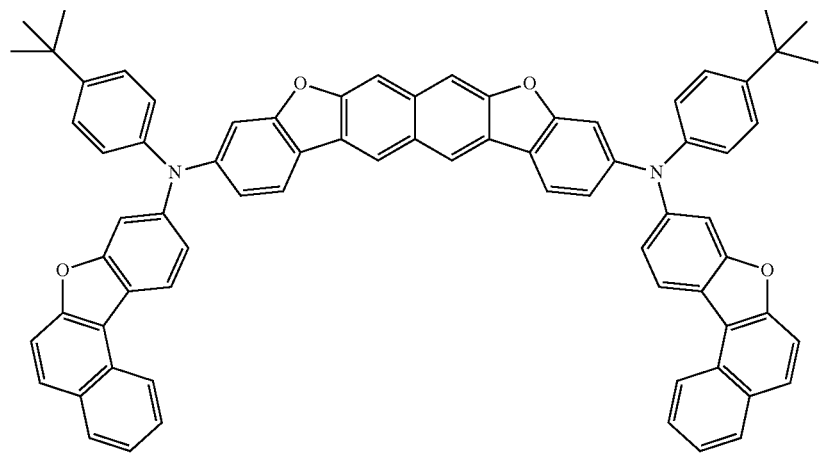

-continued
Compound 32
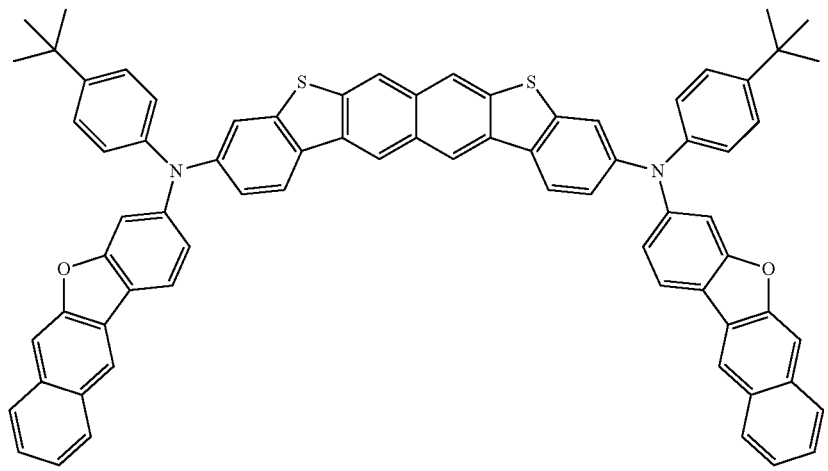
Compound 33
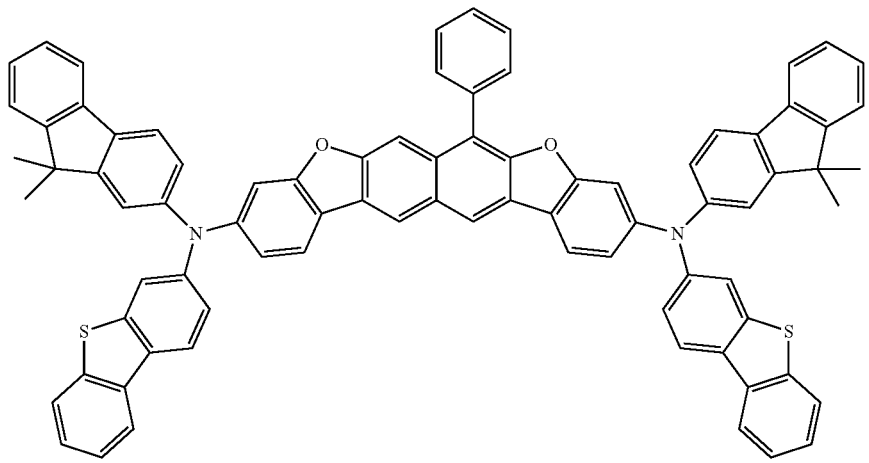
Compound 34
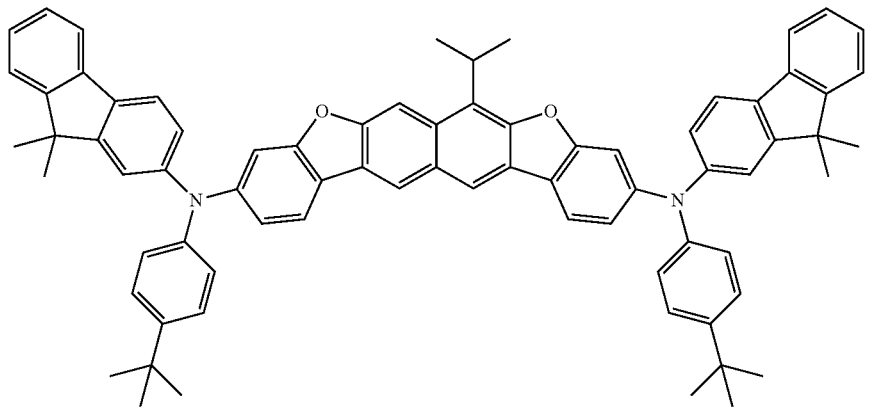

-continued
Compound 35
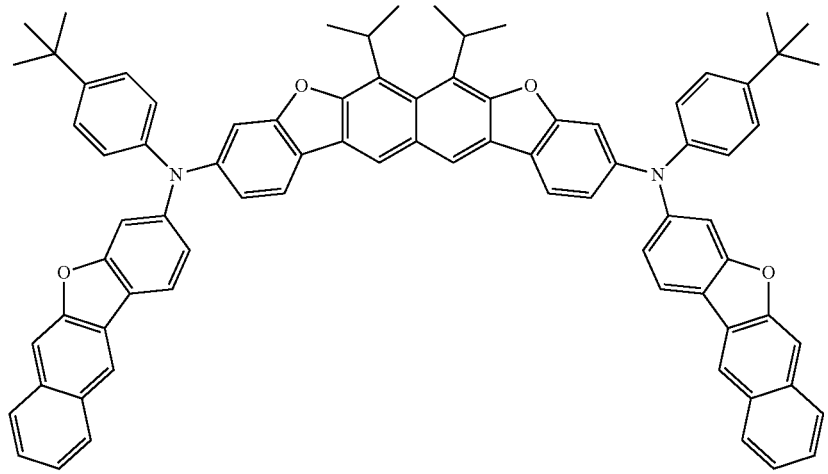
Compound 36
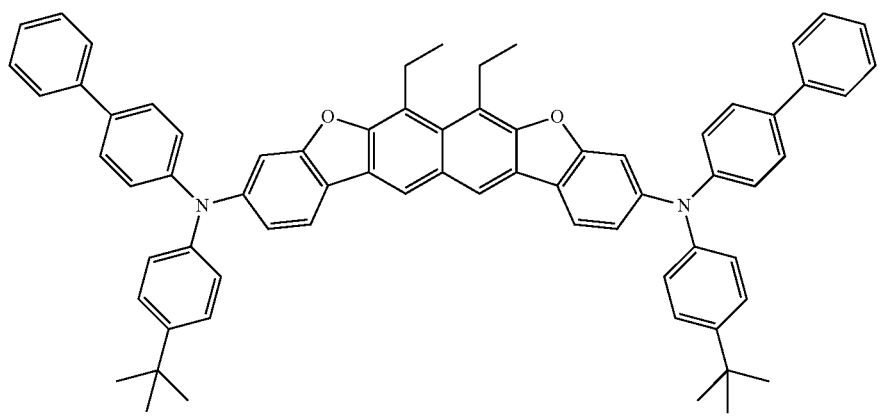
Compound 37
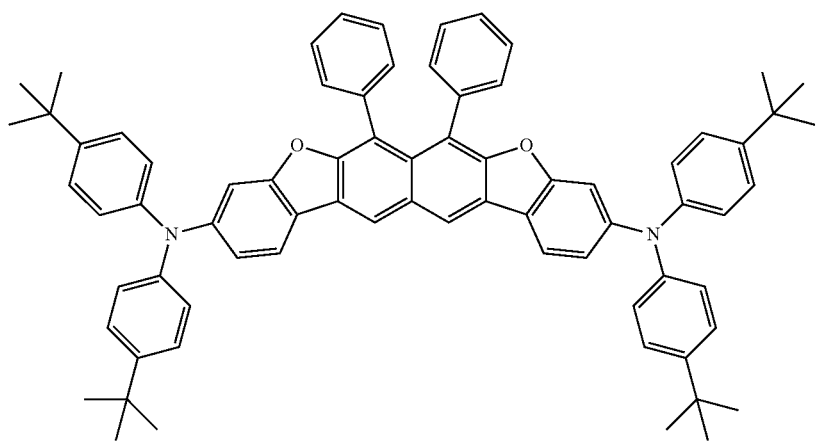

-continued
Compound 38
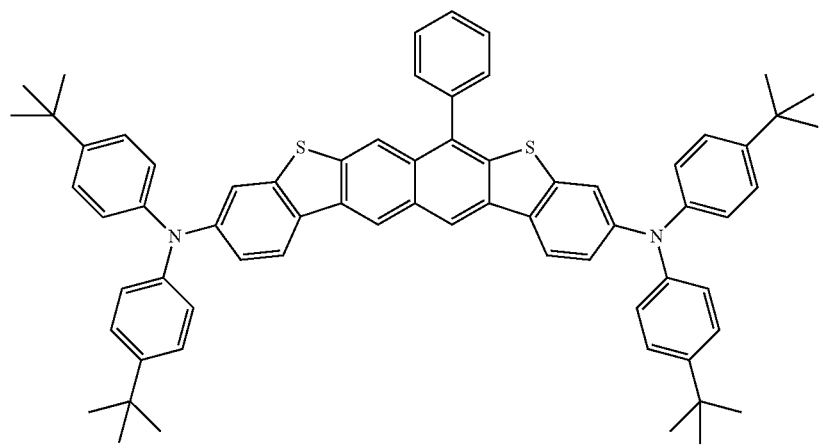
Compound 39
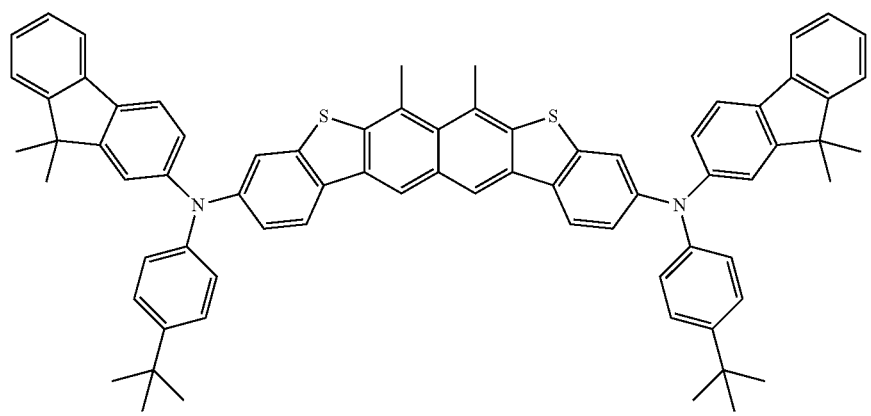
Compound 40
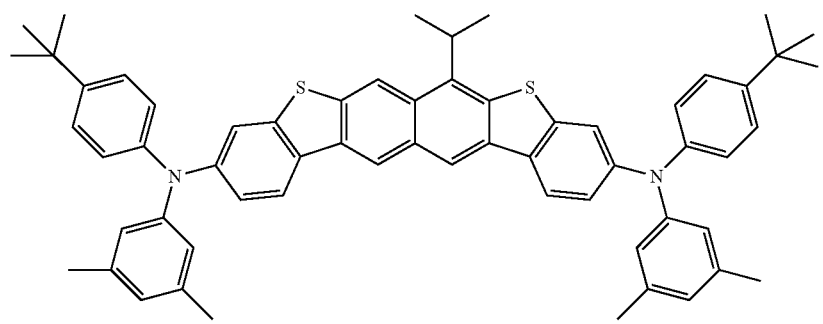
Compound 41
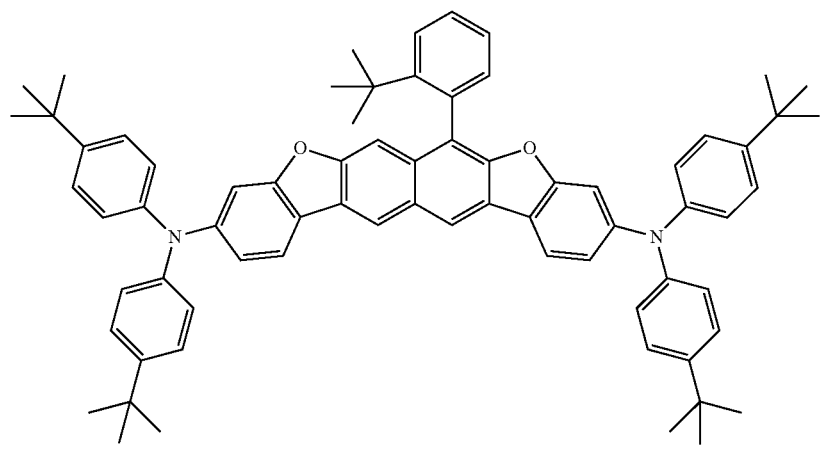

-continued
Compound 42
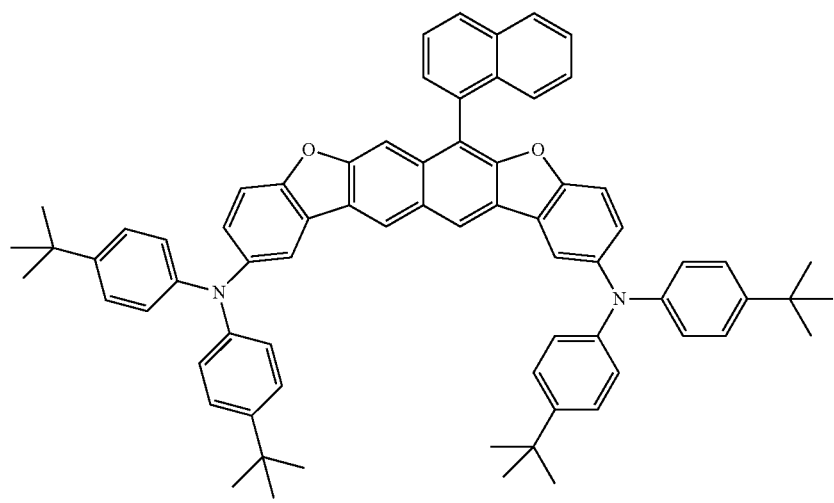
Compound 43
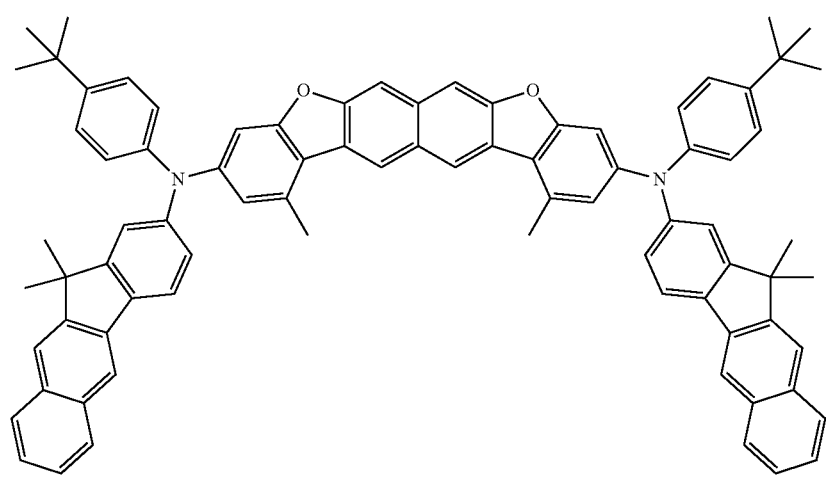
Compound 44
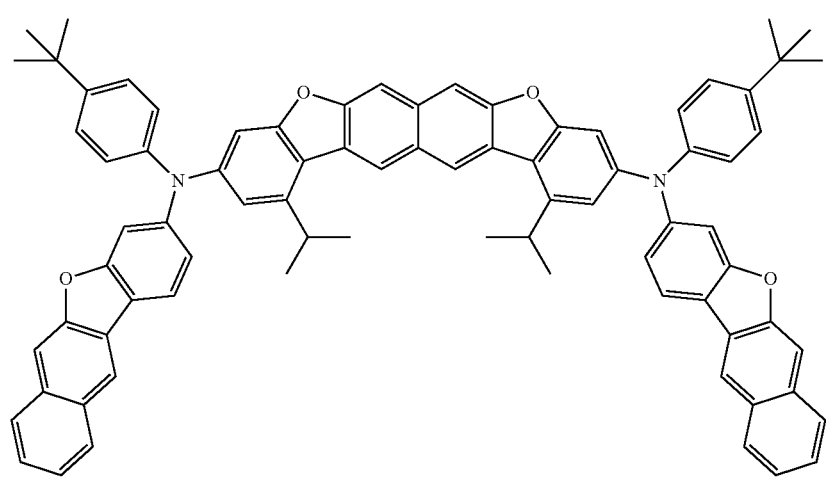

Compound 45
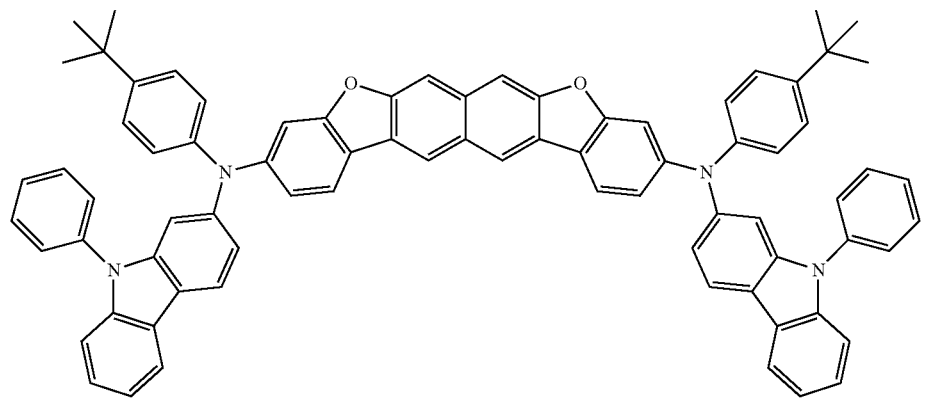
Compound 46
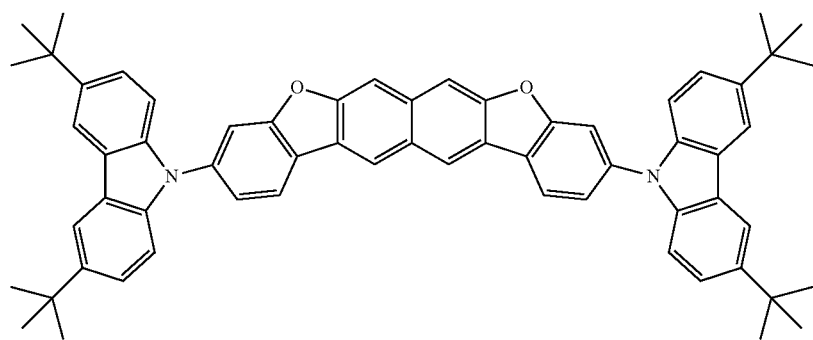
Compound 47
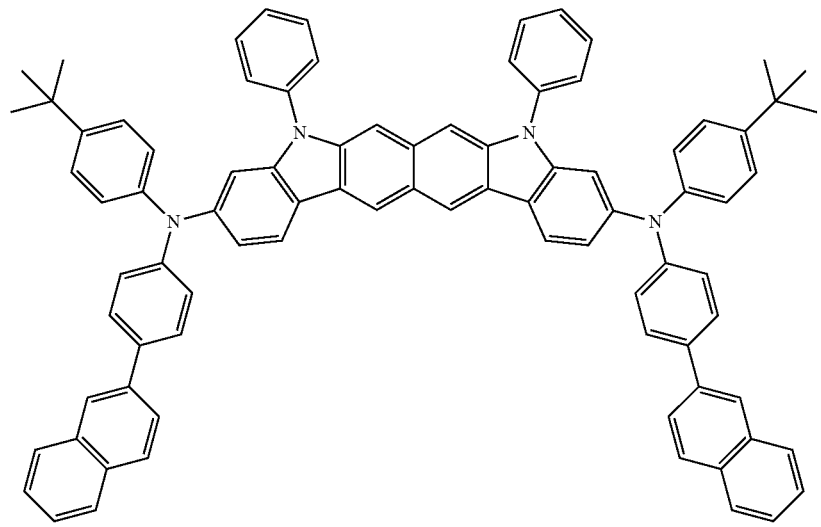

Compound 48
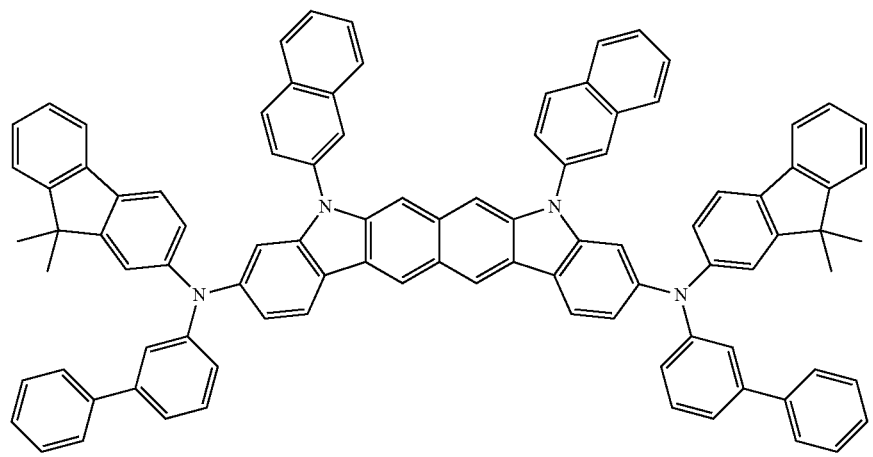
Compound 49
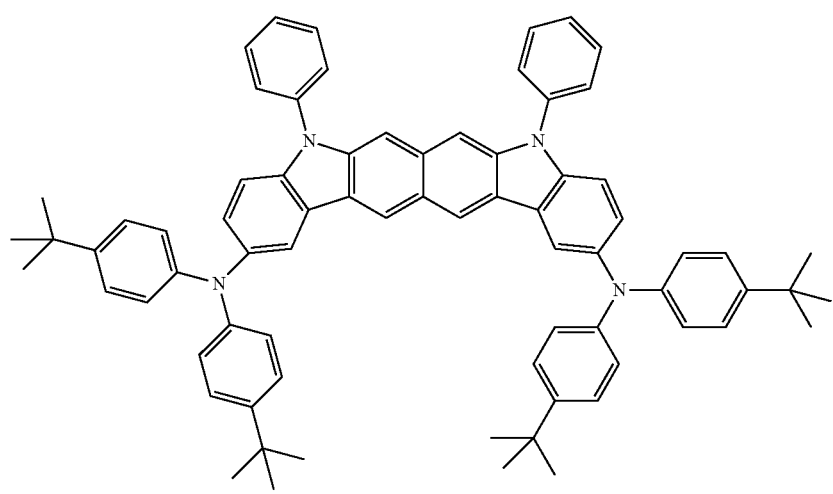
Compound 50
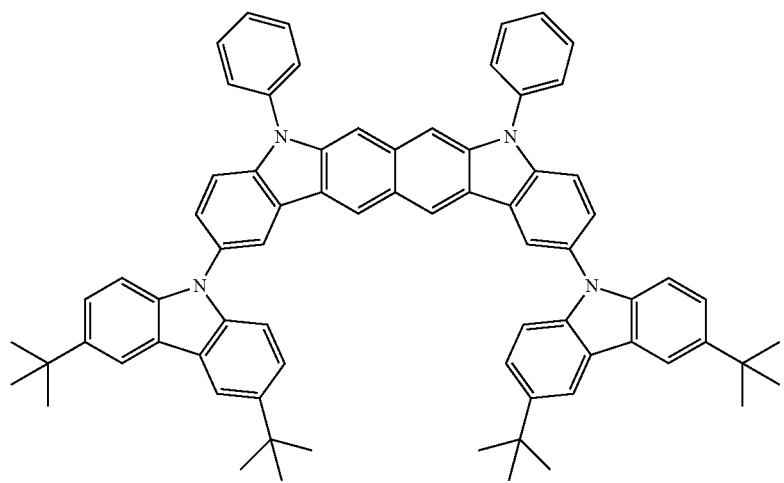

-continued
Compound 51
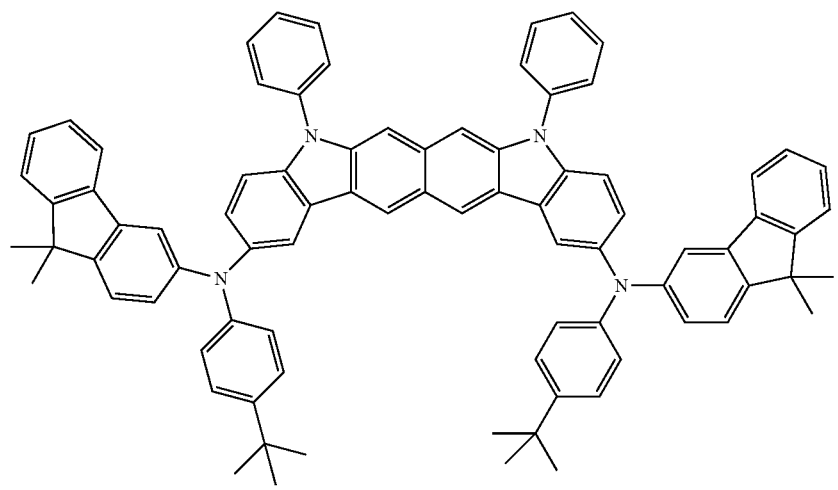
Compound 52
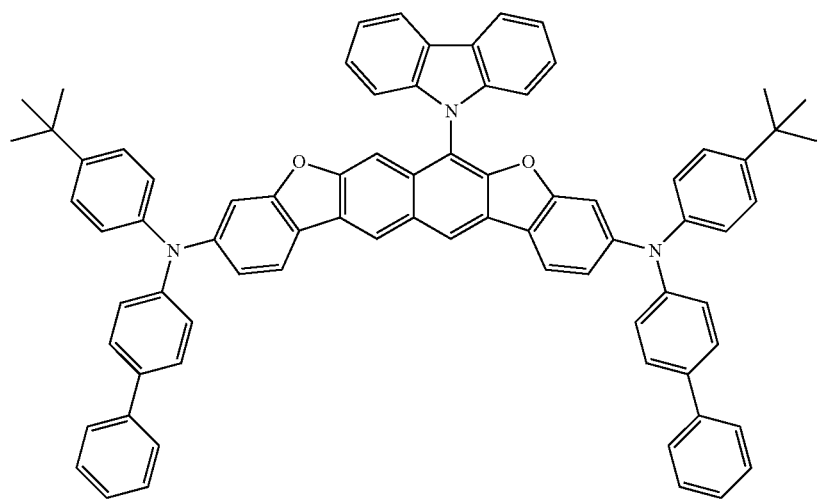
Compound 53
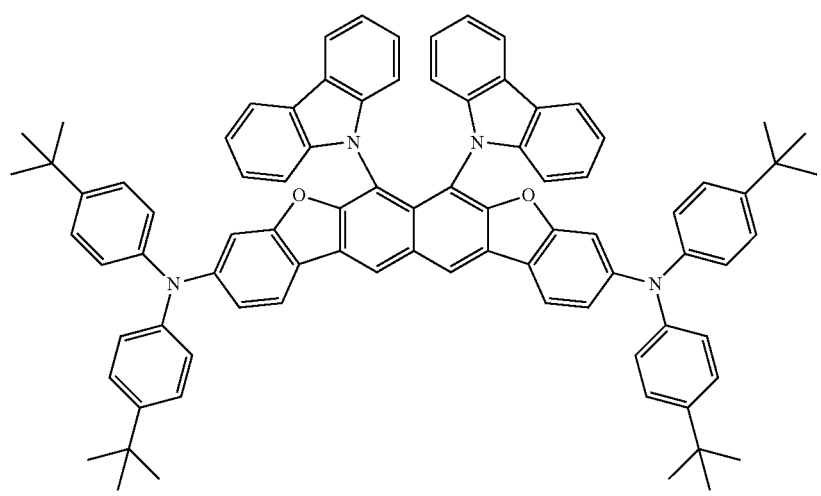

Compound 54
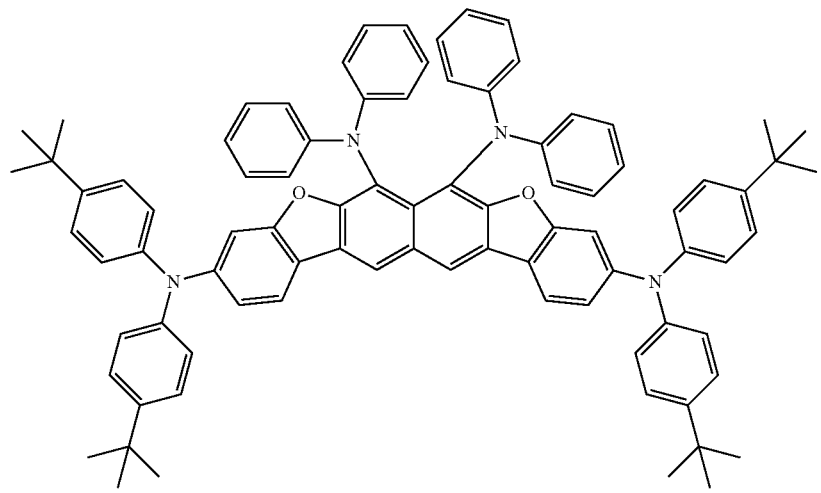
Compound 55
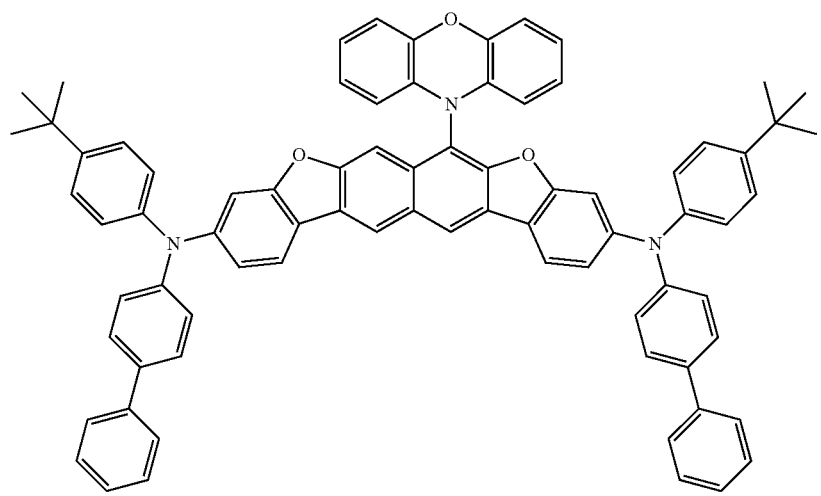
Compound 56
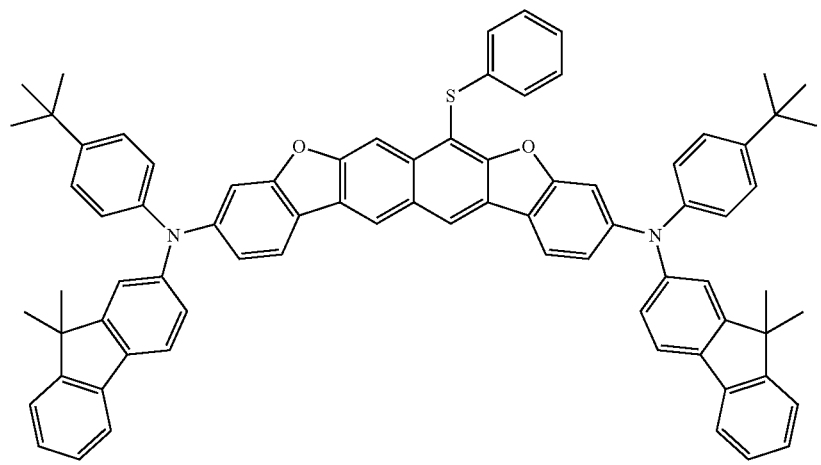

-continued
Compound 57
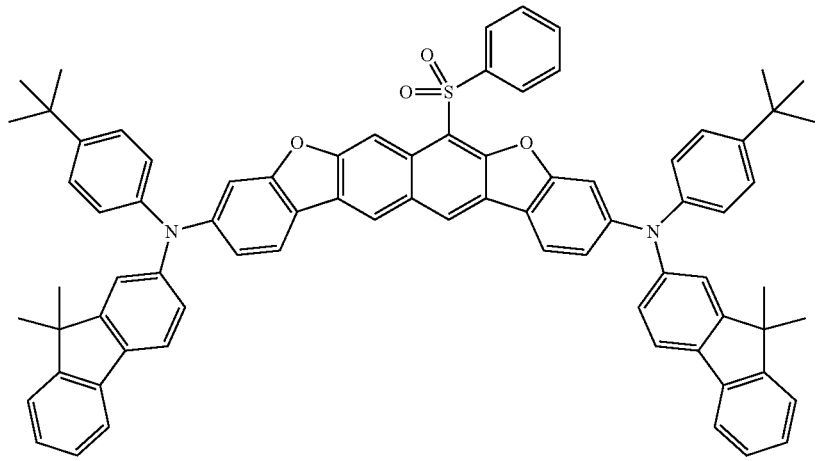
Compound 58
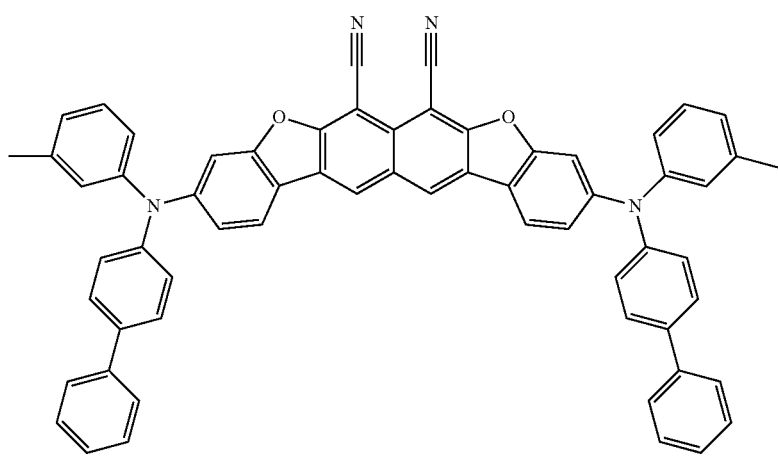
Compound 59
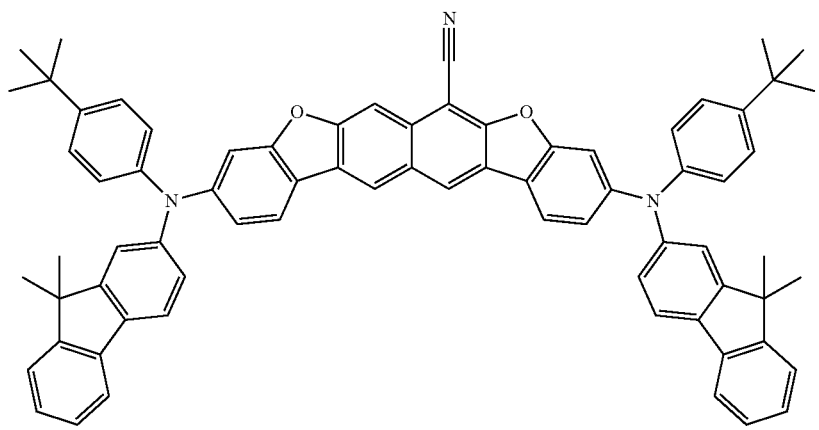

Compound 60
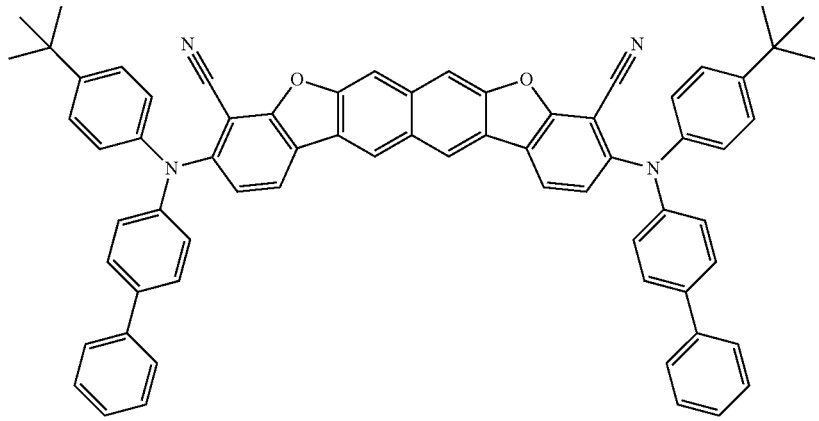
Compound 61
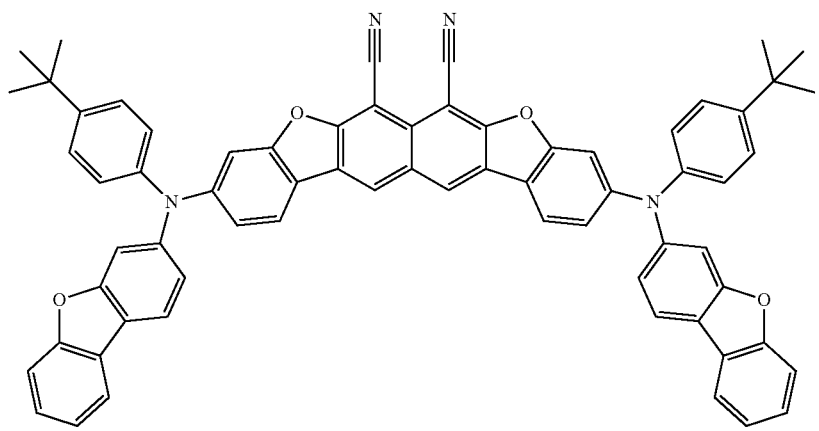
Compound 62
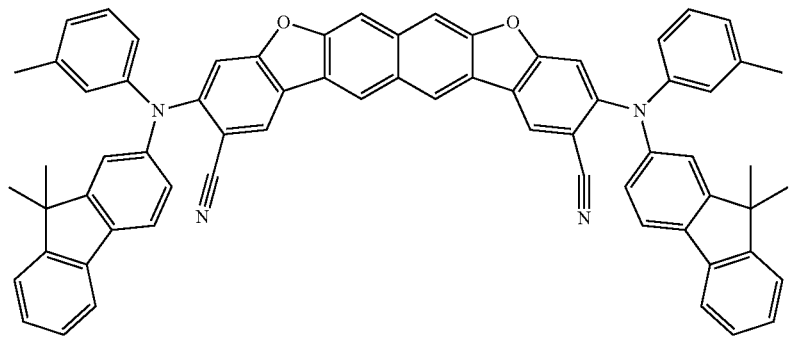
Compound 63
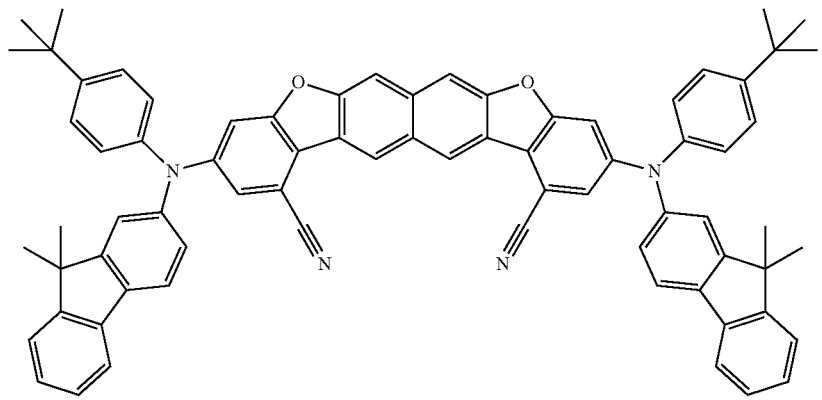

Compound 64
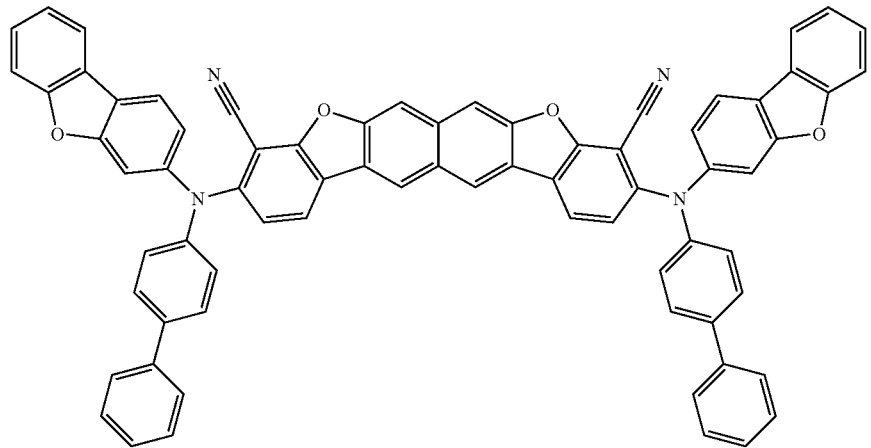
Compound 65
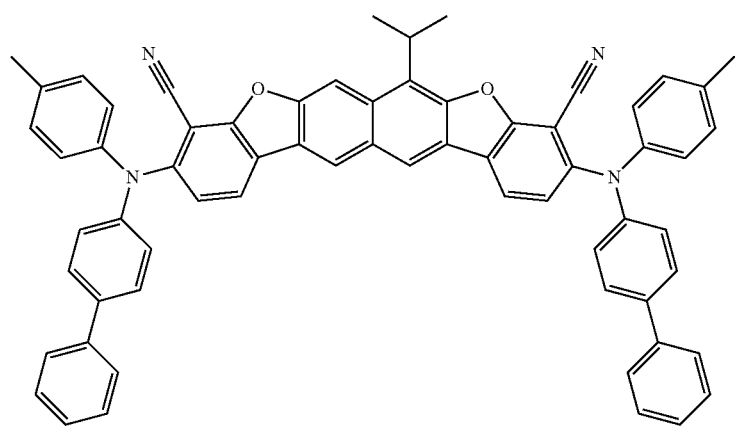
Compound 66
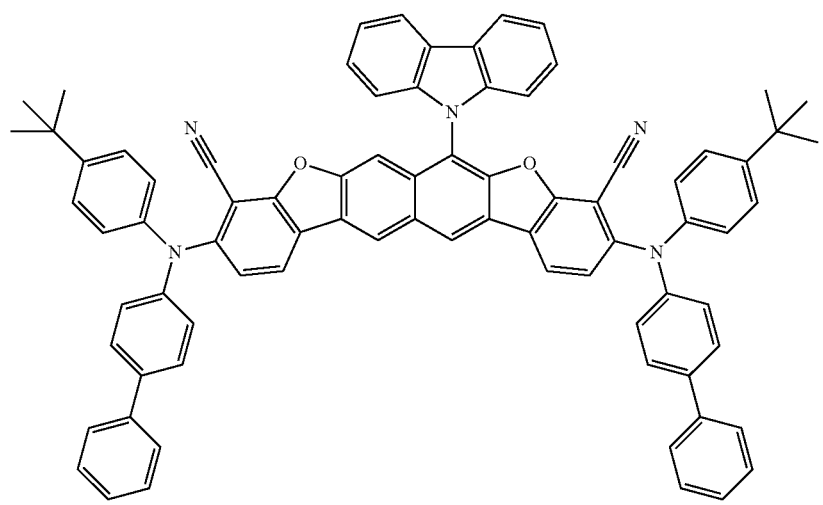

-continued
Compound 67
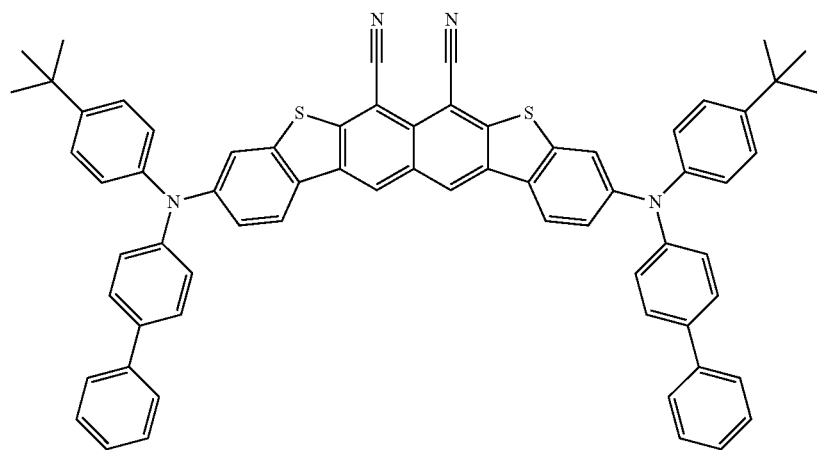
Compound 68
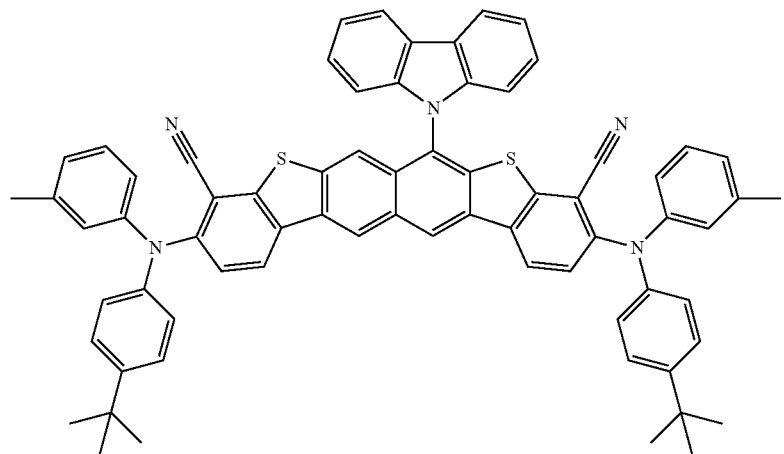
Compound 69
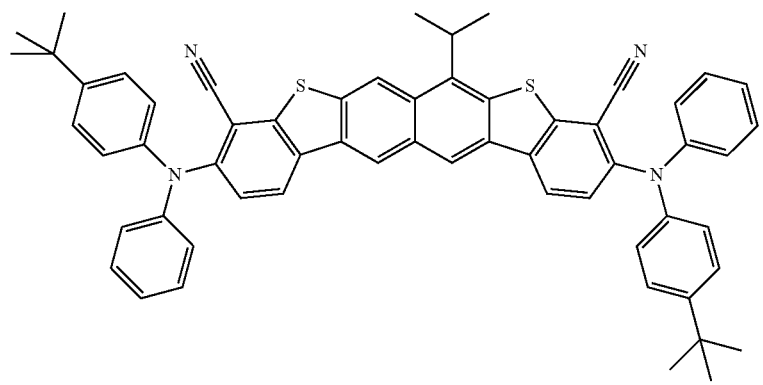

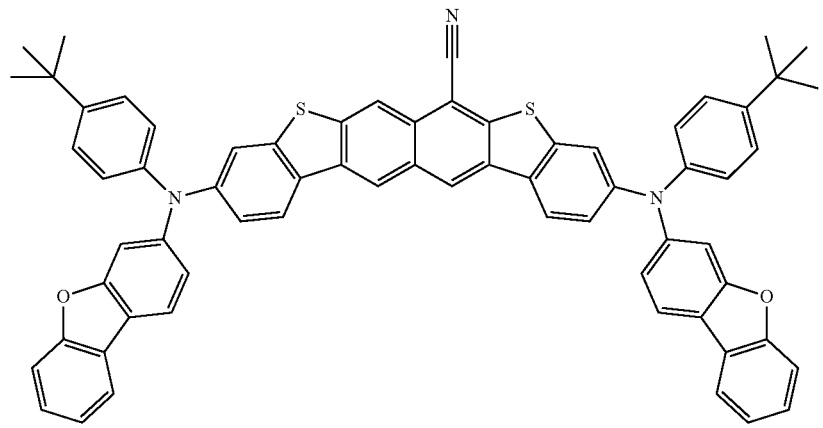
Compound 70
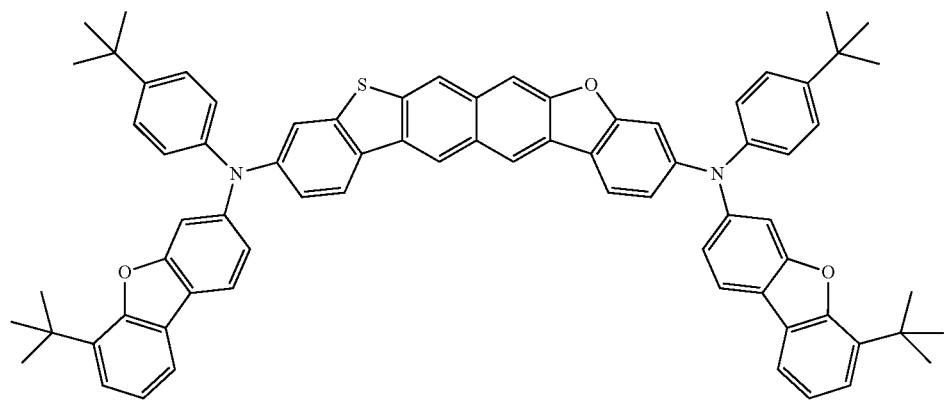
Compound 70
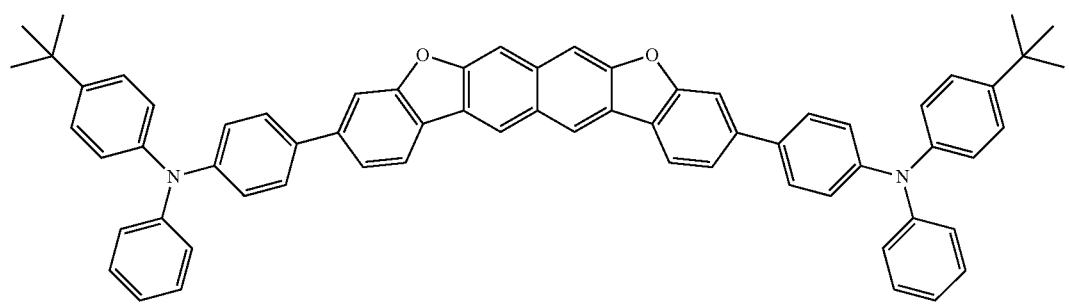
Compound 71

The compound of Chemical Formula 1 according to one embodiment of the present specification can be prepared using a preparation method to describe later.

For example, the compound of Chemical Formula 1 can have its core structure prepared as in the following reaction scheme. Substituents can bond using methods known in the art, and types, positions or the number of the substituents can vary depending on technologies known in the art.

<Reaction scheme>

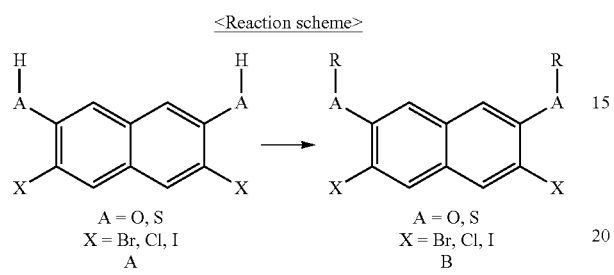

From a 2,7-substituted naphthalene derivative A, B can be synthesized. Herein, R is a protecting substituent formed with alkyl or aryl.

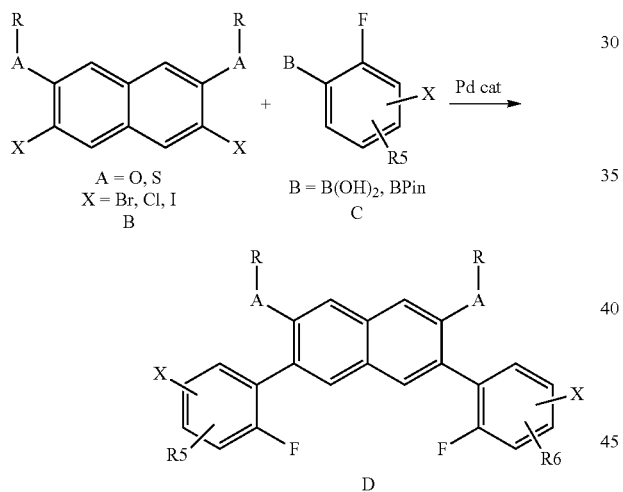

Using obtained B, D can be synthesized through a palladium coupling reaction with a fluoro compound C. Herein, B is a boron functional group, and represents boronic acid or boronic acid alkyl ester.

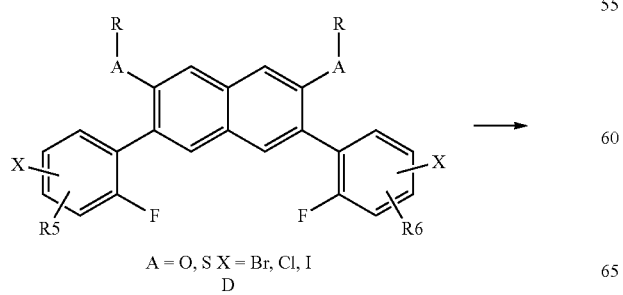

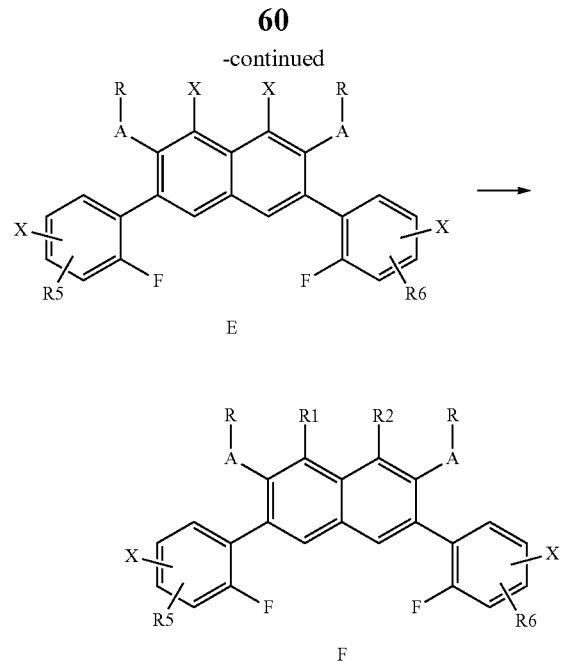

Position 1 or positions 1 and 8 of the obtained naphthalene derivative of D can be selectively halogenated using a halogenation reagent. This can be changed to a target derivative such as alkyl, aryl, oxygen or sulfur using strong bases, Grignard reagents or other proper reagents for nucleophilic substitution to obtain F.

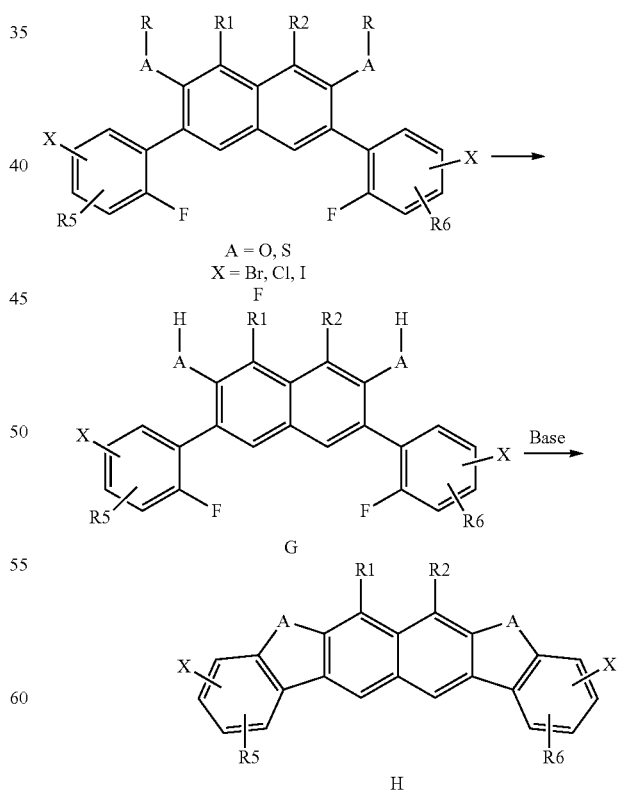

After obtaining G using a proper method of deprotecting F, a ring can be formed under a basic condition to obtain H.

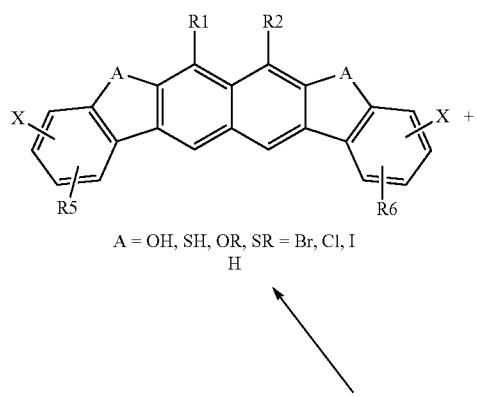

A = OH, SH, OR, SR = Br, Cl, I
H

Expand to avoid overlapping text (SR overlaps with X);
X is defined the same as in all of the preceeding reactions

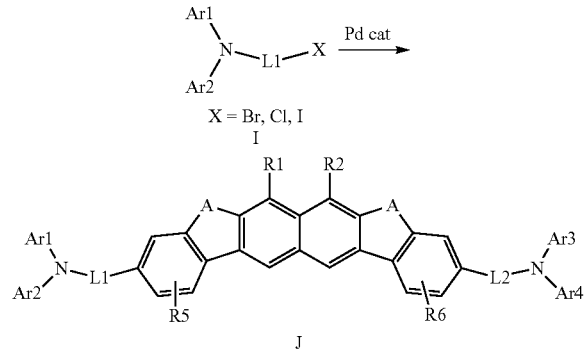

Using obtained H, J can be obtained through a palladium coupling reaction with a proper amine derivative I. In order to obtain high purity, obtained J can be purified using a column chromatography method, a recrystallization method or a sublimation purification method.

The described general method describes a most typical method, and when the reaction is readily performed, the intermediate reaction can be skipped in the synthesis. An example thereof can comprise a direct palladium coupling reaction with I without a protecting reaction from A to B.

The reaction schemes describe a synthesis process for one example of the compound of Chemical Formula 1 of the present specification, and through substituent bonding methods and reaction schemes known in the art, various types of compounds of Chemical Formula 1 can be synthesized.

In the reaction schemes, L1, L2, Ar1 to Ar4, R1, R2, R5 and R6 have the same definitions as in Chemical Formula 1 described above.

In the present disclosure, compounds having various energy band gaps can be synthesized by introducing various substituents to the core structure as above. In addition, HOMO and LUMO energy levels of the compound can also be adjusted in the present disclosure by introducing various substituents to the core structure having a structure as above.

In addition, by introducing various substituents to the core structure having a structure as above, compounds having unique properties of the introduced substituents can be synthesized. For example, by introducing substituents often used as a hole injection layer material, a material for hole transfer, a light emitting layer material and an electron transfer layer material used when manufacturing an organic light emitting device to the core structure, materials satisfying conditions required for each organic material layer can be synthesized.

In addition, an organic light emitting device according to the present disclosure comprises a first electrode; a second electrode provided opposite to the first electrode; and one or more organic material layers provided between the first electrode and the second electrode, wherein one or more layers of the organic material layers comprise the compound of Chemical Formula 1 described above.

According to one embodiment of the present specification, the organic material layer comprises a light emitting layer, one or more layers of the organic material layers comprise the above-described compound, and the light emitting layer can comprise a compound of Chemical Formula 1A.

[Chemical Formula 1A]

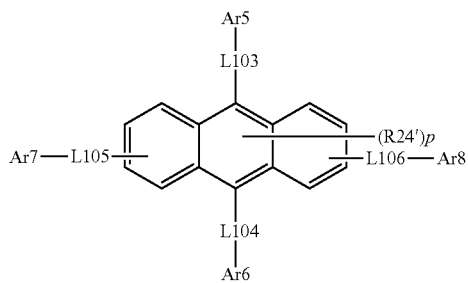

In Chemical Formula 1A:

L103 to L106 are the same as or different from each other, and each independently is a direct bond, a substituted or unsubstituted arylene group, or a substituted or unsubstituted heteroarylene group;

Ar5 to Ar8 are the same as or different from each other, and each independently is hydrogen, a substituted or unsubstituted aryl group, or a substituted or unsubstituted heteroaryl group;

R24's are the same as or different from each other, and each independently is hydrogen, deuterium, a halogen group, a nitrile group, a nitro group, a substituted or unsubstituted alkyl group, a substituted or unsubstituted cycloalkyl group, a substituted or unsubstituted silyl group, a substituted or unsubstituted phosphine oxide group, a substituted or unsubstituted aryl group, or a substituted or unsubstituted heteroaryl group;

p is an integer of 0 to 6; and when p is 2 or greater, substituents in the parentheses are the same as or different from each other.

In one embodiment of the present specification, L103 to L106 are the same as or different from each other, and each independently is a direct bond, a substituted or unsubstituted arylene group having 6 to 60 carbon atoms, or a substituted or unsubstituted heteroarylene group having 2 to 60 carbon atoms.

In one embodiment of the present specification, L103 to L106 are the same as or different from each other, and each independently is a direct bond, a substituted or unsubstituted arylene group having 6 to 40 carbon atoms, or a substituted or unsubstituted heteroarylene group having 2 to 40 carbon atoms.

According to another embodiment, L103 to L106 are the same as or different from each other, and each independently is a direct bond, a substituted or unsubstituted phenylene group, a substituted or unsubstituted biphenylylene group, a substituted or unsubstituted terphenylene group, a substituted or unsubstituted naphthylene group, a substituted or unsubstituted anthracenylene group, a substituted or unsubstituted phenanthrenylene group, a substituted or unsubstituted triphenylene group, a substituted or unsubstituted fluorenyl group, a substituted or unsubstituted thiophenylene group, a substituted or unsubstituted furanylene group, a substituted or unsubstituted dibenzothiophenylene group, a substituted or unsubstituted dibenzofuranylene group, or a substituted or unsubstituted carbazolylene group.

In another embodiment, L103 to L106 are the same as or different from each other, and each independently is a direct bond, a phenylene group, a biphenylylene group, a terphenylene group, a naphthylene group, an anthracenylene group, a phenanthrenylene group, a triphenylene group, a fluorenyl group unsubstituted or substituted with a methyl group or a phenyl group, a thiophenylene group, a furanylene group, a dibenzothiophenylene group, a dibenzofuranylene group, or a carbazolylene group unsubstituted or substituted with an ethyl group or a phenyl group.

According to another embodiment, L103 to L106 are the same as or different from each other, and can be each independently is a direct bond or is selected from among the following structures:

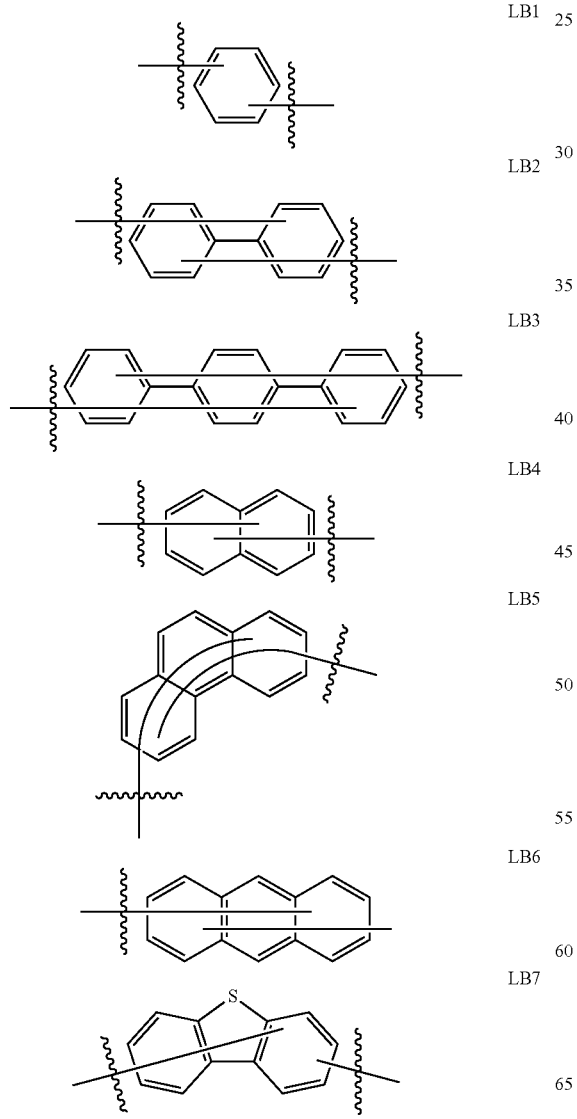

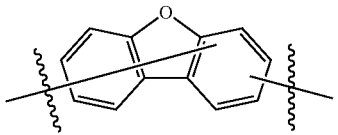

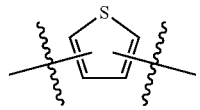

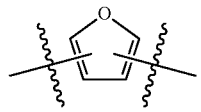

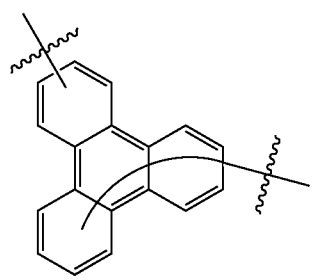

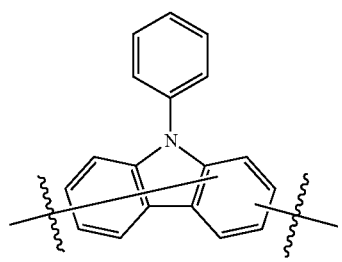

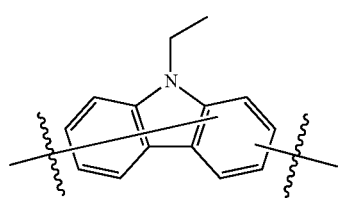

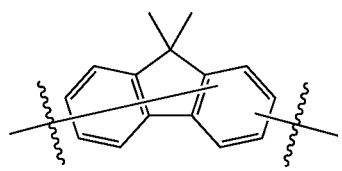

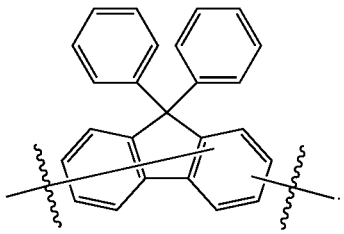

According to one embodiment of the present specification, L103 is a direct bond.

According to one embodiment of the present specification, L104 is a phenylene group.

According to one embodiment of the present specification, L105 and L106 are a direct bond.

In one embodiment of the present specification, R24' is hydrogen, deuterium, a halogen group, a silyl group, a boron group, a substituted or unsubstituted alkyl group, a substituted or unsubstituted cycloalkyl group, a substituted or unsubstituted aryl group, a substituted or unsubstituted alkylamine group, a substituted or unsubstituted aralkylamine group, a substituted or unsubstituted heteroarylamine group, a substituted or unsubstituted arylamine group, a substituted or unsubstituted arylheteroarylamine group, or a substituted or unsubstituted heterocyclic group.

In one embodiment of the present specification, the R24's are the same as or different from each other, and each independently is hydrogen, deuterium, a substituted or unsubstituted alkyl group, a substituted or unsubstituted cycloalkyl group, a substituted or unsubstituted aryl group, or a substituted or unsubstituted heterocyclic group.

In one embodiment of the present specification, the R24's are the same as or different from each other, and each independently is hydrogen, deuterium, a substituted or unsubstituted alkyl group having 1 to 50 carbon atoms, a substituted or unsubstituted cycloalkyl group having 3 to 60 carbon atoms, a substituted or unsubstituted aryl group having 6 to 60 carbon atoms, or a substituted or unsubstituted heterocyclic group having 2 to 40 carbon atoms.

In one embodiment of the present specification, the R24's are the same as or different from each other, and each independently is hydrogen, deuterium, a substituted or unsubstituted alkyl group having 1 to 30 carbon atoms, a substituted or unsubstituted cycloalkyl group having 3 to 30 carbon atoms, a substituted or unsubstituted aryl group having 6 to 30 carbon atoms, or a substituted or unsubstituted heterocyclic group having 2 to 25 carbon atoms.

In another embodiment, R24' is hydrogen.

According to one embodiment of the present specification, p is 0 or 1.

In one embodiment of the present specification, Ar5 to Ar8 are the same as or different from each other, and each independently is hydrogen, a substituted or unsubstituted aryl group having 6 to 60 carbon atoms, or a substituted or unsubstituted heteroaryl group having 2 to 60 carbon atoms.

According to another embodiment, Ar5 to Ar8 are the same as or different from each other, and each independently is hydrogen, an aryl group having 6 to 60 carbon atoms unsubstituted or substituted with an aryl group having 6 to 60 carbon atoms or a heteroaryl group having 2 to 60 carbon atoms, or a heteroaryl group having 2 to 60 carbon atoms unsubstituted or substituted with an aryl group having 60 carbon atoms or a heteroaryl group having 2 to 60 carbon atoms.

In another embodiment, Ar5 to Ar8 are the same as or different from each other, and each independently is hydrogen, a substituted or unsubstituted phenyl group, a substituted or unsubstituted biphenyl group, a substituted or unsubstituted naphthyl group, a substituted or unsubstituted phenanthrene group, a substituted or unsubstituted anthracene group, a substituted or unsubstituted triphenylene group, a substituted or unsubstituted dibenzofuran group, a substituted or unsubstituted naphthobenzofuran group, a substituted or unsubstituted dibenzothiophene group, a substituted or unsubstituted carbazole group, a substituted or unsubstituted fluorene group, a substituted or unsubstituted thiophene group, a substituted or unsubstituted furan group, a substituted or unsubstituted benzothiophene group, a substituted or unsubstituted benzofuran group, a substituted or unsubstituted benzocarbazole group, a substituted or unsubstituted benzofluorene group, a substituted or unsubstituted indolecarbazole group, a substituted or unsubstituted pyridyl group, a substituted or unsubstituted isoquinolyl group, a substituted or unsubstituted quinolyl group, a substituted or unsubstituted quinazolyl group, a substituted or unsubstituted triazine group, a substituted or unsubstituted benzimidazole group, a substituted or unsubstituted benzoxazole group, a substituted or unsubstituted benzothiazole group, a substituted or unsubstituted dihydroacridine group, a substituted or unsubstituted xanthene group, or a substituted or unsubstituted dibenzosilole group.

According to another embodiment, Ar5 to Ar8 are the same as or different from each other, and each independently is hydrogen, a phenyl group, a biphenyl group, a naphthyl group unsubstituted or substituted with an aryl group, a phenanthrene group, an anthracene group, a triphenylene group, a dibenzofuran group unsubstituted or substituted with an aryl group, a naphthobenzofuran group, a dibenzothiophene group unsubstituted or substituted with an aryl group, a carbazole group unsubstituted or substituted with an alkyl group or an aryl group, a fluorene group unsubstituted or substituted with an alkyl group or an aryl group, a thiophene group unsubstituted or substituted with an aryl group, a furan group unsubstituted or substituted with an aryl group, a benzothiophene group, a benzofuran group, a benzocarbazole group unsubstituted or substituted with an alkyl group or an aryl group, a benzofluorene group unsubstituted or substituted with an alkyl group or an aryl group, an indolecarbazole group, a pyridyl group, an isoquinolyl group unsubstituted or substituted with an aryl group, a quinolyl group, a quinazolyl group unsubstituted or substituted with an aryl group, a triazine group unsubstituted or substituted with an aryl group, a benzimidazole group unsubstituted or substituted with an aryl group, a benzoxazole group unsubstituted or substituted with an aryl group, a benzothiazole group unsubstituted or substituted with an aryl group, a dihydroacridine group unsubstituted or substituted with an alkyl group or an aryl group, a xanthene group unsubstituted or substituted with an alkyl group or an aryl group, or a dibenzosilole group unsubstituted or substituted with an alkyl group or an aryl group.

In another embodiment, Ar5 to Ar8 are the same as or different from each other, and each independently is hydrogen, a phenyl group, a biphenyl group, a naphthyl group unsubstituted or substituted with a phenyl group, a phenanthrene group, an anthracene group, a triphenylene group, a dibenzofuran group unsubstituted or substituted with a phenyl group, a naphthobenzofuran group, a dibenzothiophene group unsubstituted or substituted with a phenyl group, a carbazole group unsubstituted or substituted with a methyl group, an ethyl group or a phenyl group, a fluorene group unsubstituted or substituted with a methyl group or a phenyl group, a thiophene group unsubstituted or substituted with a phenyl group, a furan group unsubstituted or substituted with a phenyl group, a benzothiophene group, a benzofuran group, a benzocarbazole group unsubstituted or substituted with a methyl group or a phenyl group, a benzofluorene group unsubstituted or substituted with a methyl group or a phenyl group, an indolecarbazole group, a pyridyl group unsubstituted or substituted with a phenyl group or a naphthyl group, an isoquinolyl group unsubstituted or substituted with a phenyl group, a quinolyl group, a quinazolyl group unsubstituted or substituted with a phenyl group, a triazine group unsubstituted or substituted with a phenyl group, a benzimidazole group unsubstituted or substituted with a phenyl group, a benzoxazole group unsubstituted or substituted with a phenyl group, a benzothiazole group unsubstituted or substituted with a phenyl group, a dihydroacridine group unsubstituted or substituted with a methyl group or a phenyl group, a xanthene group unsubstituted or substituted with a methyl group or a phenyl group, or a dibenzosilole group unsubstituted or substituted with a methyl group or a phenyl group.

In one embodiment of the present specification, Ar5 to Ar8 are the same as or different from each other, and can be each independently is hydrogen, or is selected from among the following structures.

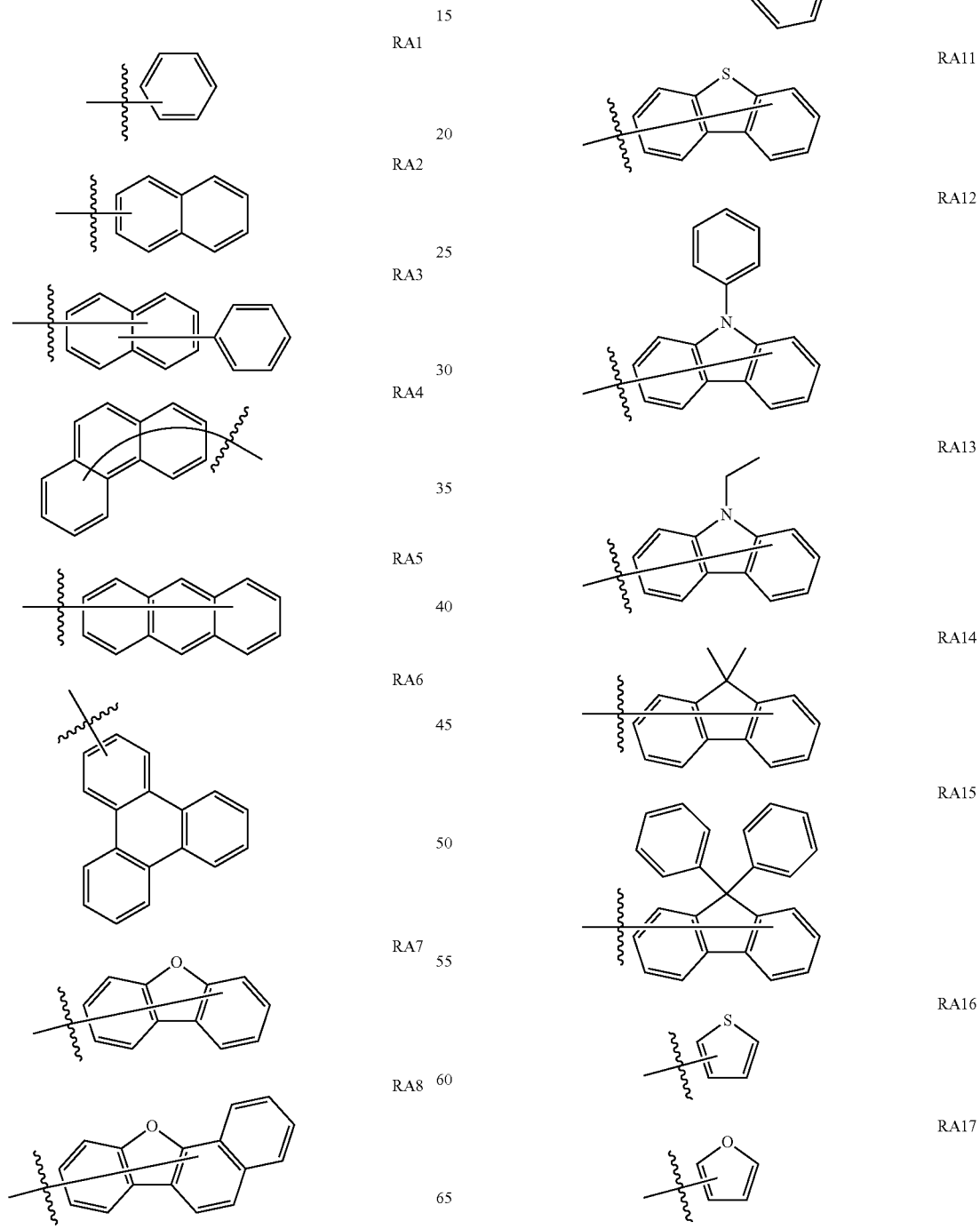

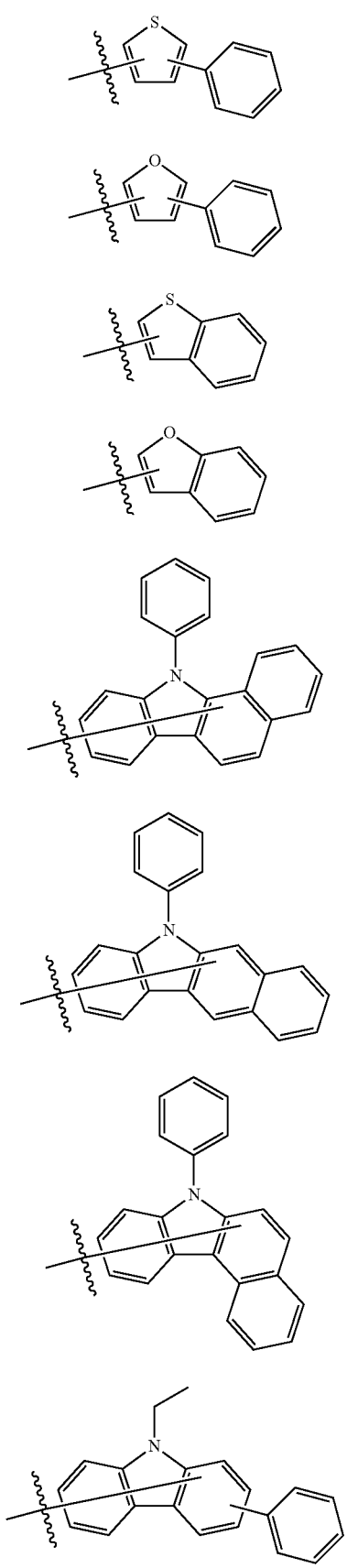
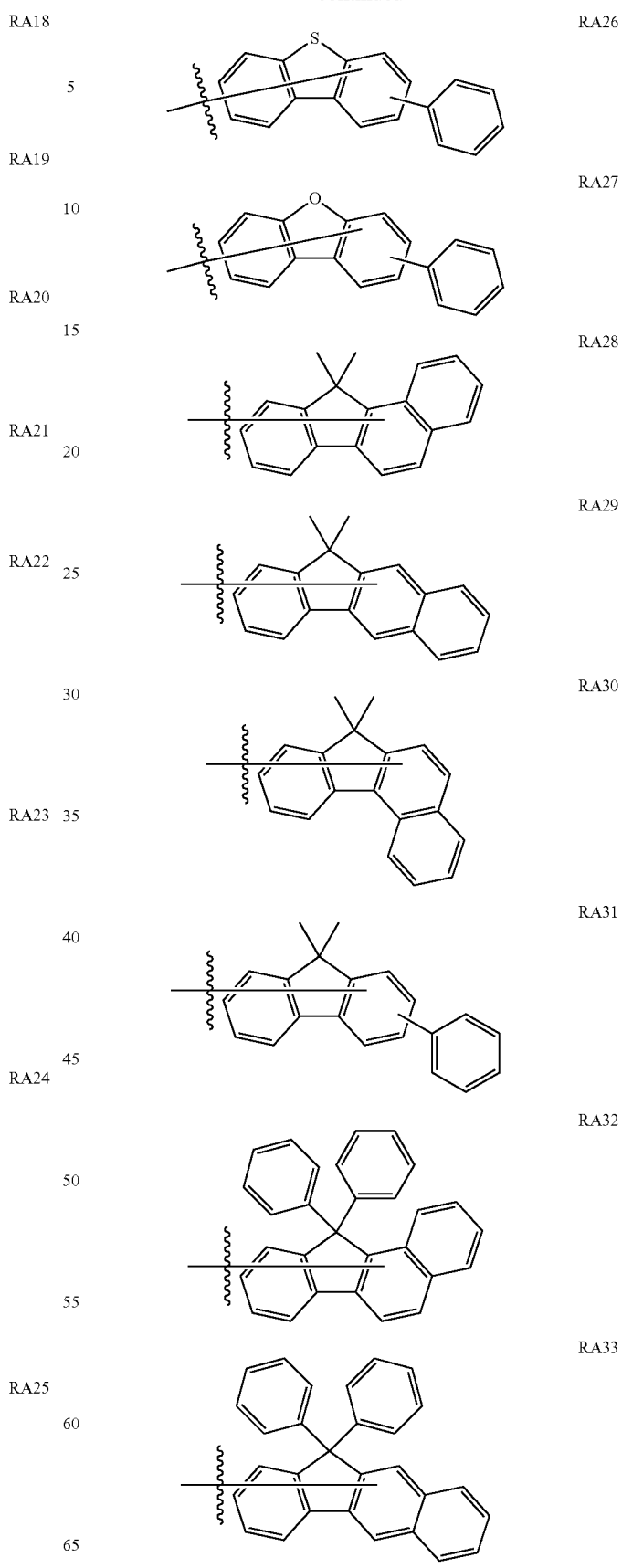

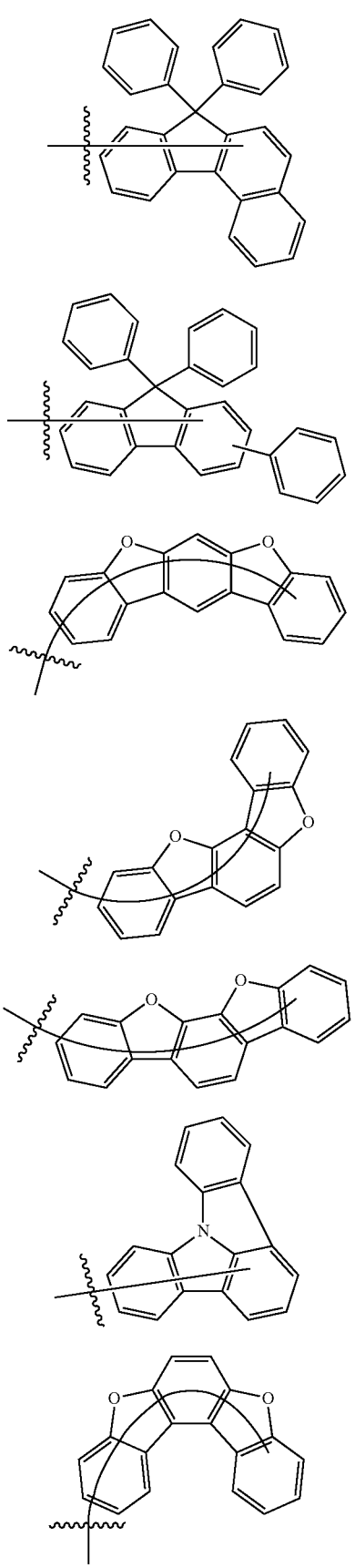
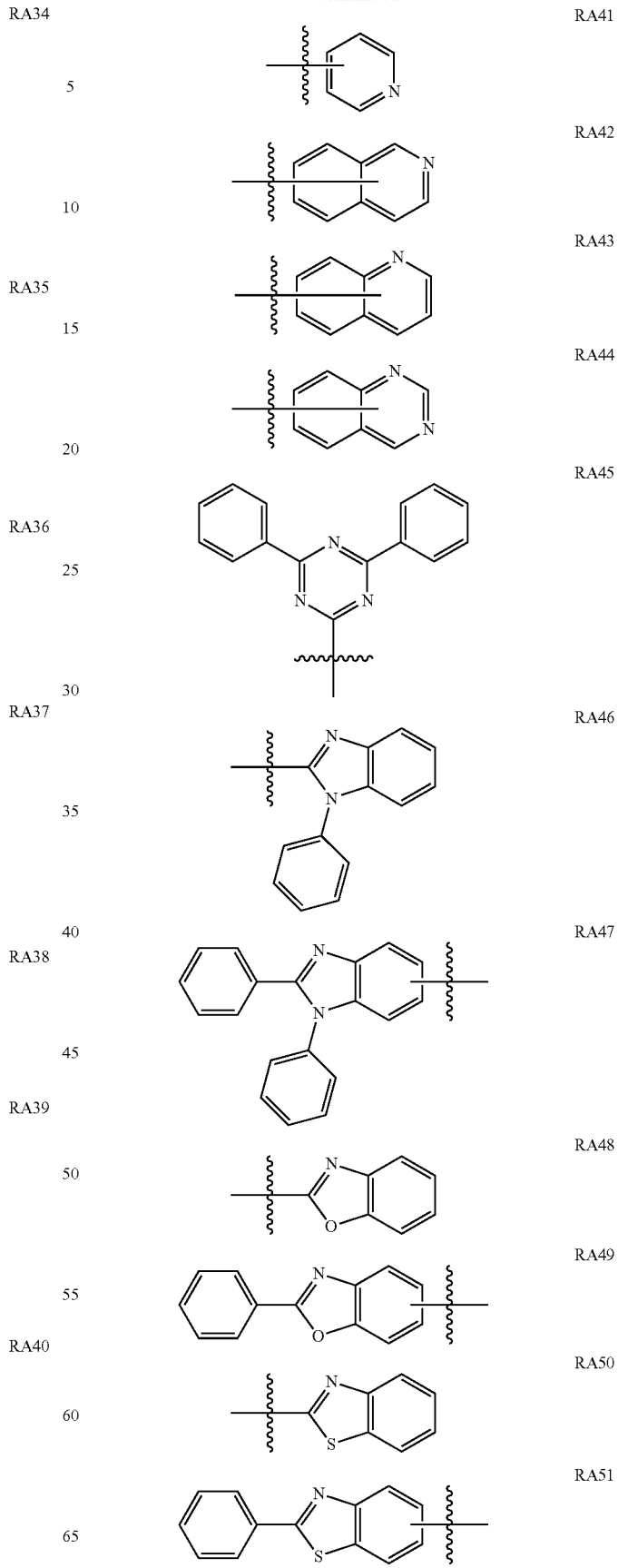

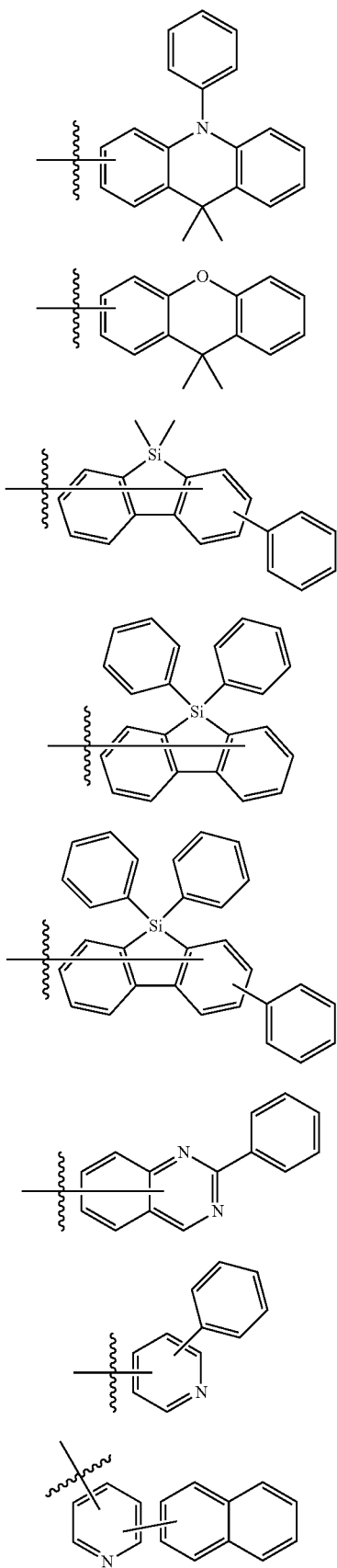

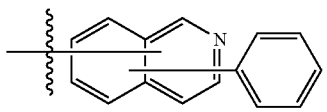

According to one embodiment of the present specification, the organic material layer comprises a light emitting layer, one or more layers of the organic material layers comprise the above-described compound, and the light emitting layer can comprise a compound of the following Chemical Formula 1B.

A structure of the following Chemical Formula 1B can be included as a host material of the light emitting layer among the organic material layers of the organic light emitting device of the present specification:

[Chemical Formula 1B]

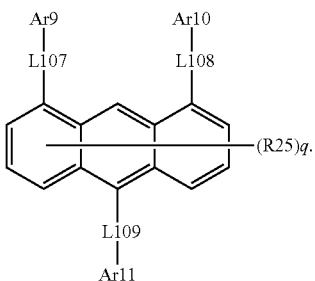

In Chemical Formula 1B,

L107 to L109 are the same as or different from each other, and each independently is a direct bond, a substituted or unsubstituted arylene group, or a substituted or unsubstituted heteroarylene group, Ar9 to Ar11 are the same as or different from each other, and each independently is a substituted or unsubstituted aryl group, or a substituted or unsubstituted heteroaryl group, R25s are the same as or different from each other, and each independently is hydrogen, deuterium, a halogen group, a nitrile group, a nitro group, a substituted or unsubstituted alkyl group, a substituted or unsubstituted cycloalkyl group, a substituted or unsubstituted silyl group, a substituted or unsubstituted phosphine oxide group, a substituted or unsubstituted aryl group, or a substituted or unsubstituted heteroaryl group, q is an integer of 0 to 7, and when q is 2 or greater, substituents in the parentheses are the same as or different from each other.

In one embodiment of the present specification, R25 is hydrogen, deuterium, a halogen group, a silyl group, a boron group, a substituted or unsubstituted alkyl group, a substituted or unsubstituted cycloalkyl group, a substituted or unsubstituted aryl group, a substituted or unsubstituted alkylamine group, a substituted or unsubstituted aralkylamine group, a substituted or unsubstituted heteroarylamine group, a substituted or unsubstituted arylamine group, a substituted or unsubstituted arylheteroarylamine group, or a substituted or unsubstituted heterocyclic group.

In one embodiment of the present specification, R25s are the same as or different from each other, and each independently is hydrogen, deuterium, a substituted or unsubstituted alkyl group, a substituted or unsubstituted cycloalkyl group, a substituted or unsubstituted aryl group, or a substituted or unsubstituted heterocyclic group.

In one embodiment of the present specification, R25s are the same as or different from each other, and each independently is hydrogen, deuterium, a substituted or unsubstituted alkyl group having 1 to 50 carbon atoms, a substituted or unsubstituted cycloalkyl group having 3 to 60 carbon atoms, a substituted or unsubstituted aryl group having 6 to 60 carbon atoms, or a substituted or unsubstituted heterocyclic group having 2 to 40 carbon atoms.

In one embodiment of the present specification, R25s are the same as or different from each other, and each independently is hydrogen, deuterium, a substituted or unsubstituted alkyl group having 1 to 30 carbon atoms, a substituted or unsubstituted cycloalkyl group having 3 to 30 carbon atoms, a substituted or unsubstituted aryl group having 6 to 30 carbon atoms, or a substituted or unsubstituted heterocyclic group having 2 to 25 carbon atoms.

In another embodiment, R25 is hydrogen.

According to one embodiment of the present specification, q is 0 or 1.

In one embodiment of the present specification, L107 to L109 are the same as or different from each other, and each independently is a direct bond, a substituted or unsubstituted arylene group having 6 to 60 carbon atoms, or a substituted or unsubstituted heteroarylene group having 2 to 60 carbon atoms.

In one embodiment of the present specification, L107 to L109 are the same as or different from each other, and each independently is a direct bond, a substituted or unsubstituted arylene group having 6 to 40 carbon atoms, or a substituted or unsubstituted heteroarylene group having 2 to 40 carbon atoms.

According to another embodiment, L107 to L109 are the same as or different from each other, and each independently is a direct bond, a substituted or unsubstituted phenylene group, a substituted or unsubstituted biphenylylene group, a substituted or unsubstituted terphenylene group, a substituted or unsubstituted naphthylene group, a substituted or unsubstituted anthracenylene group, a substituted or unsubstituted phenanthrenylene group, a substituted or unsubstituted triphenylene group, a substituted or unsubstituted fluorenyl group, a substituted or unsubstituted thiophenylene group, a substituted or unsubstituted furanylene group, a substituted or unsubstituted dibenzothiophenylene group, a substituted or unsubstituted dibenzofuranylene group, or a substituted or unsubstituted carbazolylene group.

In another embodiment, L107 to L109 are the same as or different from each other, and each independently is a direct bond, a phenylene group, a biphenylylene group, a terphenylene group, a naphthylene group, an anthracenylene group, a phenanthrenylene group, a triphenylene group, a fluorenyl group unsubstituted or substituted with a methyl group or a phenyl group, a thiophenylene group, a furanylene group, a dibenzothiophenylene group, a dibenzofuranylene group, or a carbazolylene group unsubstituted or substituted with an ethyl group or a phenyl group.

According to another embodiment, L107 to L109 are the same as or different from each other, and can be each is independently a direct bond or is selected from among the following structures:

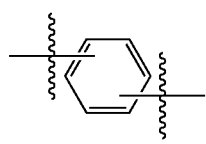
LC1

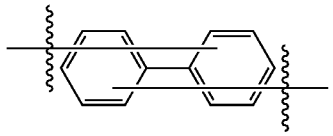
LC2

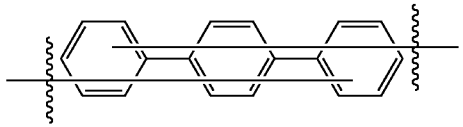
LC3

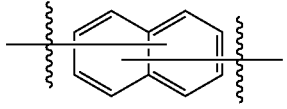
LC4

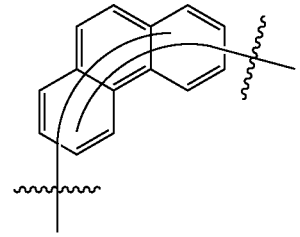
LC5

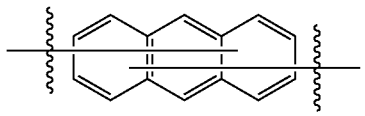
LC6

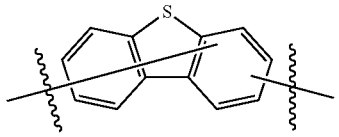
LC7

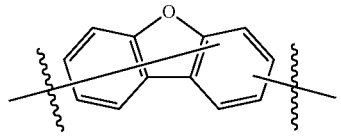
LC8

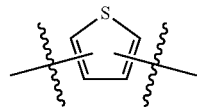
LC9

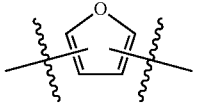
LC10

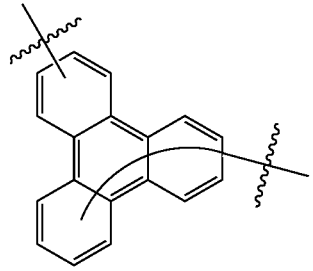
LC11

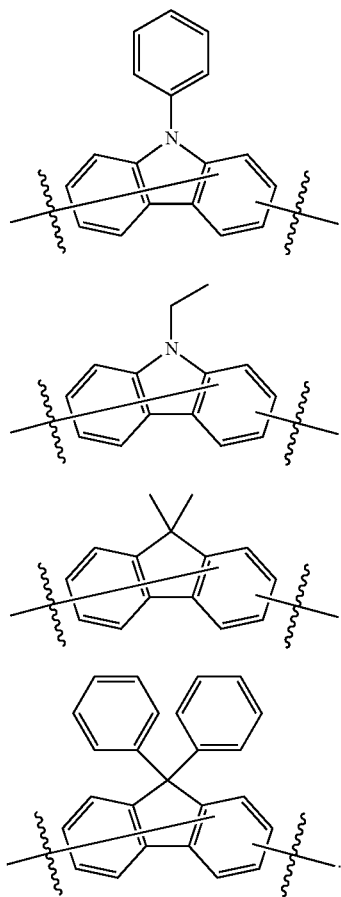

LC12

LC13

LC14

LC15

In one embodiment of the present specification, L107 to L109 are a direct bond.

In one embodiment of the present specification, Ar9 to Ar11 are the same as or different from each other, and each independently is a substituted or unsubstituted aryl group having 6 to 60 carbon atoms or a substituted or unsubstituted heteroaryl group having 2 to 60 carbon atoms.

According to another embodiment, Ar9 to Ar11 are the same as or different from each other, and each independently is an aryl group having 6 to 60 carbon atoms unsubstituted or substituted with an aryl group having 6 to 60 carbon atoms or a heteroaryl group having 2 to 60 carbon atoms, or a heteroaryl group having 2 to 60 carbon atoms unsubstituted or substituted with an aryl group having 60 carbon atoms or a heteroaryl group having 2 to 60 carbon atoms.

In another embodiment, Ar9 to Ar11 are the same as or different from each other, and each independently is a substituted or unsubstituted phenyl group, a substituted or unsubstituted biphenyl group, a substituted or unsubstituted naphthyl group, a substituted or unsubstituted phenanthrene group, a substituted or unsubstituted anthracene group, a substituted or unsubstituted triphenylene group, a substituted or unsubstituted dibenzofuran group, a substituted or unsubstituted naphthobenzofuran group, a substituted or unsubstituted dibenzothiophene group, a substituted or unsubstituted carbazole group, a substituted or unsubstituted fluorene group, a substituted or unsubstituted thiophene group, a substituted or unsubstituted furan group, a substituted or unsubstituted benzothiophene group, a substituted or unsubstituted benzofuran group, a substituted or unsubstituted benzocarbazole group, a substituted or unsubstituted benzofluorene group, a substituted or unsubstituted indolecarbazole group, a substituted or unsubstituted pyridyl group, a substituted or unsubstituted isoquinolyl group, a substituted or unsubstituted quinolyl group, a substituted or unsubstituted quinazolyl group, a substituted or unsubstituted triazine group, a substituted or unsubstituted benzimidazole group, a substituted or unsubstituted benzoxazole group, a substituted or unsubstituted benzothiazole group, a substituted or unsubstituted dihydroacridine group, a substituted or unsubstituted xanthene group, or a substituted or unsubstituted dibenzosilole group.

According to another embodiment, Ar9 to Ar11 are the same as or different from each other, and each independently is a phenyl group, a biphenyl group, a naphthyl group unsubstituted or substituted with an aryl group, a phenanthrene group, an anthracene group, a triphenylene group, a dibenzofuran group unsubstituted or substituted with an aryl group, a naphthobenzofuran group, a dibenzothiophene group unsubstituted or substituted with an aryl group, a carbazole group unsubstituted or substituted with an alkyl group or an aryl group, a fluorene group unsubstituted or substituted with an alkyl group or an aryl group, a thiophene group unsubstituted or substituted with an aryl group, a furan group unsubstituted or substituted with an aryl group, a benzothiophene group, a benzofuran group, a benzocarbazole group unsubstituted or substituted with an alkyl group or an aryl group, a benzofluorene group unsubstituted or substituted with an alkyl group or an aryl group, an indolecarbazole group, a pyridyl group, an isoquinolyl group unsubstituted or substituted with an aryl group, a quinolyl group, a quinazolyl group unsubstituted or substituted with an aryl group, a triazine group unsubstituted or substituted with an aryl group, a benzimidazole group unsubstituted or substituted with an aryl group, a benzoxazole group unsubstituted or substituted with an aryl group, a benzothiazole group unsubstituted or substituted with an aryl group, a dihydroacridine group unsubstituted or substituted with an alkyl group or an aryl group, a xanthene group unsubstituted or substituted with an alkyl group or an aryl group, or a dibenzosilole group unsubstituted or substituted with an alkyl group or an aryl group.

In another embodiment, Ar9 to Ar11 are the same as or different from each other, and each independently is a phenyl group, a biphenyl group, a naphthyl group unsubstituted or substituted with a phenyl group, a phenanthrene group, an anthracene group, a triphenylene group, a dibenzofuran group unsubstituted or substituted with a phenyl group, a naphthobenzofuran group, a dibenzothiophene group unsubstituted or substituted with a phenyl group, a carbazole group unsubstituted or substituted with a methyl group, an ethyl group or a phenyl group, a fluorene group unsubstituted or substituted with a methyl group or a phenyl group, a thiophene group unsubstituted or substituted with a phenyl group, a furan group unsubstituted or substituted with a phenyl group, a benzothiophene group, a benzofuran group, a benzocarbazole group unsubstituted or substituted with a methyl group or a phenyl group, a benzofluorene group unsubstituted or substituted with a methyl group or a phenyl group, an indolecarbazole group, a pyridyl group unsubstituted or substituted with a phenyl group or a naphthyl group, an isoquinolyl group unsubstituted or substituted with a phenyl group, a quinolyl group, a quinazolyl group unsubstituted or substituted with a phenyl group, a triazine group unsubstituted or substituted with a phenyl group, a benzimidazole group unsubstituted or substituted with a phenyl group, a benzoxazole group unsubstituted or substituted with a phenyl group, a benzothiazole group unsubstituted or substituted with a phenyl group, a dihydroacridine group unsubstituted or substituted with a methyl group or a phenyl group, a xanthene group unsubstituted or substituted with a methyl group or a phenyl group, or a dibenzosilole group unsubstituted or substituted with a methyl group or a phenyl group.

In one embodiment of the present specification, Ar9 to Ar11 are the same as or different from each other, and can be each independently selected from among the following structures.

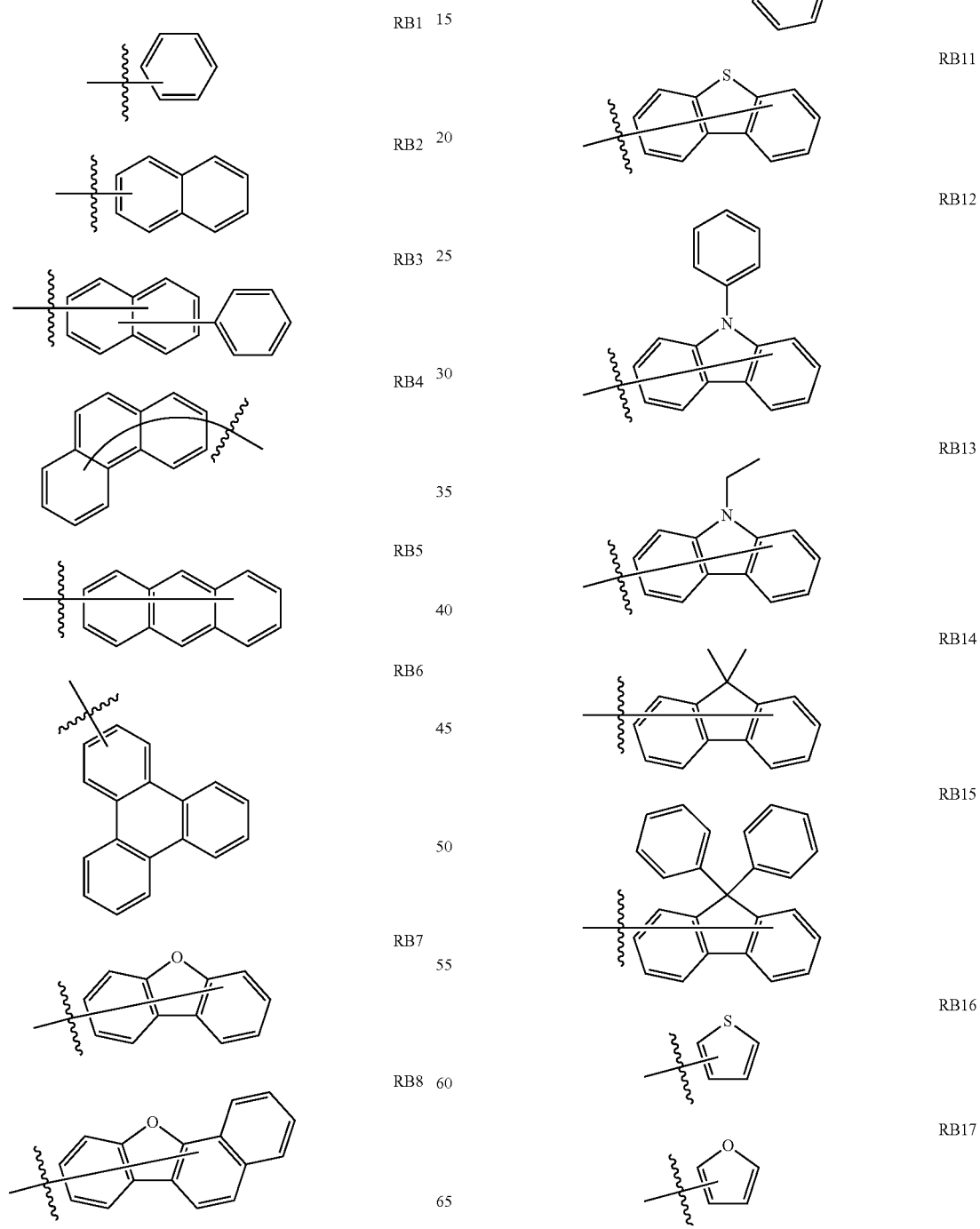

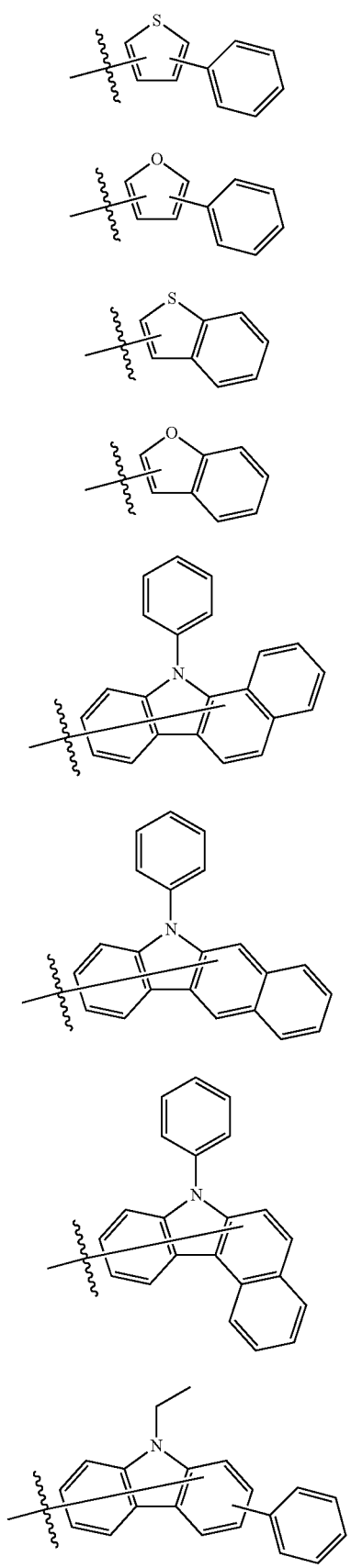
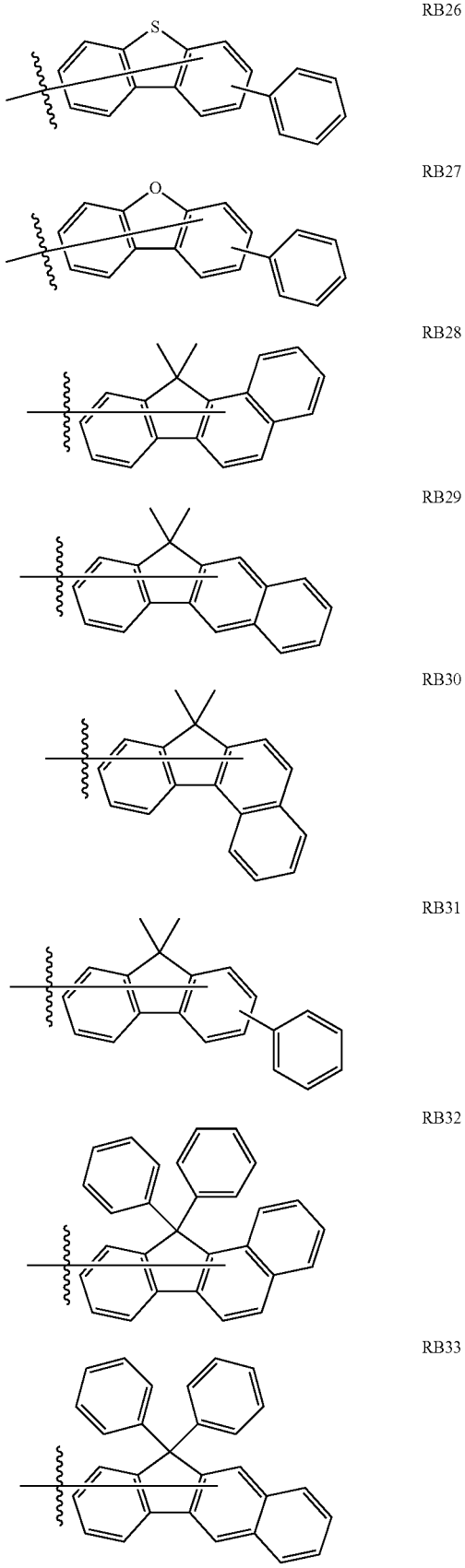

-continued
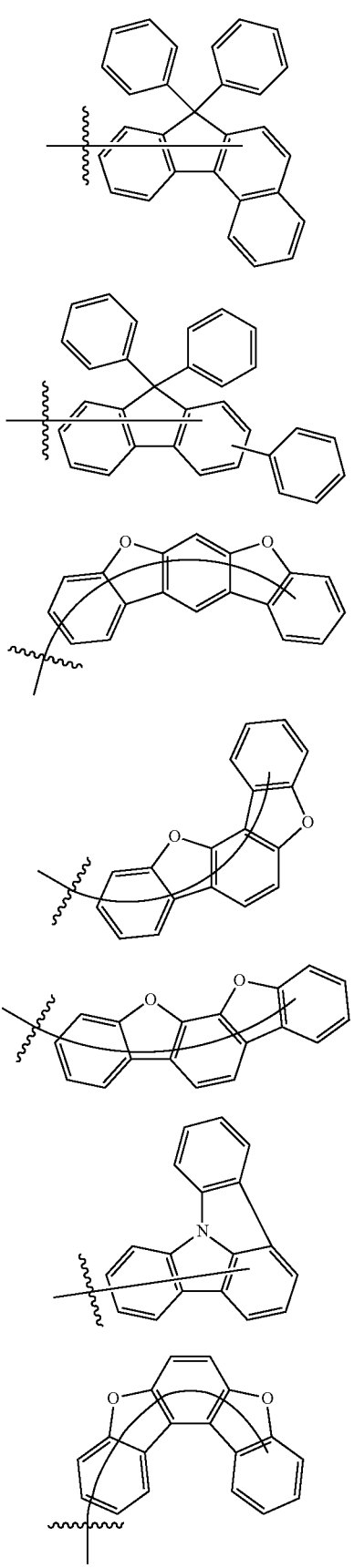
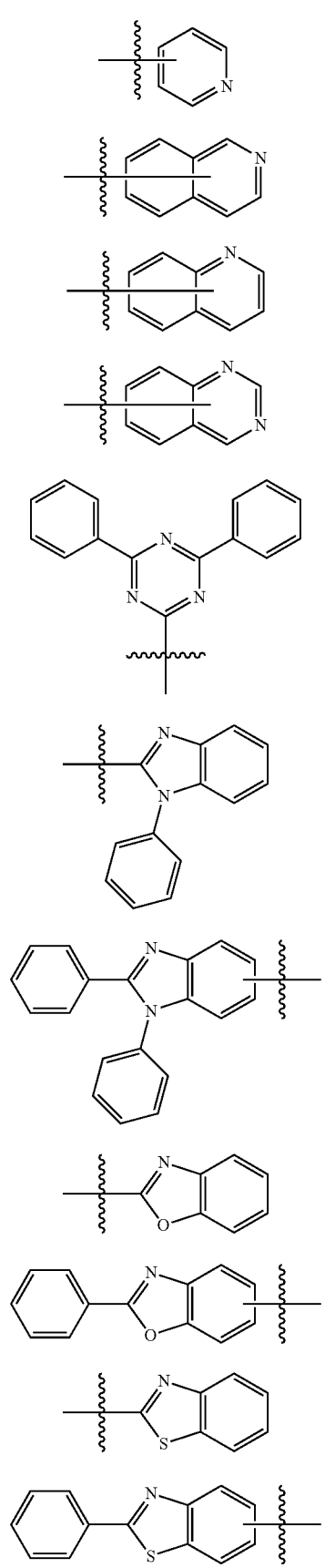
RB34
RB35
RB36
RB37
RB38
RB39
RB40
RB41
RB42
RB43
RB44
RB45
RB46
RB47
RB48
RB49
RB50
RB51

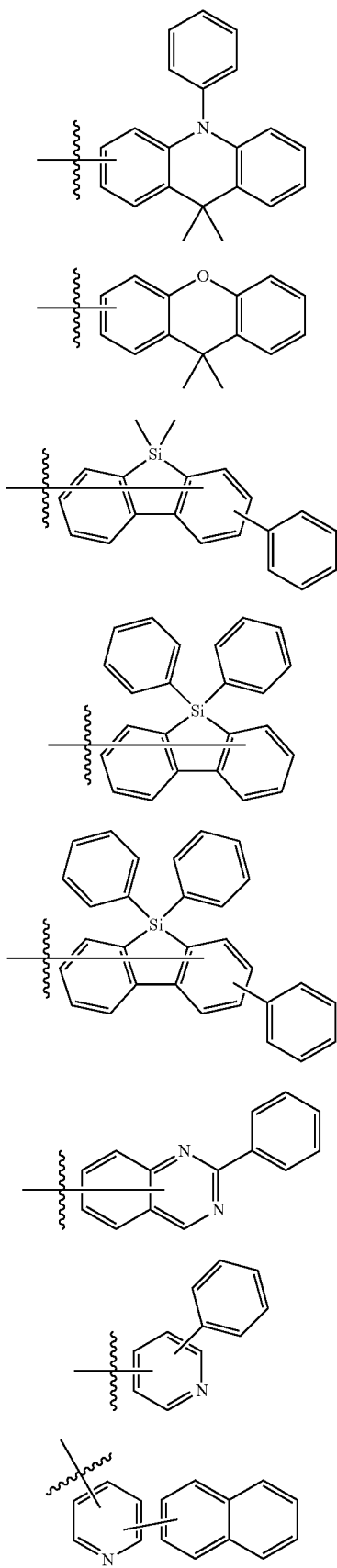

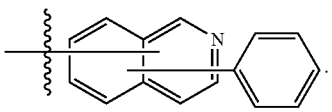

The organic light emitting device of the present disclosure can be manufactured using common organic light emitting device manufacturing methods and materials except that one or more organic material layers are formed using the above-described compound.

The compound can be formed into an organic material layer using a solution coating method as well as a vacuum deposition method when manufacturing the organic light emitting device. Herein, the solution coating method means spin coating, dip coating, inkjet printing, screen printing, a spray method, roll coating and the like, but is not limited thereto.

The organic material layer of the organic light emitting device of the present disclosure can be formed in a single layer structure, but can be formed in a multilayer structure in which two or more organic material layers are laminated. For example, the organic light emitting device of the present disclosure can have a structure comprising a hole injection layer, a hole transfer layer, a layer carrying out hole injection and hole transfer at the same time, a light emitting layer, an electron transfer layer, an electron injection layer, a layer carrying out electron injection and electron transfer at the same time and the like as an organic material layer. However, the structure of the organic light emitting device is not limited thereto, and can comprise less numbers of organic material layers.

In the organic light emitting device of the present disclosure, the organic material layer can comprise an electron transfer layer or an electron injection layer, and the electron transfer layer or the electron injection layer can comprise the compound of Chemical Formula 1.

In the organic light emitting device of the present disclosure, the organic material layer can comprise an electron blocking layer or a hole blocking layer, and the electron blocking layer or the hole blocking layer can comprise the compound of Chemical Formula 1.

In the organic light emitting device of the present disclosure, the organic material layer can comprise a hole injection layer or a hole transfer layer, and the hole injection layer or the hole transfer layer can comprise the compound of Chemical Formula 1.

In another embodiment, the organic material layer comprises a light emitting layer, and the light emitting layer comprises the compound of Chemical Formula 1.

According to another embodiment, the organic material layer comprises a light emitting layer, and the light emitting layer can comprise the compound of Chemical Formula 1 as a dopant of the light emitting layer.

In another embodiment, the organic material layer comprising the compound of Chemical Formula 1 comprises the compound of Chemical Formula 1 as a dopant, and can comprise Chemical Formula 1A or 1B as a host.

According to one embodiment of the present specification, the organic material layer comprises a light emitting layer, and the light emitting layer comprises the compound of Chemical Formula 1 as a dopant of the light emitting layer, comprises the compound of Chemical Formula 1A or Chemical Formula 1B as a host of the light emitting layer, and the compound of Chemical Formula 1 can be doped in 1 wt % to 30 wt %. According to another embodiment, the heteroring compound of Chemical Formula 1 can be doped in 2 wt % to 20 wt %.

In another embodiment, the organic material layer comprising the compound of Chemical Formula 1 comprises the compound of Chemical Formula 1 as a dopant, comprises a fluorescent host or a phosphorescent host, and can comprise other organic compounds, metals or metals compounds as a dopant.

As another example, the organic material layer comprising g the compound of Chemical Formula 1 comprises the compound of Chemical Formula 1 as a dopant, comprises a fluorescent host or a phosphorescent host, and can be used with an iridium (Ir)-based dopant.

In one embodiment of the present specification, the first electrode is an anode, and the second electrode is a cathode.

According to another embodiment, the first electrode is a cathode, and the second electrode is an anode.

The organic light emitting device of the present disclosure can have structures as illustrated in FIG. 1 and FIG. 2, however, the structure is not limited thereto.

FIG. 1 illustrates a structure of the organic light emitting device in which an anode (2), a light emitting layer (3) and a cathode (4) are consecutively laminated on a substrate (1). In such a structure, the compound can be included in the light emitting layer (3).

FIG. 2 illustrates a structure of the organic light emitting device in which an anode (2), a hole injection layer (5), a hole transfer layer (6), a light emitting layer (7), an electron transfer layer (8) and a cathode (4) on a substrate (1). In such a structure, the compound can be included in the hole injection layer (5), the hole transfer layer (6), the light emitting layer (7) or the electron transfer layer (8).

For example, the organic light emitting device according to the present disclosure can be manufactured by forming an anode on a substrate by depositing a metal, a metal oxide having conductivity, or an alloy thereof using a physical vapor deposition (PVD) method such as sputtering or e-beam evaporation, forming an organic material layer comprising a hole injection layer, a hole transfer layer, a light emitting layer and an electron transfer layer thereon, and then depositing a material usable as a cathode thereon. In addition to such a method, the organic light emitting device can also be manufactured by consecutively depositing a cathode material, an organic material layer and an anode material on a substrate.

The organic material layer can have a multilayer structure comprising a hole injection layer, a hole transfer layer, a light emitting layer and an electron transfer layer, but is not limited thereto, and can have a single layer structure. In addition, using various polymer materials, the organic material layer can be prepared to less numbers of layers using a solvent process instead of a deposition method such as spin coating, dip coating, doctor blading, screen printing, inkjet printing or a thermal transfer method.

As the anode material, materials having large work function are normally preferred so that hole injection to an organic material layer is smooth. Specific examples of the anode material usable in the present disclosure comprise metals such as vanadium, chromium, copper, zinc and gold, or alloys thereof, metal oxides such as zinc oxide, indium oxide, indium tin oxide (ITO) and indium zinc oxide (IZO), combinations of metals and oxides such as ZnO:Al or SnO$_2$:Sb, conductive polymers such as poly(3-methylthiophene), poly[3,4-(ethylene-1,2-dioxy)thiophene] (PEDOT), polypyrrole and polyaniline, but are not limited thereto.

As the cathode material, materials having small work function are normally preferred so that electron injection to an organic material layer is smooth. Specific examples of the cathode material comprise metals such as magnesium, calcium, sodium, potassium, titanium, indium, yttrium, lithium, gadolinium, aluminum, silver, tin and lead, or alloys thereof, multilayer structure materials such as LiF/Al or LiO$_2$/Al, and the like, but are not limited thereto.

The hole injection material is a material capable of favorably receiving holes from an anode at a low voltage, and the highest occupied molecular orbital (HOMO) of the hole injection material is preferably in between the work function of an anode material and the HOMO of surrounding organic material layers. Specific examples of the hole injection material comprise metal porphyrins, oligothiophene, arylamine-based organic materials, hexanitrile hexaazatriphenylene-based organic materials, quinacridone-based organic materials, perylene-based organic materials, anthraquinone, and polyaniline- and polythiophene-based conductive polymers, and the like, but are not limited thereto.

As the hole transfer material, materials capable of receiving holes from an anode or a hole injection layer, moving the holes to a light emitting layer, and having high mobility for the holes are suited. Specific examples thereof comprise arylamine-based organic materials, conductive polymers, block copolymers having conjugated parts and non-conjugated parts together, and the like, but are not limited thereto.

The light emitting layer can emit red, green or blue, and can be formed with a phosphorescent material or a fluorescent material. The light emitting material is a material capable of emitting light in a visible region by receiving holes and electrons from a hole transfer layer and an electron transfer layer, respectively, and binding the holes and the electrons, and is preferably a material having favorable quantum efficiency for fluorescence or phosphorescence. Specific examples thereof comprise 8-hydroxy-quinoline aluminum complexes (Alq$_3$), carbazole series compounds, dimerized styryl compounds, BAlq, 10-hydroxybenzoquinoline-metal compounds, benzoxazole, benzothiazole and benzimidazole series compounds, poly(p-phenylenevinylene) (PPV) series polymers, spiro compounds, polyfluorene, rubrene, and the like, but are not limited thereto.

A host material of the light emitting layer can comprise fused aromatic ring derivatives, heteroring-containing compounds or the like. Specifically, as the fused aromatic ring derivative, anthracene derivatives, pyrene derivatives, naphthalene derivatives, pentacene derivatives, phenanthrene compounds, fluoranthene compounds and the like can be included, and as the heteroring-containing compound, carbazole derivatives, dibenzofuran derivatives, ladder-type furan compounds, pyrimidine derivatives and the like can be included, however, the host material is not limited thereto.

The dopant material can comprise aromatic amine derivatives, styrylamine compounds, boron complexes, fluoranthene compounds, metal complexes and the like. Specifically, the aromatic amine derivative is a fused aromatic ring derivative having a substituted or unsubstituted arylamino group, and arylamino group—comprising pyrene, anthracene, chrysene, peryflanthene and the like can be included. The styrylamine compound is a compound in which substituted or unsubstituted arylamine is substituted with at least one arylvinyl group, and one, two or more substituents selected from the group consisting of an aryl group, a silyl group, an alkyl group, a cycloalkyl group and an arylamino group can be substituted or unsubstituted. Specifically, styrylamine, styryldiamine, styryltriamine, styryltetramine and the like can be included, however, the styrylamine compound is not limited thereto. As the metal complex, iridium complexes, platinum complexes and the like can be included, however, the metal complex is not limited thereto.

As the electron transfer material, materials capable of favorably receiving electrons from a cathode, moving the electrons to a light emitting layer, and having high mobility for the electrons are suited. Specific examples thereof comprise Al complexes of 8-hydroxyquinoline, complexes comprising $Alq_3$, organic radical compounds, hydroxyflavon-metal complexes, and the like, but are not limited thereto.

As the electron injection material, compounds having an electron transferring ability, having an electron injection effect from a cathode, having an excellent electron injection effect for a light emitting layer or light emitting material, and preventing excitons generated in the light emitting layer from moving to a hole injection layer, and in addition thereto, having an excellent thin film forming ability are preferred. Specific examples thereof comprise fluorenone, anthraquinodimethane, diphenoquinone, thiopyran dioxide, oxazole, oxadiazole, triazole, imidazole, perylene tetracarboxylic acid, fluorenylidene methane, anthrone or the like, and derivatives thereof, metal complex compounds, nitrogen-containing 5-membered ring derivatives, and the like, but are not limited thereto.

The metal complex compound comprises 8-hydroxyquinolinato lithium, bis(8-hydroxyquinolinato)zinc, bis(8-hydroxyquinolinato) copper, bis(8-hydroxyquinolinato)manganese, tris(8-hydroxyquinolinato)aluminum, tris(2-methyl-8-hydroxyquinolinato)-aluminum, tris(8-hydroxyquinolinato)gallium, bis(10-hydroxybenzo[h]quinolinato) berylium, bis(10-hydroxybenzo[h]quinolinato)-zinc, bis(2-methyl-8-quinolinato) chlorogallium, bis(2-methyl-8-quinolinato) (o-cresolato) gallium, bis(2-methyl-8-quinolinato) (1-naphtholato)aluminum, bis(2-methyl-8-quinolinato) (2-naphtholato)-gallium and the like, but is not limited thereto.

The hole blocking layer is a layer blocking holes from reaching a cathode, and can be generally formed under the same condition as the hole injection layer. Specific examples thereof can comprise oxadiazole derivatives, triazole derivatives, phenanthroline derivatives, BCP, aluminum complexes and the like, but are not limited thereto.

The organic light emitting device according to the present disclosure can be a top-emission type, a bottom-emission type or a dual-emission type depending on the materials used.

Hereinafter, the present specification will be described in detail with reference to examples. However, the examples according to the present specification can be modified to various other forms, and the scope of the present application is not to be construed as being limited to the examples described below. Examples of the present application are provided in order to more fully describe the present specification to those having average knowledge in the art.

SYNTHESIS EXAMPLES

Synthesis Example 1. Synthesis of Compound 1

1) Synthesis of Intermediate 1-1
Intermediate 1-1 was synthesized according to the following reaction scheme.

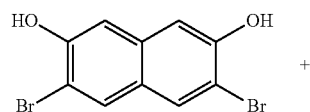

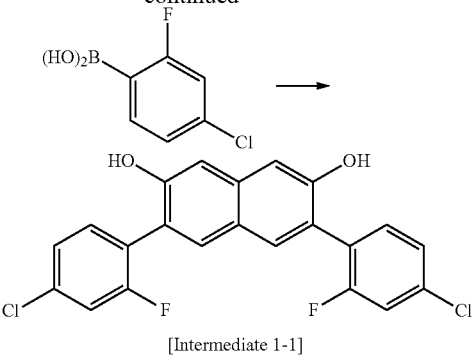

[Intermediate 1-1]

After introducing 3,6-dibromonaphthalene-2,7-diol (80.0 g, 0.25 mol) and (4-chloro-2-fluorophenyl)boronic acid (105.3 g, 0.60 mol) to a 2 L flask, 1,4-dioxane (0.8 L) and potassium carbonate (191.2 g, 1.38 mol) dissolved in water (0.4 L) were introduced thereto. While raising a temperature of the reactor until reflux, a tetrakistriphenylphosphine palladium catalyst (23.3 g, 0.02 mmol) was diluted in a small amount of 1,4-dioxane and then introduced thereto. After the reflux, termination of the reaction was checked, and the temperature was lowered again. This was extracted using water and an ethyl acetate solvent to remove the water layer, treated with anhydrous magnesium sulfate and charcoal, then filtered using a celite pad, and concentrated to obtain a target product. The target product was recrystallization purified using ethyl acetate and hexane to obtain <Intermediate 1-1> (52 g, yield 50%).

2) Synthesis of Intermediate 1-2

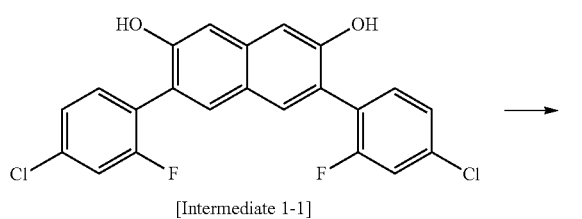

[Intermediate 1-1]

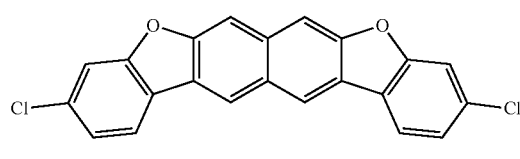

[Intermediate 1-2]

After introducing <Intermediate 1-1> (20.0 g, 0.05 mol) and potassium carbonate (19.9 g, 0.14 mol) to a 1 L flask, N-methyl-2-pyrrolidone (NMP) (0.6 L) was introduced thereto, and the result was stirred. The reaction temperature was raised to 150° C., and after stirring the result for 1 hour, the temperature was lowered to room temperature. After introducing water (0.3 L) to the reaction material, the result was further stirred for one hour, filtered, and washed with normal hexane (0.3 L). The result was dried with nitrogen, and <Intermediate 1-2> (15 g, yield 83%) was obtained.

MALDI-TOF MS [M+]=376.0

3) Synthesis of Compound 1

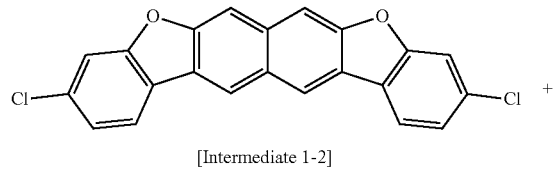

[Intermediate 1-2]

+

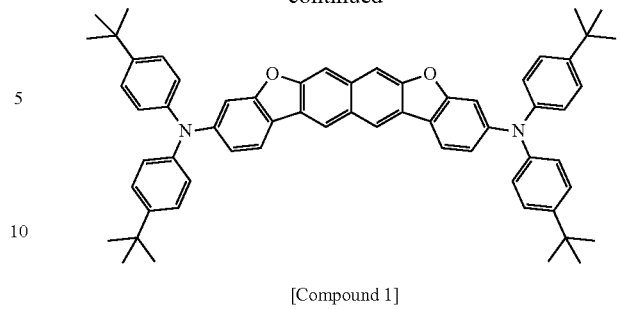

[Compound 1]

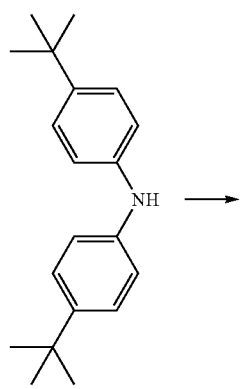

→

After introducing <Intermediate 1-2> (12.0 g, 0.03 mol), di-t-butylamine (18.8 g, 0.07 mmol) and sodium t-butoxide (13.8 g, 0.14 mol) to a 0.5 L flask with toluene (0.35 L), the temperature was raised to 130° C. Pd(t-Bu$_3$)$_2$ (0.98 g, 1.91 mmol) was added dropwise to the reaction material with a small amount of toluene. After reacting for approximately 2 hours, the reaction temperature was lowered to room temperature, and the result was extracted using a supersaturated aqueous ammonium chloride solution and ethyl acetate. The obtained organic layer was treated with activated carbon, anhydrous magnesium sulfate and charcoal, and then concentrated through celite filtration. The result was recrystallization purified with ethyl acetate and hexane, and dried with nitrogen to obtain <Compound 1> (9.5 g, yield 34%). Proton NMR data are shown in FIG. 4.

MS [M+H]=868

Synthesis Example 2. Synthesis of Compound 2

Compound 2 was synthesized according to the following reaction scheme.

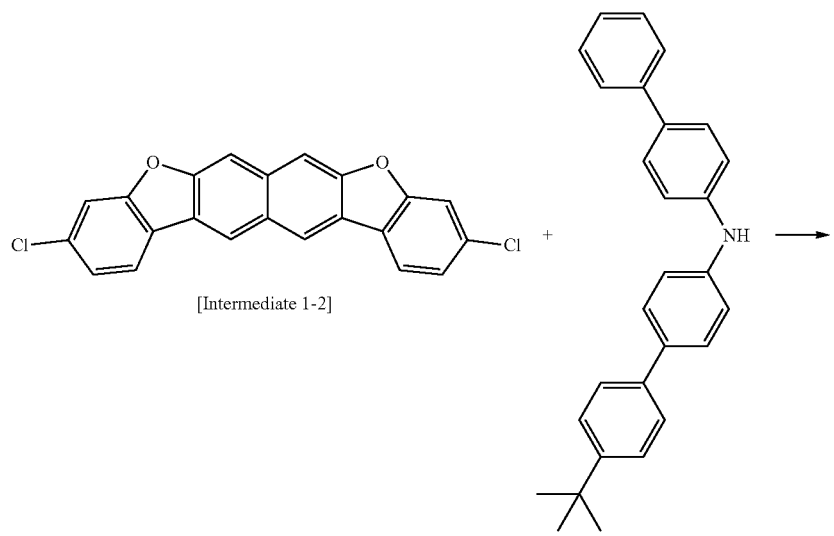

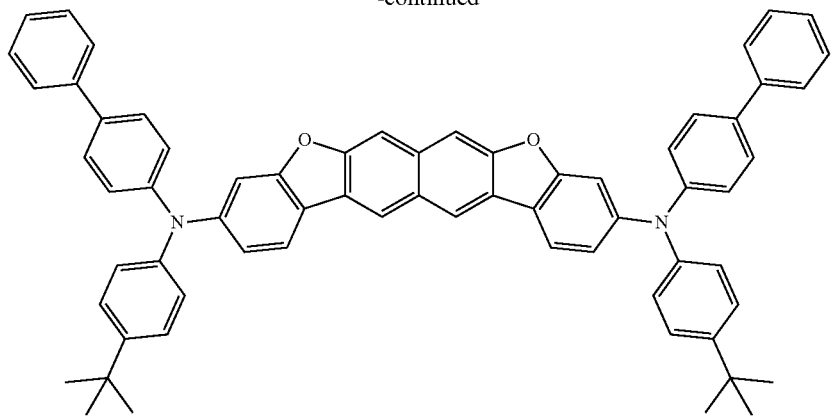
[Compound 2]
<Compound 2> (9.5 g, yield 34%) was obtained in the same manner as in the synthesis of Compound 1 using <Intermediate 1-2> (7.5 g, 0.02 mol) and N-(4-(tert-butyl)phenyl)-[1,1'-biphenyl]-4-amine (12.6 g, 0.04 mol).
MS [M+H]=908
Synthesis Example 3. Synthesis of Compound 4
Compound 4 was synthesized according to the following reaction scheme.
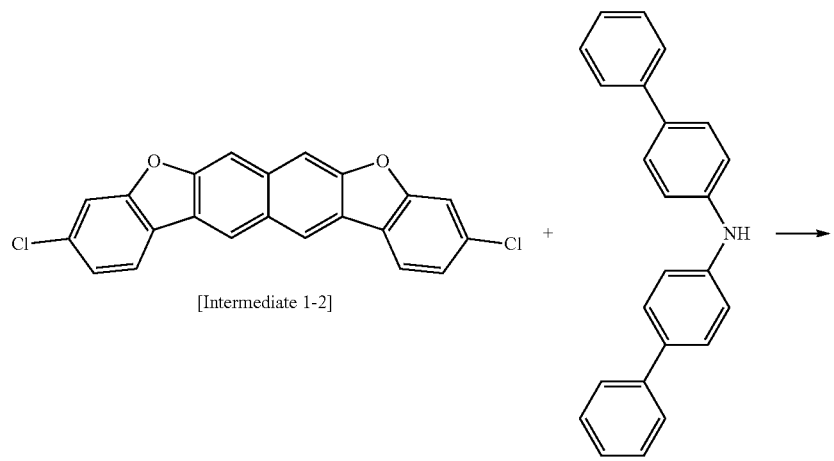
[Intermediate 1-2]
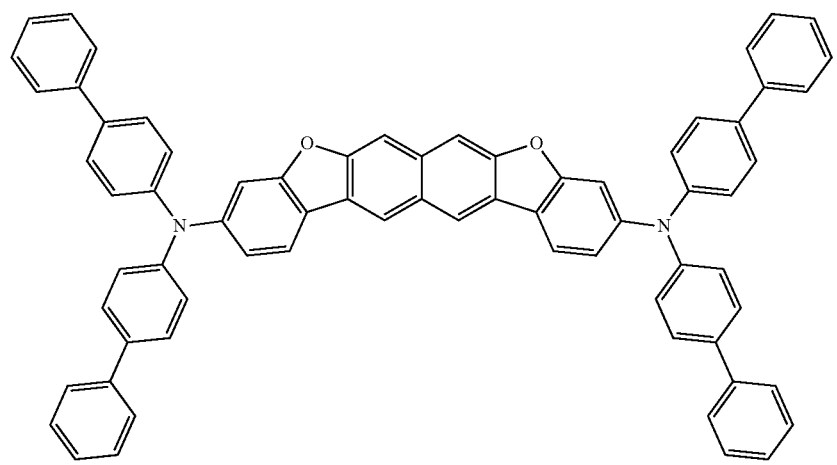
[Compound 4]

<Compound 4> (6.3 g, yield 31%) was obtained in the same manner as in the synthesis of Compound 1 using <Intermediate 1-2> (8.0 g, 0.02 mol) and di([1,1'-biphenyl]-4-yl)amine (14.3 g, 0.05 mol).

Synthesis Example 4. Synthesis of Compound 33

1) Synthesis of Intermediate 3-1
Intermediate 3-1 was synthesized according to the following reaction scheme.

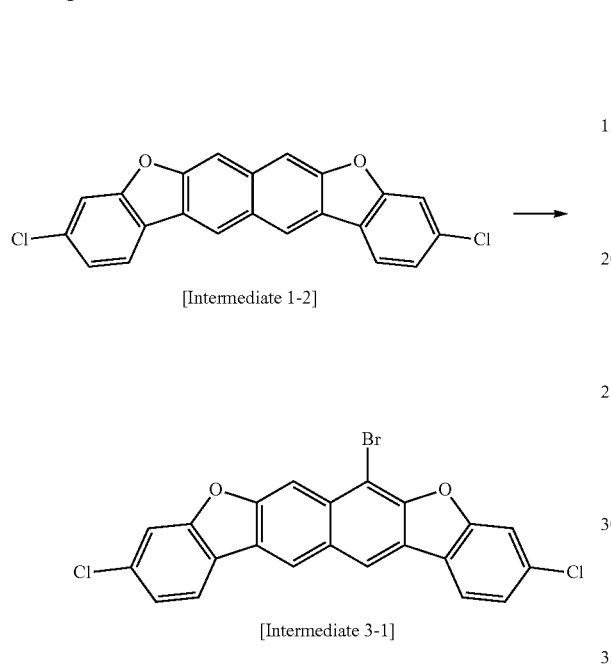

[Intermediate 1-2]

[Intermediate 3-1]

After introducing <Intermediate 1-2> (40.0 g, 0.106 mol) and N-bromosuccinimide (NBS) (20.8 g, 0.117 mol) to a 0.5 L flask, a solvent (300 mL) of chloroform: dimethylformaldehyde (DMF) in a 3:1 ratio was introduced thereto. The temperature was raised from room temperature to 70° C., and the result was stirred for 60 hours. After the reaction was terminated, the temperature was lowered to room temperature. Solids obtained through filtration was extracted using water and a chloroform solvent to remove the water layer, treated with anhydrous magnesium sulfate and charcoal, then filtered using a celite pad, and concentrated to obtain a target product. The target product was recrystallization purified using chloroform and normal hexane to obtain <Intermediate 3-1> (10.5 g, yield 22%).
MS [M+H]=457

2) Synthesis of Intermediate 3-2

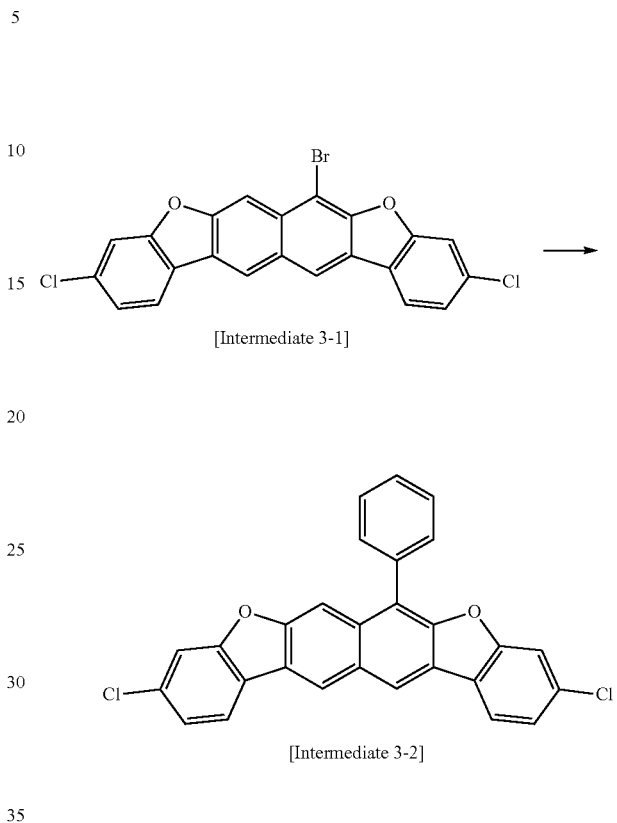

[Intermediate 3-1]

[Intermediate 3-2]

After introducing <Intermediate 3-1> (10.0 g, 0.22 mol) to a 0.25 L flask, anhydrous tetrahydrofuran (1 M THF) (29 mL) was added thereto under the nitrogen atmosphere, and the temperature was lowered to −40° C. Phenylmagnesium bromide (24 ml) was slowly introduced thereto, and after raising the temperature to room temperature, the result was stirred for 24 hours. After the reaction was all completed, the reaction solution was extracted with water and chloroform, treated with anhydrous magnesium sulfate, filtered, and then vacuum concentrated. Obtained solids were recrystallization purified using toluene and normal hexane to obtain <Intermediate 3-2> (6.0 g, yield 60%).
MS [M+H]=454

3) Synthesis of Compound 33

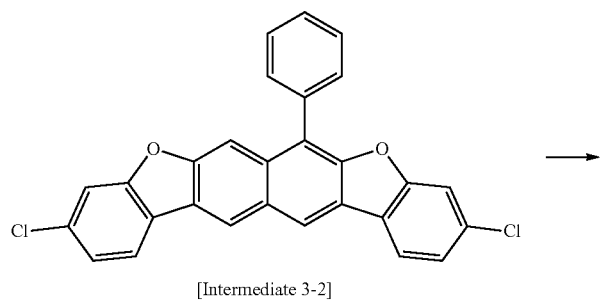

[Intermediate 3-2]

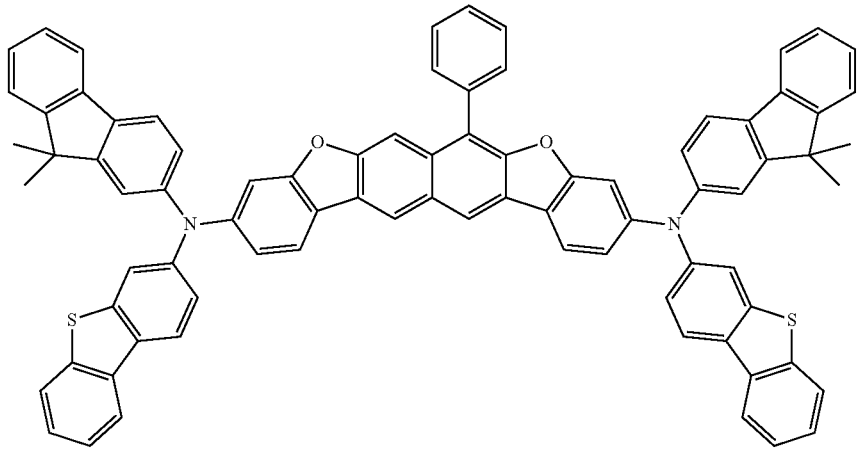
[Compound 33]
<Compound 33> (4.6 g, yield 30%) was obtained in the same manner as in the synthesis of Compound 1 using <Intermediate 3-2> (6.0 g, 0.13 mol) and N-(9,9-dimethyl-9H-fluoren-2-yl)dibenzo[b,d]thiophene-3-amine (11.4 g, 0.029 mol).
MS [M+H]=1164
EXAMPLES
HT-A
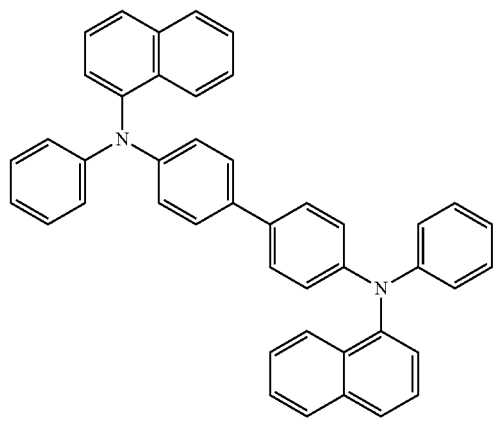
HAT
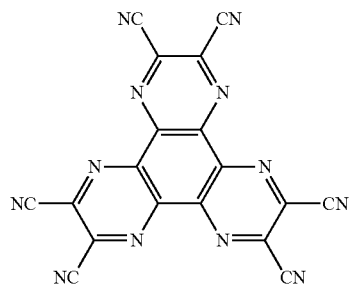
-continued
HT-B
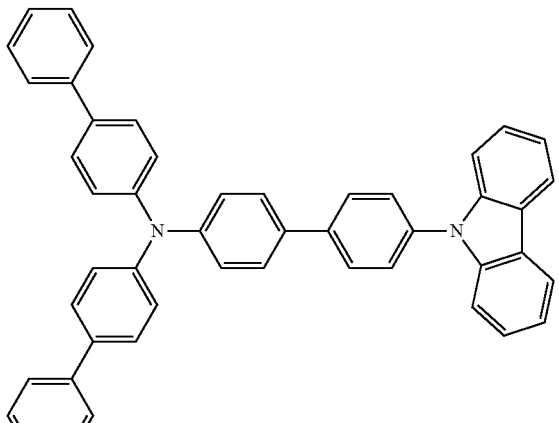
Liq
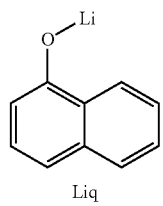

ET-A
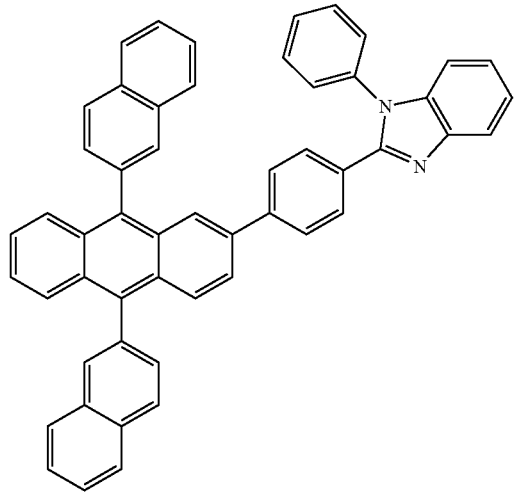
H-B
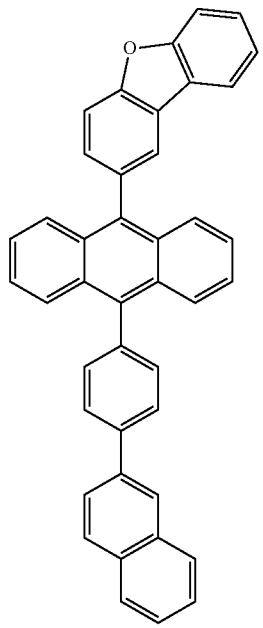
H-C
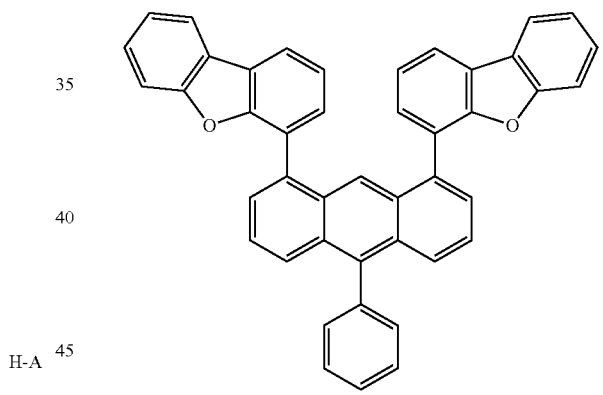
H-A
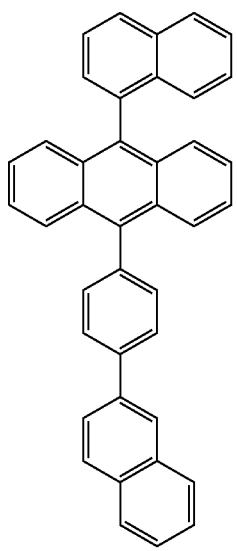
D-1
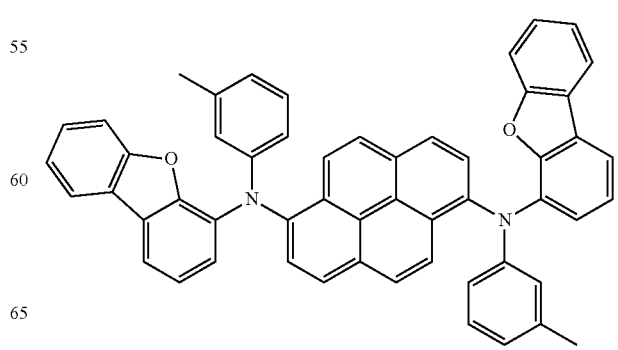

-continued

D-2

D-3

D-4

Example 1

A glass substrate (corning 7059 glass) on which indium tin oxide (ITO) was coated as a thin film to a thickness of 1,000 Å was placed in dispersant-dissolved distilled water and ultrasonic cleaned. A product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol, acetone and methanol in this order, then dried.

On the transparent ITO electrode prepared as above, a hole injection layer was formed by thermal vacuum depositing HAT to a thickness of 50 Å. As a hole transfer layer, the following HT-A was vacuum deposited to 1000 Å thereon, and HT-B was subsequently deposited to 100 Å. A light emitting layer was vacuum deposited to a thickness of 200 Å using H-A as a host, and doping Compound 1 in wt % 2 to 10 wt %. Then, ET-A and Liq were deposited to 300 Å in a ratio of 1:1, and magnesium (Mg) 10 wt % doped with silver (Ag) having a thickness of 150 Å and aluminum having a thickness of 1,000 Å were consecutively deposited thereon to form a cathode, and as a result, an organic light emitting device was manufactured.

In the above-mentioned process, the deposition rates of the organic materials were maintained at 1 Å/sec, and the deposition rates of the LiF and the aluminum were maintained at 0.2 Å/sec and 3 Å/sec to 7 Å/sec, respectively.

Example 2

An organic light emitting device was manufactured in the same manner as in Example 1 except that Compound 2 was used instead of Compound 1 in Example 1.

Example 3

An organic light emitting device was manufactured in the same manner as in Example 1 except that Compound 4 was used instead of Compound 1 in Example 1.

Example 4

An organic light emitting device was manufactured in the same manner as in Example 1 except that Compound 33 was used instead of Compound 1 in Example 1.

Example 5

An organic light emitting device was manufactured in the same manner as in Example 1 except that Compound H-B was used instead of H-A in Example 1.

Example 6

An organic light emitting device was manufactured in the same manner as in Example 2 except that Compound H-B was used instead of H-A in Example 2.

Example 7

An organic light emitting device was manufactured in the same manner as in Example 3 except that Compound H-B was used instead of H-A in Example 3.

Example 8

An organic light emitting device was manufactured in the same manner as in Example 4 except that Compound H-B was used instead of H-A in Example 4.

Example 9

An organic light emitting device was manufactured in the same manner as in Example 1 except that Compound H-C was used instead of H-A in Example 1.

Example 10

An organic light emitting device was manufactured in the same manner as in Example 2 except that Compound H-C was used instead of H-A in Example 2.

Example 11

An organic light emitting device was manufactured in the same manner as in Example 3 except that Compound H-C was used instead of H-A in Example 3.

Example 12

An organic light emitting device was manufactured in the same manner as in Example 4 except that Compound H-C was used instead of H-A in Example 4.

COMPARATIVE EXAMPLES

Comparative Example 1

An organic light emitting device was manufactured in the same manner as in Example 1 except that D-1 was used instead of Compound 1 in Example 1.

Comparative Example 2

An organic light emitting device was manufactured in the same manner as in Comparative Example 1 except that D-2 was used instead of Compound D-1 in Comparative Example 1.

Comparative Example 3

An organic light emitting device was manufactured in the same manner as in Comparative Example 1 except that D-3 was used instead of Compound D-1 in Comparative Example 1.

Comparative Example 4

An organic light emitting device was manufactured in the same manner as in Comparative Example 1 except that D-4 was used instead of Compound D-1 in Comparative Example 1.

Comparative Example 5

An organic light emitting device was manufactured in the same manner as in Comparative Example 1 except that Compound H-B was used instead of H-A in Comparative Example 1.

Comparative Example 6

An organic light emitting device was manufactured in the same manner as in Comparative Example 2 except that Compound H-B was used instead of H-A in Comparative Example 2.

Comparative Example 7

An organic light emitting device was manufactured in the same manner as in Comparative Example 3 except that Compound H-B was used instead of H-A in Comparative Example 3.

Comparative Example 8

An organic light emitting device was manufactured in the same manner as in Comparative Example 1 except that Compound H-C was used instead of H-A in Comparative Example 1.

Comparative Example 9

An organic light emitting device was manufactured in the same manner as in Comparative Example 2 except that Compound H-C was used instead of H-A in Comparative Example 2.

Comparative Example 10

An organic light emitting device was manufactured in the same manner as in Comparative Example 3 except that Compound H-C was used instead of H-A in Comparative Example 3.

Comparative Example 11

An organic light emitting device was manufactured in the same manner as in Comparative Example 4 except that Compound H-C was used instead of H-A in Comparative Example 4.

For the organic light emitting devices of Examples 1 to 12 and Comparative Examples 1 to 11, a driving voltage and light emission efficiency were measured at current density of 10 mA/cm$^2$, and time taken for the luminance decreasing to 95% compared to its initial luminance (LT95) was measured at current density of 20 mA/cm$^2$. The results are shown in the following Table 1.

TABLE 1

| Example | Host | Dopant | @ 10 mA/cm$^2$ Voltage (V) | @ 10 mA/cm$^2$ Efficiency (cd/A) | CIE y | @ 20 mA/cm$^2$ Lifetime (hr) |
|---|---|---|---|---|---|---|
| Example 1 | H-A | Compound 1 | 4.3 | 6.25 | 0.040 | 145 |
| Example 2 | H-A | Compound 2 | 4.2 | 6.53 | 0.042 | 180 |
| Example 3 | H-A | Compound 4 | 4.6 | 6.30 | 0.043 | 165 |
| Example 4 | H-A | Compound 33 | 4.4 | 6.60 | 0.044 | 190 |
| Example 5 | H-B | Compound 1 | 4.2 | 6.23 | 0.040 | 185 |
| Example 6 | H-B | Compound 2 | 4.2 | 6.50 | 0.042 | 190 |
| Example 7 | H-B | Compound 4 | 4.4 | 6.50 | 0.043 | 185 |
| Example 8 | H-B | Compound 33 | 4.2 | 6.60 | 0.044 | 190 |
| Example 9 | H-C | Compound 1 | 4.3 | 6.75 | 0.040 | 220 |
| Example 10 | H-C | Compound 2 | 4.3 | 6.65 | 0.042 | 190 |
| Example 11 | H-C | Compound 4 | 4.6 | 6.50 | 0.043 | 195 |
| Example 12 | H-C | Compound 33 | 4.4 | 6.60 | 0.044 | 200 |
| Comparative Example 1 | H-A | D-1 | 4.6 | 6.10 | 0.043 | 140 |
| Comparative Example 2 | H-A | D-2 | 4.6 | 5.20 | 0.042 | 130 |
| Comparative Example 3 | H-A | D-3 | 4.7 | 6.10 | 0.040 | 120 |
| Comparative Example 4 | H-A | D-4 | 4.8 | 4.20 | 0.032 | 60 |
| Comparative Example 5 | H-B | D-1 | 4.5 | 5.80 | 0.043 | 130 |
| Comparative Example 6 | H-B | D-2 | 4.5 | 5.00 | 0.042 | 110 |
| Comparative Example 7 | H-B | D-3 | 4.6 | 5.75 | 0.040 | 105 |

TABLE 1-continued

| | | | @ 10 mA/cm² | | | @ 20 |
| Example | Host | Dopant | Voltage (V) | Efficiency (cd/A) | CIE y | mA/cm² Lifetime (hr) |
|---|---|---|---|---|---|---|
| Comparative Example 8 | H-C | D-1 | 4.7 | 5.90 | 0.043 | 135 |
| Comparative Example 9 | H-C | D-2 | 4.7 | 5.30 | 0.043 | 115 |
| Comparative Example 10 | H-C | D-3 | 4.6 | 5.75 | 0.039 | 85 |
| Comparative Example 11 | H-C | D-4 | 4.6 | 5.30 | 0.033 | 70 |

From Table 1, it was identified that Examples 1 to 12 using the compound of Chemical Formula 1 of the present application as a dopant of a light emitting layer had a lower device driving voltage, excellent efficiency and long lifetime properties compared to Comparative Examples 1, 5 and 8 using pyrene-based compounds, Comparative Examples 2, 6 and 9 using benzofluorene-based compounds, and Comparative Examples 3, 7 and 10 using boron-based compounds. Particularly, it was identified that Comparative Examples 4 and 11 using a compound (D-4) having a similar core structure with the compound of Chemical Formula 1 of the present application but having a different central element included in the core structure had a higher device driving voltage, low efficiency, and particularly, device lifetime properties decreasing to approximately 51% to 73% compared to Examples 1 to 12 of the present application.

-continued
RB5 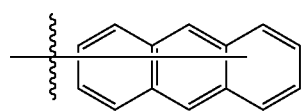
RB6 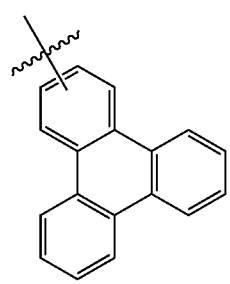
RB7 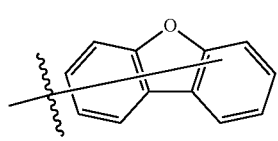
RB8 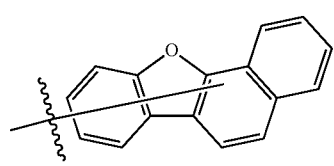
RB9 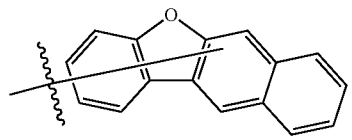
RB10 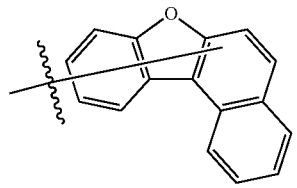
RB11 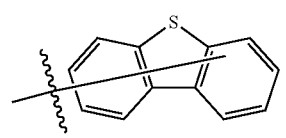
RB12 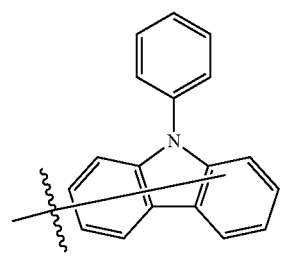
-continued
RB13 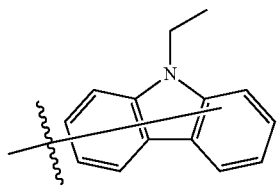
RB14 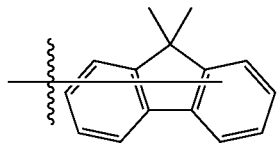
RB15 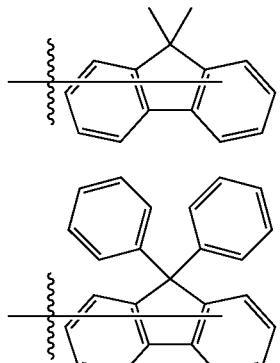
RB16 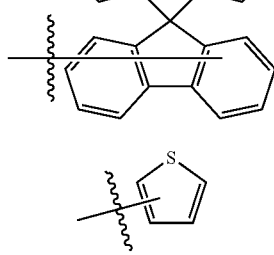
RB17 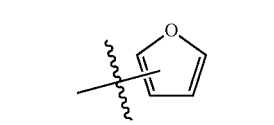
RB18 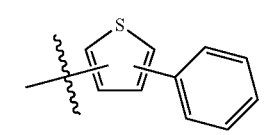
RB19 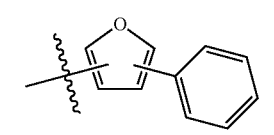
RB20 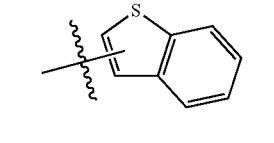
RB21 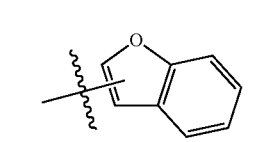
RB22 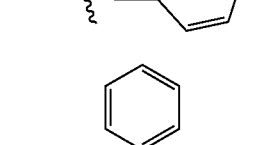

-continued
RB23
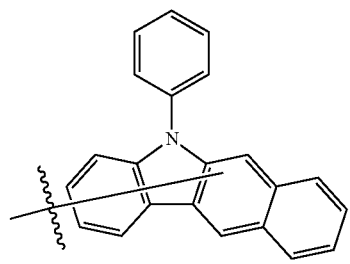
RB24
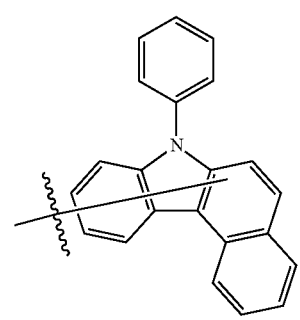
RB25
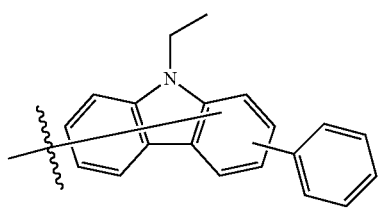
RB26
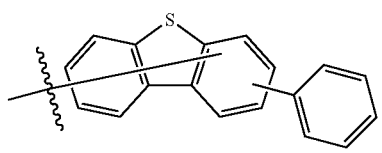
RB27
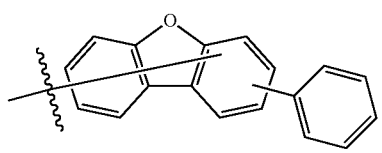
RB28
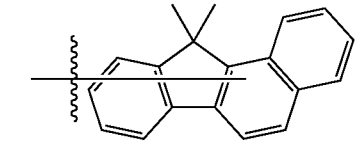
RB29
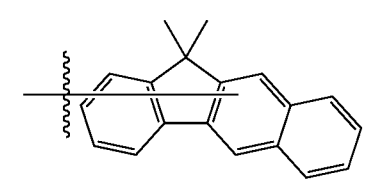
-continued
RB30
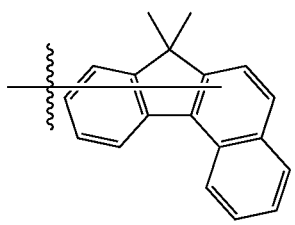
RB31
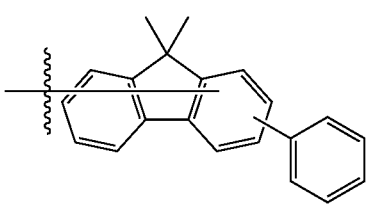
RB32
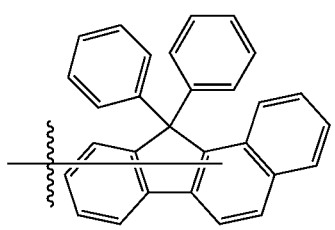
RB33
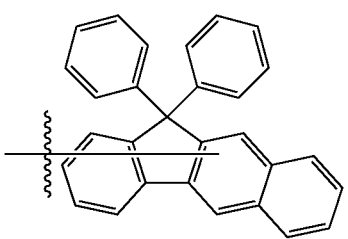
RB34
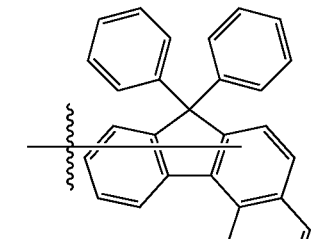
RB35
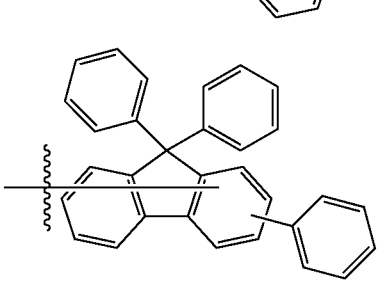
RB36
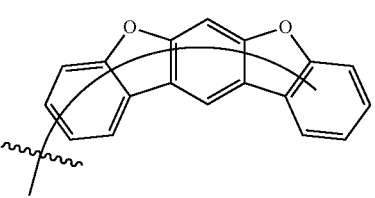

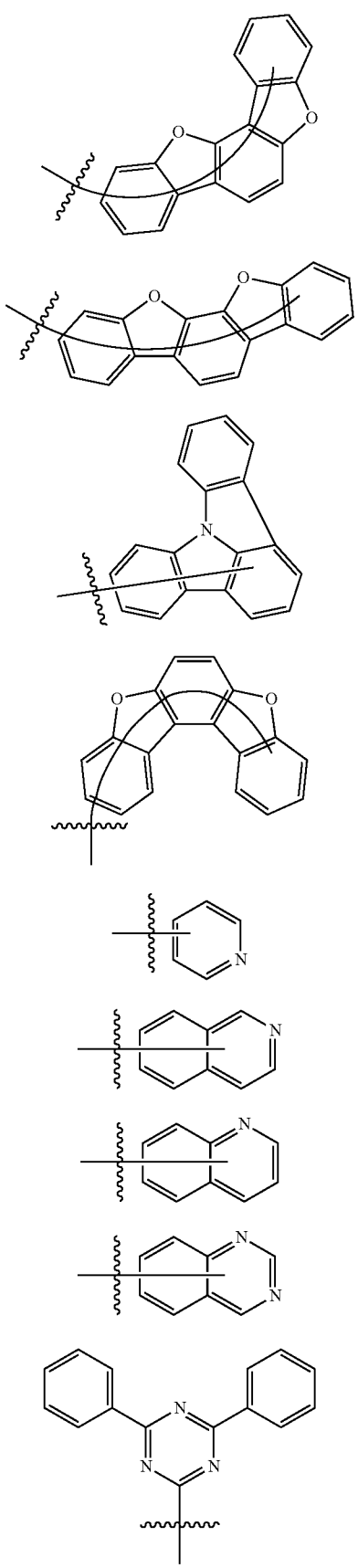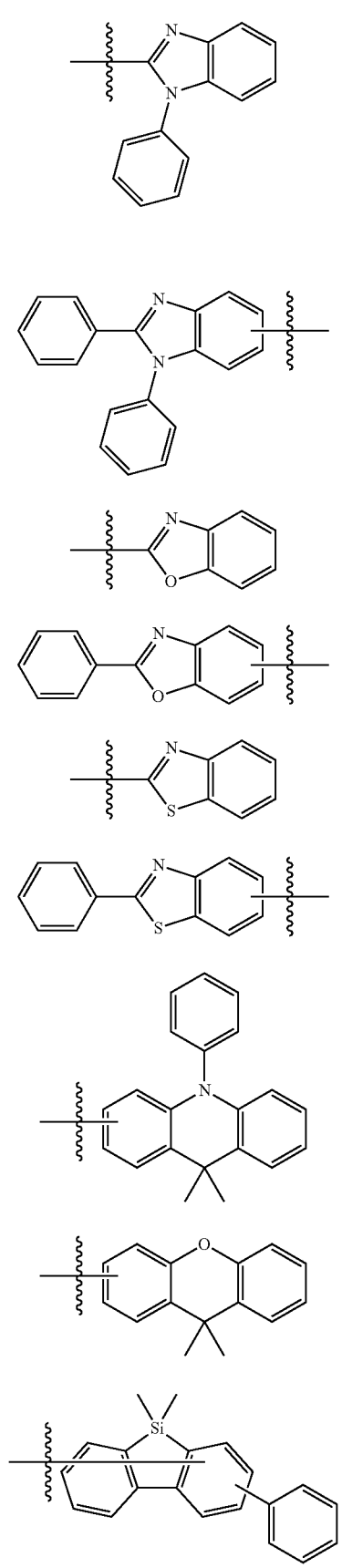

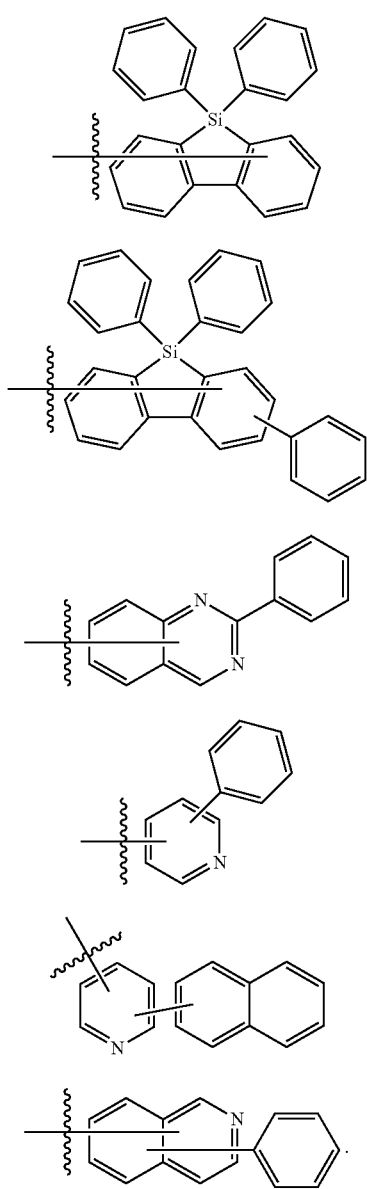
10. The organic light emitting device of claim 7, wherein L107 to L109 are the same as or different from each other, and each independently is a direct bond or selected from among the following structures:
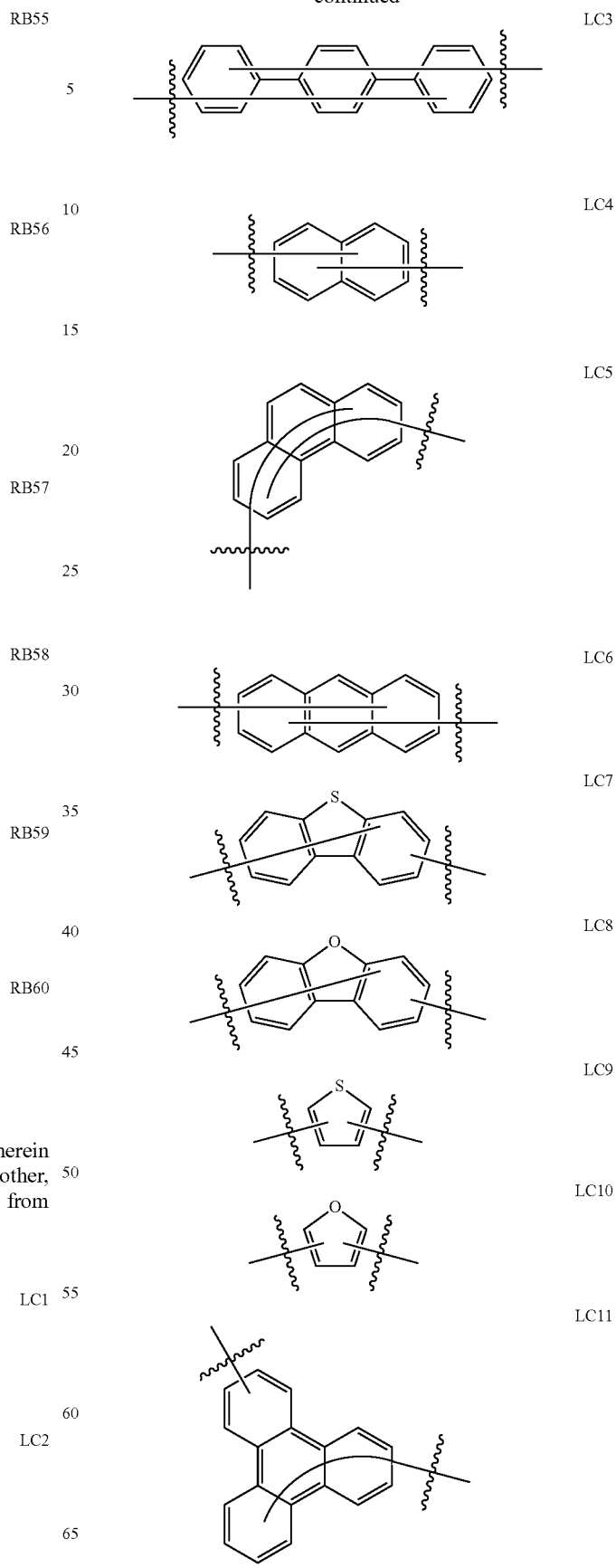

-continued
LC12
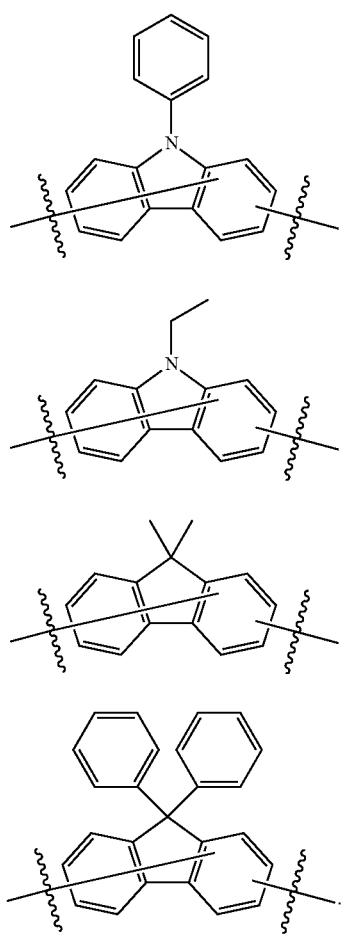
LC13
LC14
LC15
11. The organic light emitting device of claim 7, wherein Ar9 to Ar11 are the same as or different from each other, and each independently is selected from among the following structures:
RB1
RB2
RB3
RB4
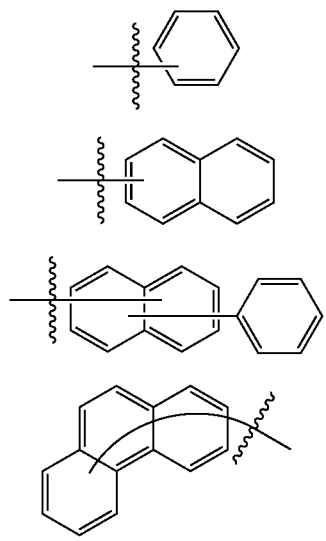
-continued
RB5
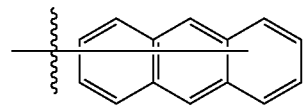
RB6
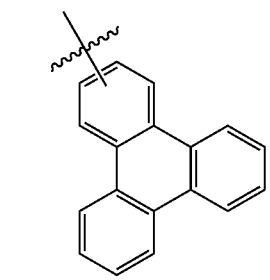
RB7
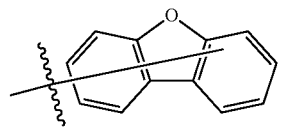
RB8
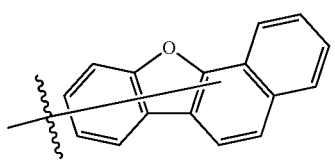
RB9
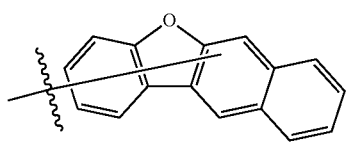
RB10
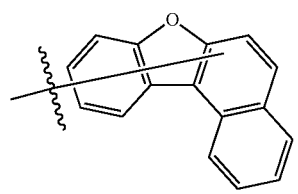
RB11
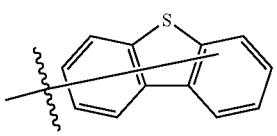
RB12
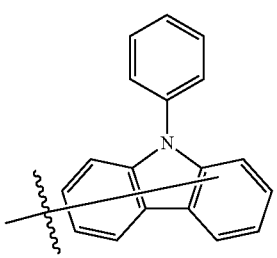

-continued
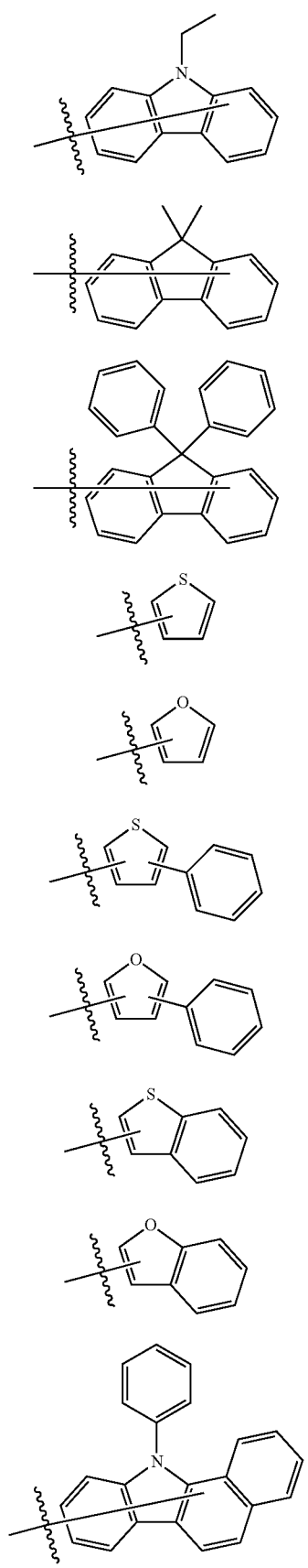
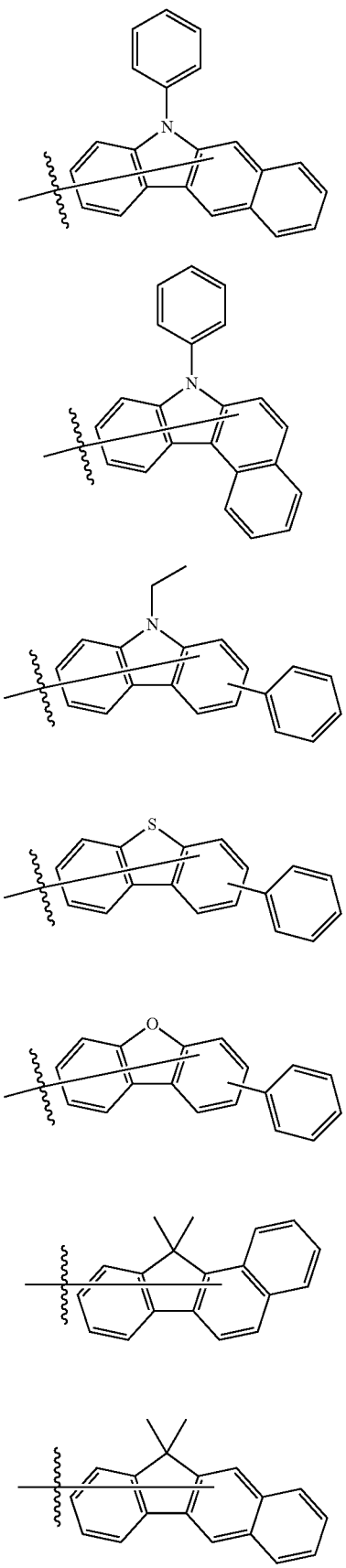

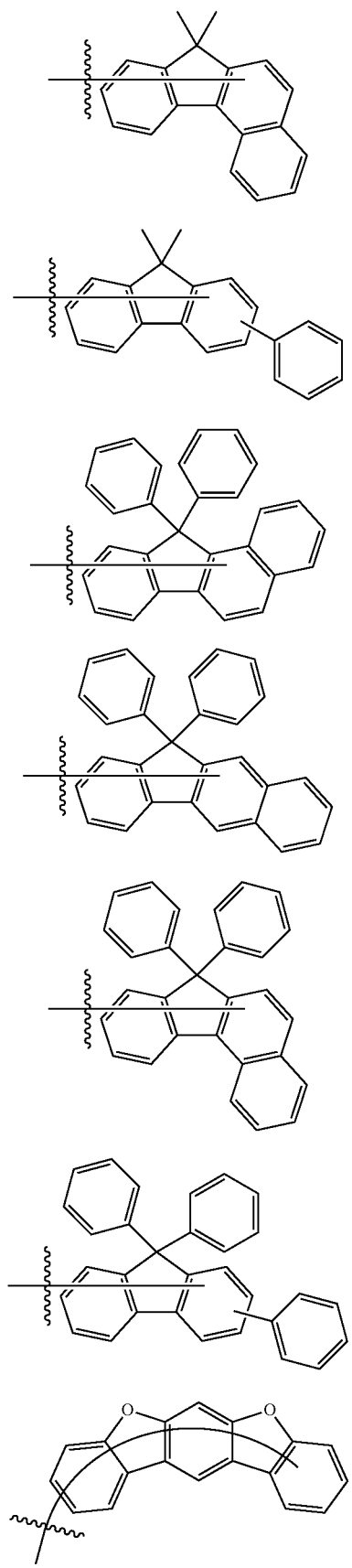
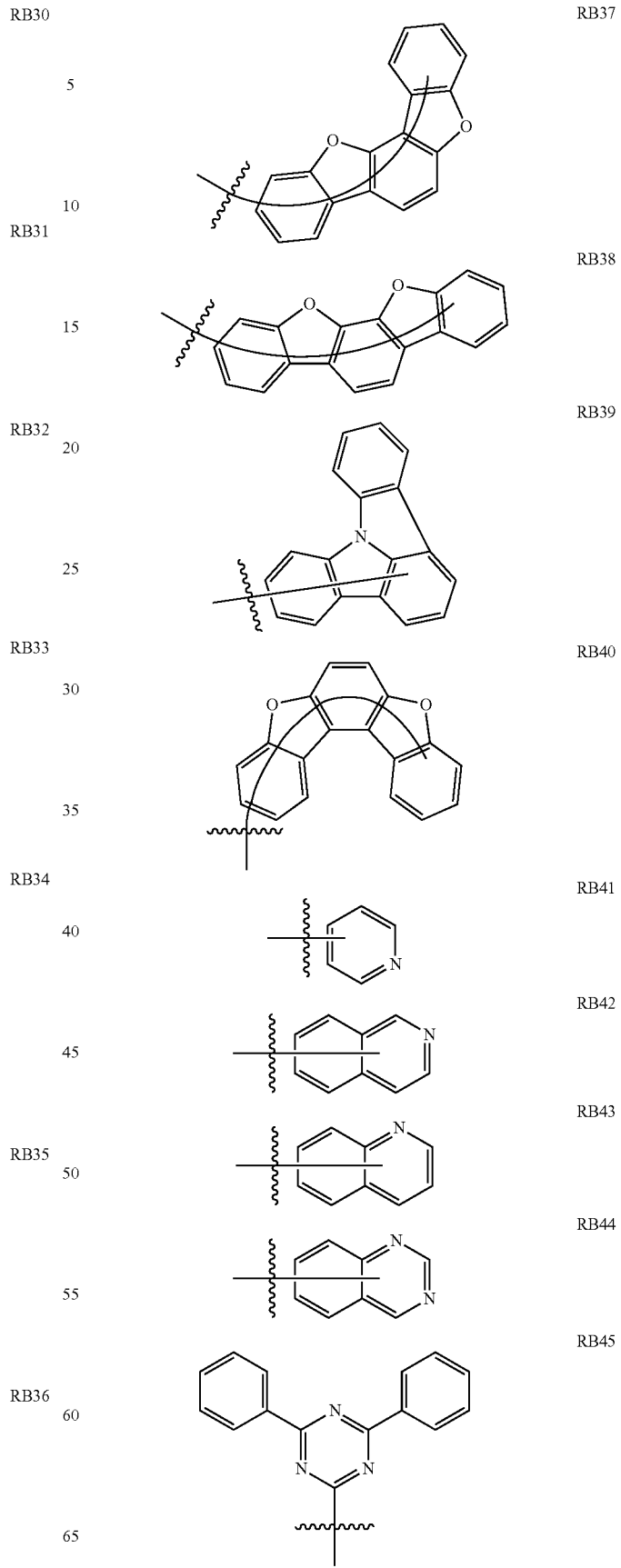

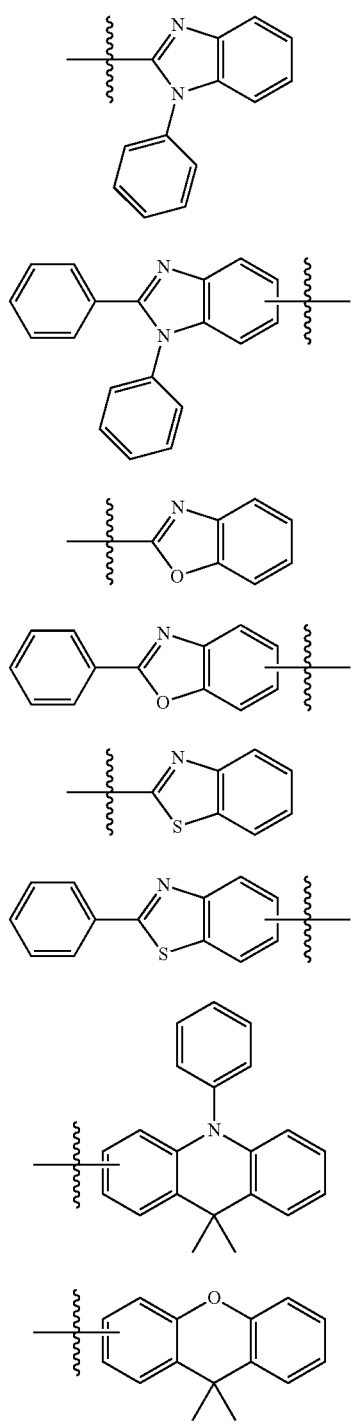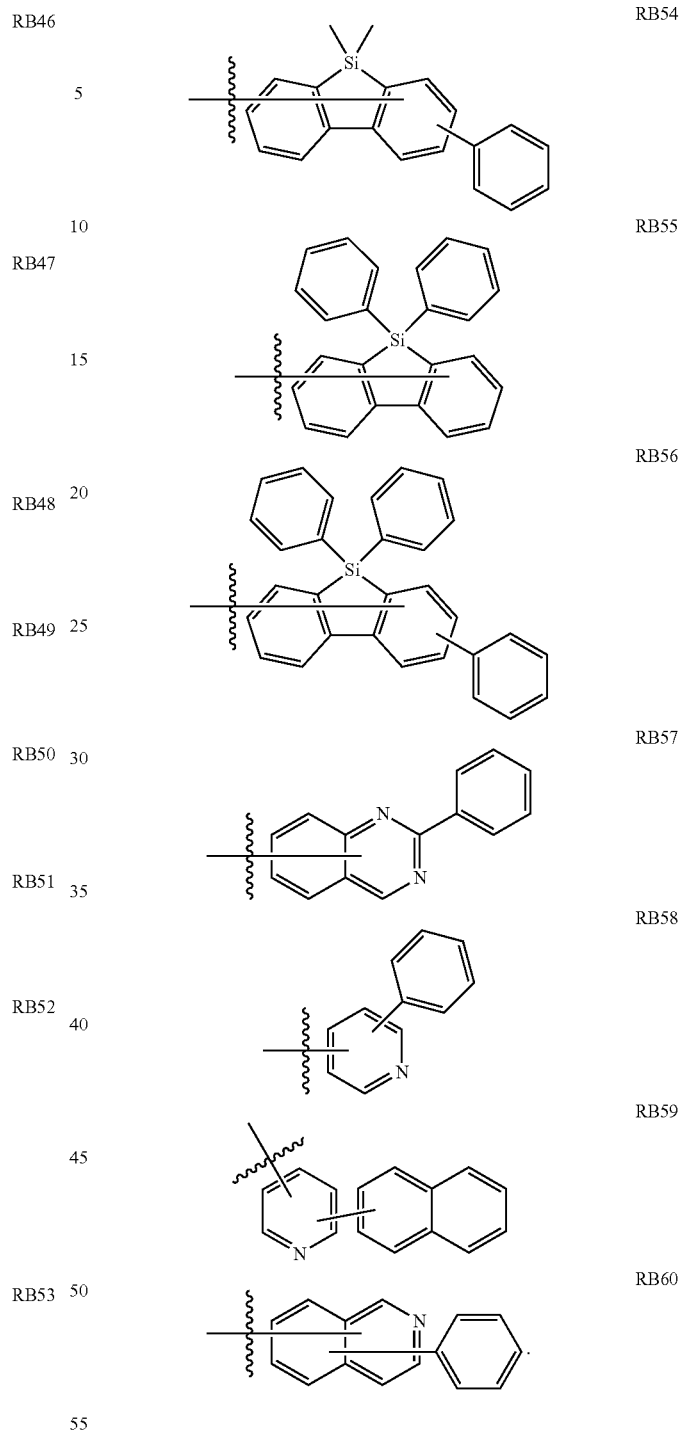

The invention claimed is:
1. An organic light emitting device, comprising:
a first electrode;
a second electrode provided opposite to the first electrode; and
one or more organic material layers provided between the first electrode and the second electrode,
wherein one or more layers of the organic material layers comprise the compound of Chemical Formula 5 or 8:

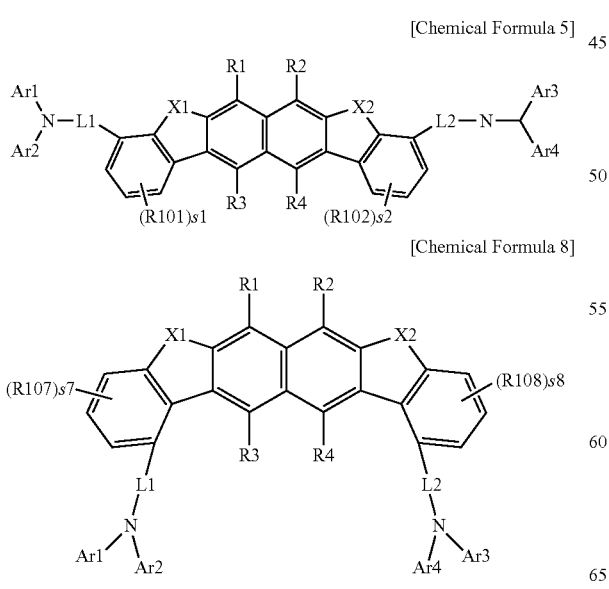

[Chemical Formula 5]

[Chemical Formula 8]

wherein, in Chemical Formula 5 or 8:
X1 and X2 are the same as or different from each other, and each independently is O, S, CRaRb or NRc;
Ra, Rb, Rc and R1 to R4 are the same as or different from each other, and each independently is hydrogen, deuterium, a halogen group, a cyano group, a sulfide group, a sulfonyl group, a substituted or unsubstituted alkyl group, a substituted or unsubstituted cycloalkyl group, a substituted or unsubstituted arylamine group, a substituted or unsubstituted aryl group, or a substituted or unsubstituted heteroaryl group;
Ar1 to Ar4 are the same as or different from each other, and each independently is a substituted or unsubstituted aryl group or a substituted or unsubstituted heteroaryl group, or adjacent groups bond to each other to form a substituted or unsubstituted ring;
L1 and L2 are the same as or different from each other, and each independently is a direct bond or a substituted or unsubstituted arylene group;
R101, R102, R107, and R108 are the same as or different from each other, and each independently is hydrogen, deuterium, a halogen group, a cyano group, a sulfide group, a sulfonyl group, a substituted or unsubstituted alkyl group, a substituted or unsubstituted cycloalkyl group, a substituted or unsubstituted arylamine group, a substituted or unsubstituted aryl group, or a substituted or unsubstituted heteroaryl group;
s1, s2, s7, and s8 are each an integer of 0 to 3, and when any of s1, s2, s7, or s8 is an integer of 2 or greater, substituents in the parentheses are the same as or different from each other;
wherein one of the organic material layers comprises a light emitting layer, and the light emitting layer comprises a compound of Chemical Formula 1B:

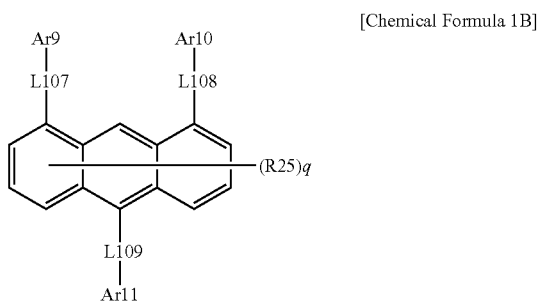

[Chemical Formula 1B]

wherein in Chemical Formula 1B:
L107 to L109 are the same as or different from each other, and each independently is a direct bond, a substituted or unsubstituted arylene group, or a substituted or unsubstituted heteroarylene group;
Ar9 to Ar11 are the same as or different from each other, and each independently is a substituted or unsubstituted aryl group or a substituted or unsubstituted heteroaryl group;
R25s are the same as or different from each other, and each independently is hydrogen, deuterium, a halogen group, a nitrile group, a nitro group, a substituted or unsubstituted alkyl group, a substituted or unsubstituted cycloalkyl group, a substituted or unsubstituted silyl group, a substituted or unsubstituted phosphine oxide group, a substituted or unsubstituted aryl group, or a substituted or unsubstituted heteroaryl group;

q is an integer of 0 to 7; and when q is 2 or greater, substituents in the parentheses are the same as or different from each other.

2. The organic light emitting device of claim 1, wherein the one of the organic material layers comprises any one of the following compounds:

Compound 1

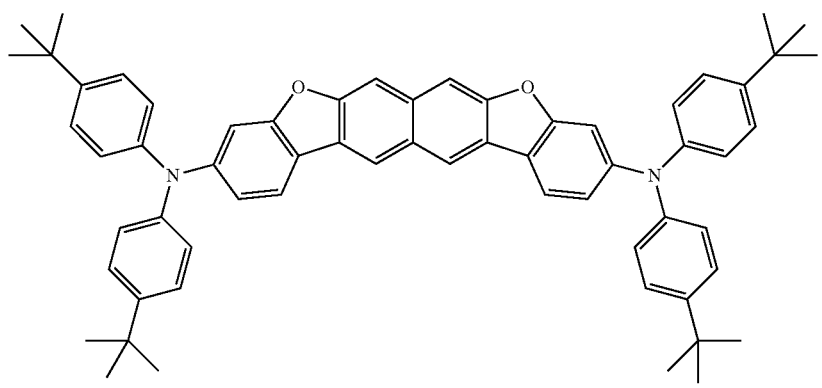

Compound 2

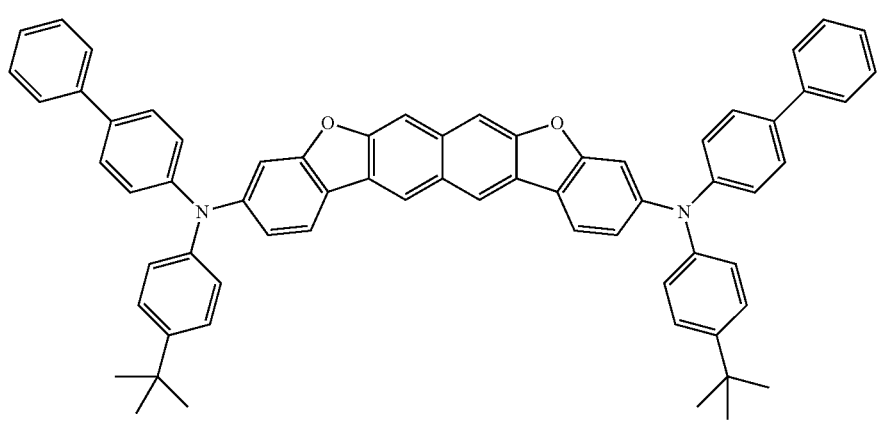

Compound 3

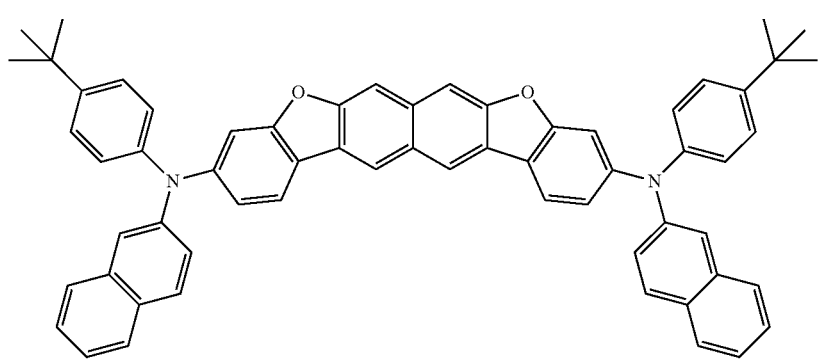

Compound 5
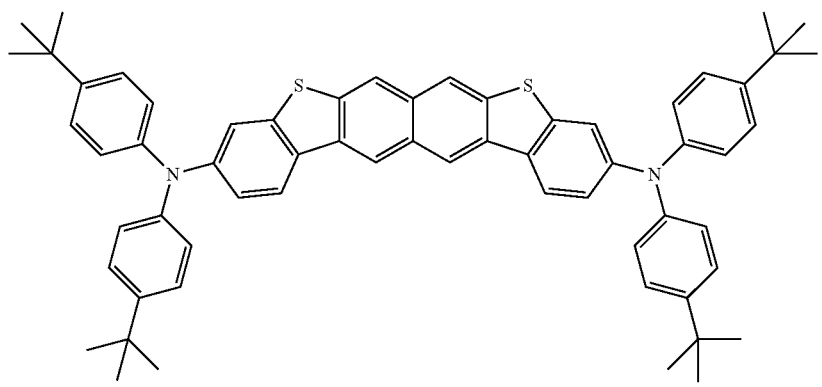
Compound 6
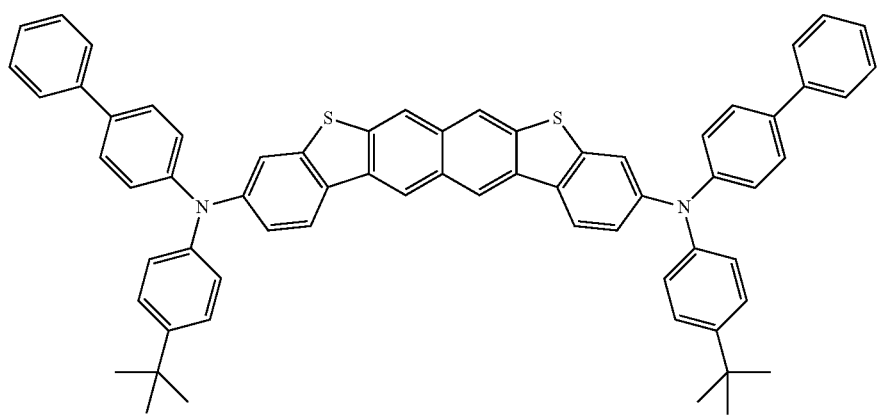
Compound 7
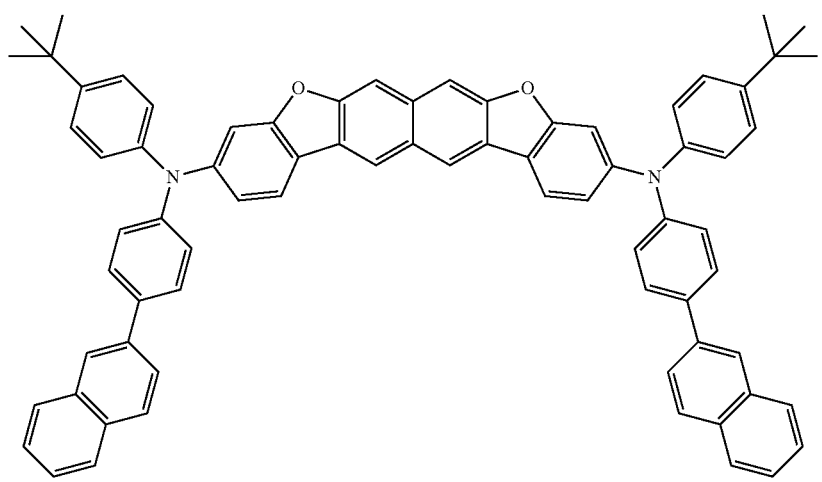

Compound 8
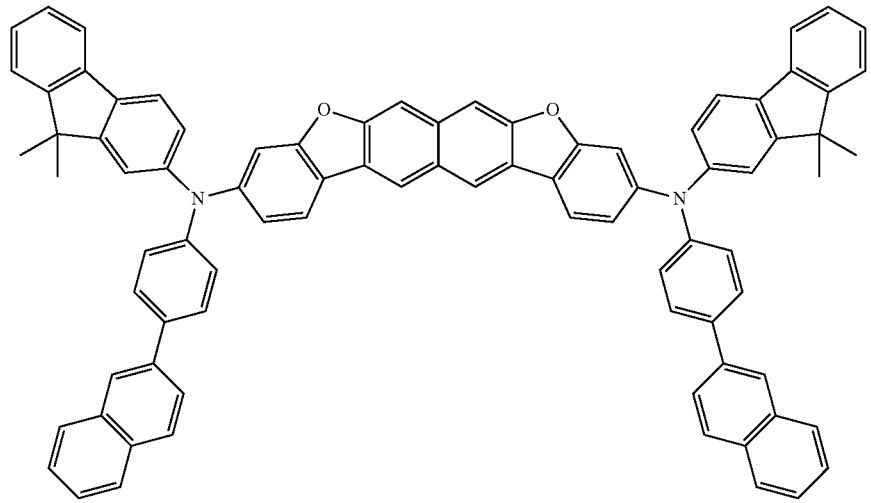
Compound 9
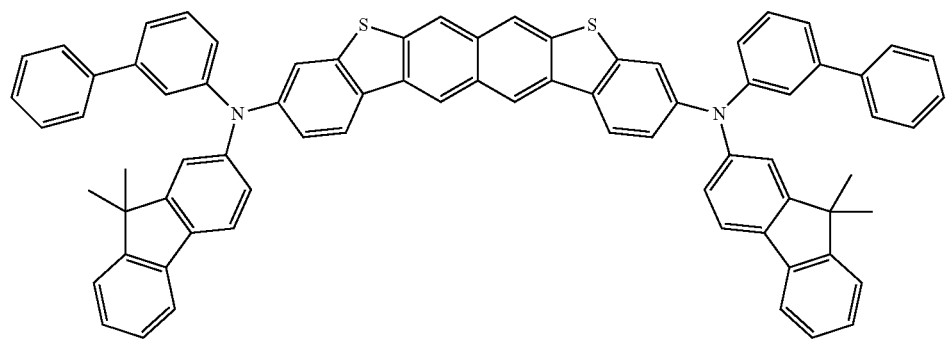
Compound 10
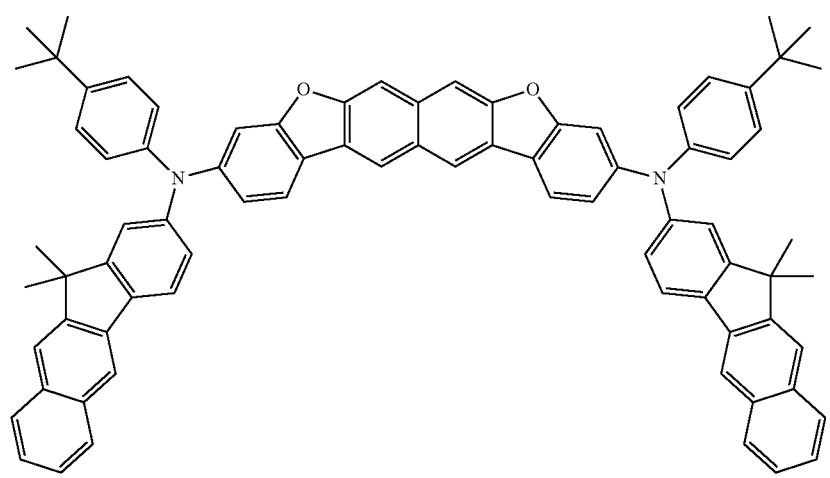

Compound 11
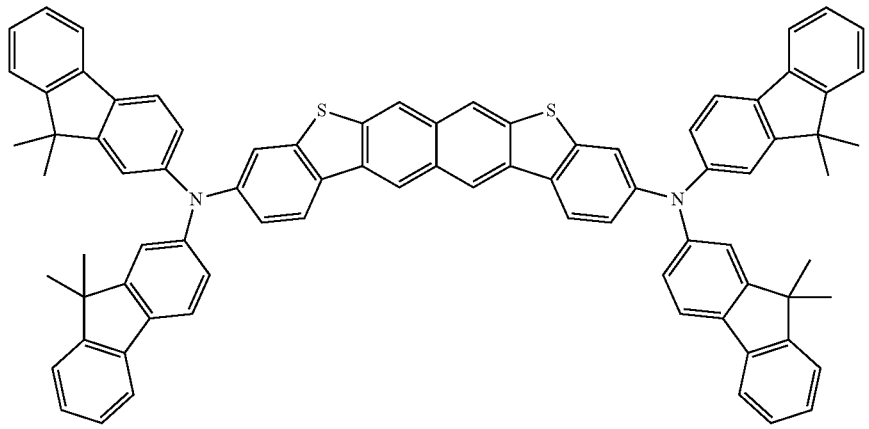
Compound 12
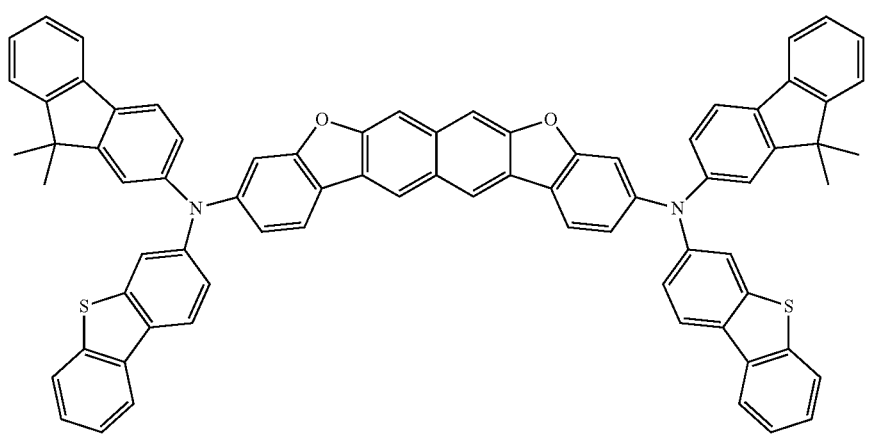
Compound 13
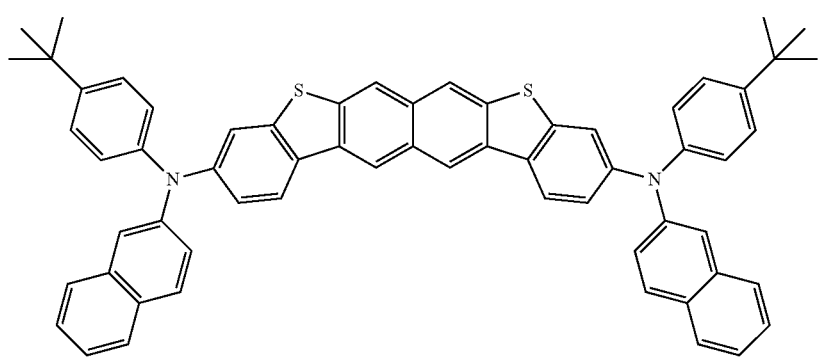
Compound 14
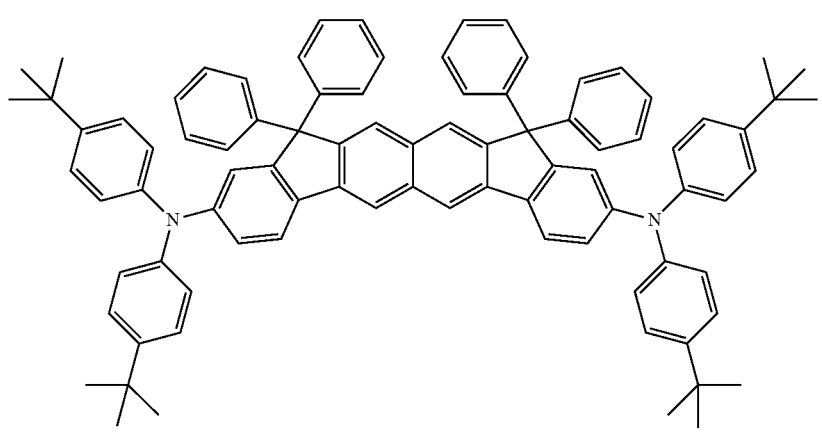

-continued
Compound 15
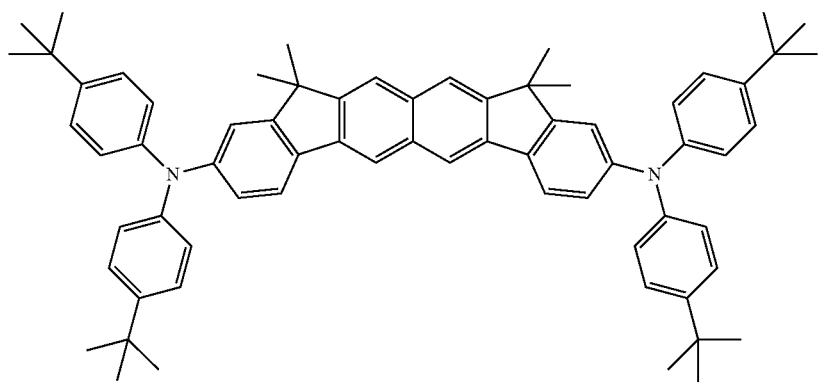
Compound 16
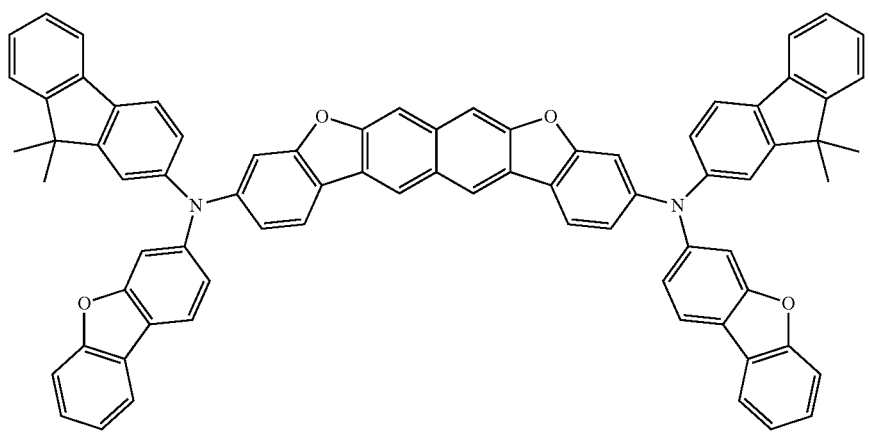
Compound 17
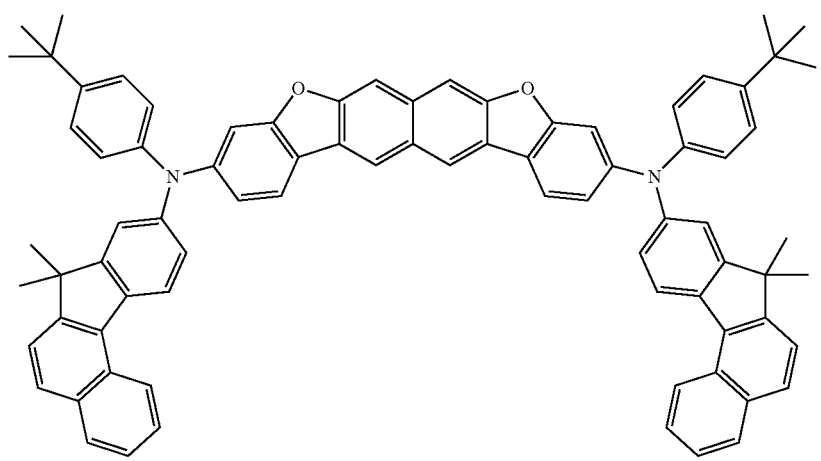

-continued
Compound 18
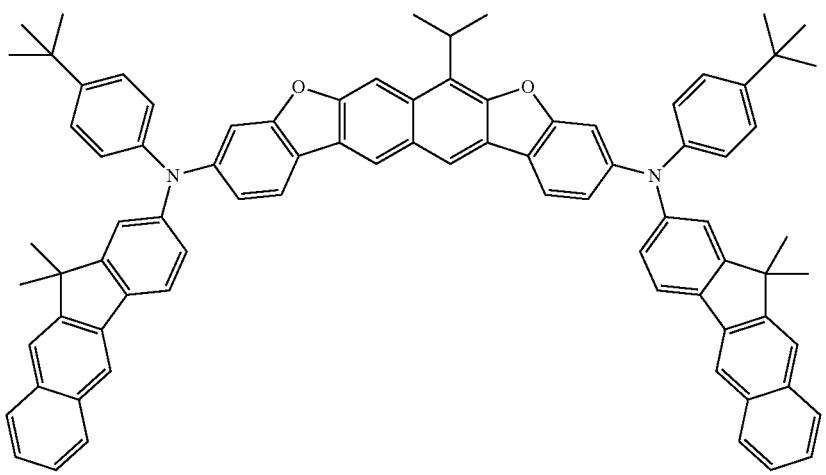
Compound 19
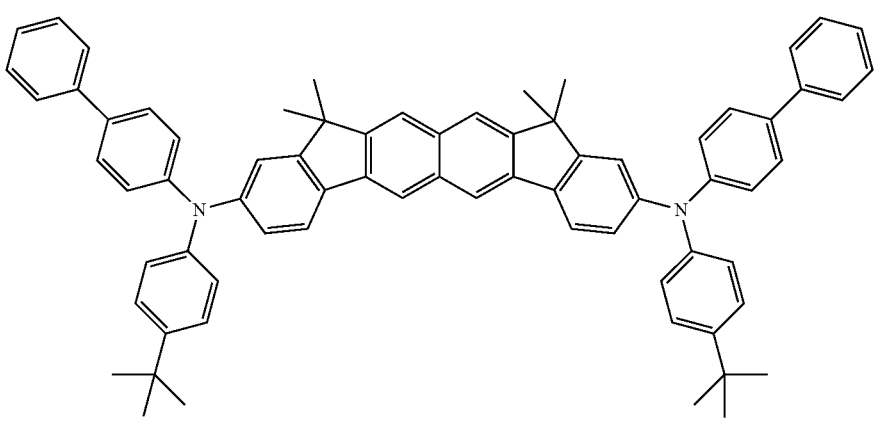
Compound 20
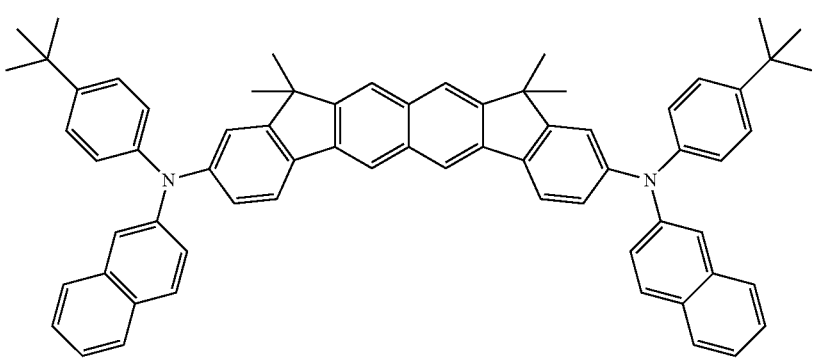
Compound 21
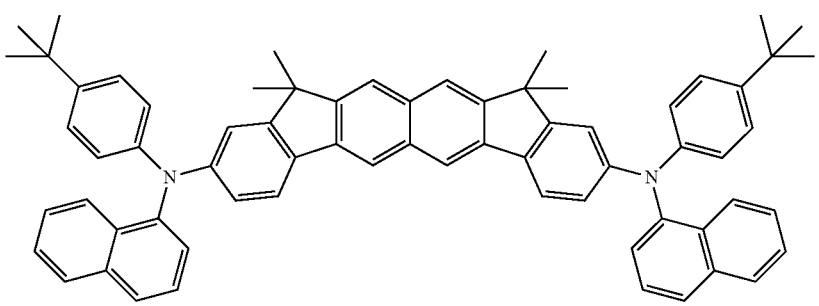

-continued
Compound 22
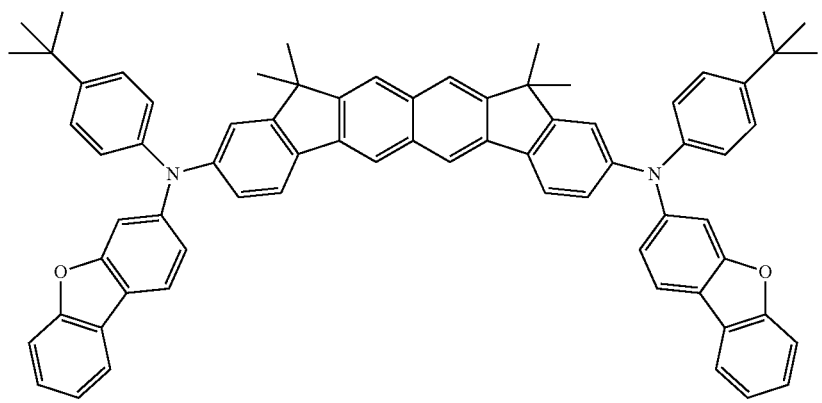
Compound 23
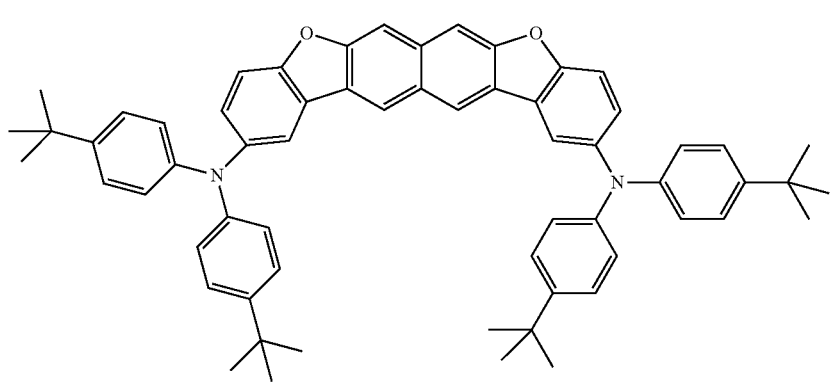
Compound 24
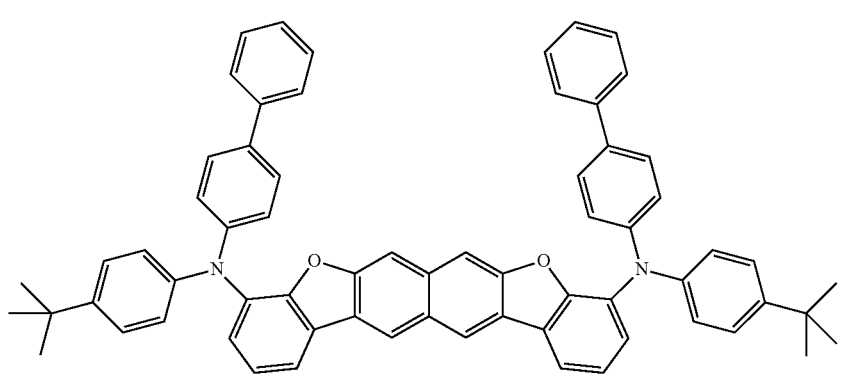
Compound 25
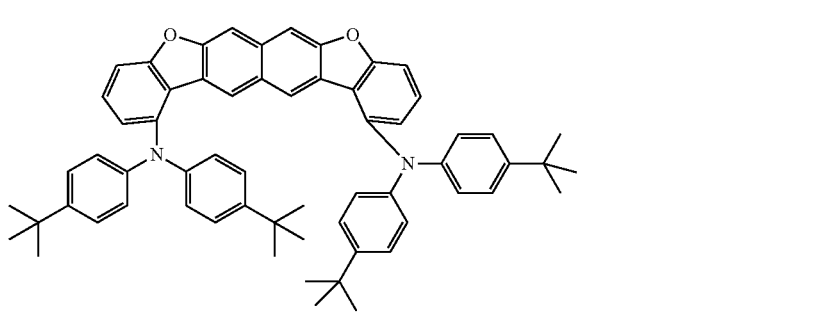

-continued
Compound 27
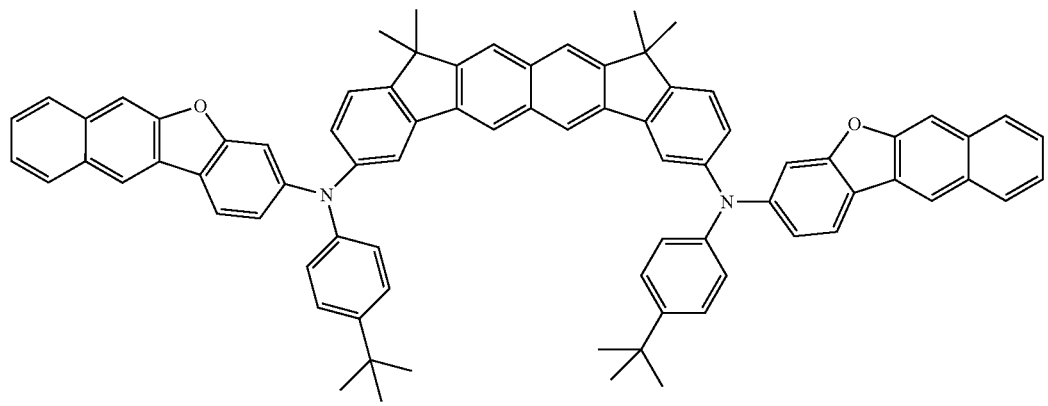
Compound 28
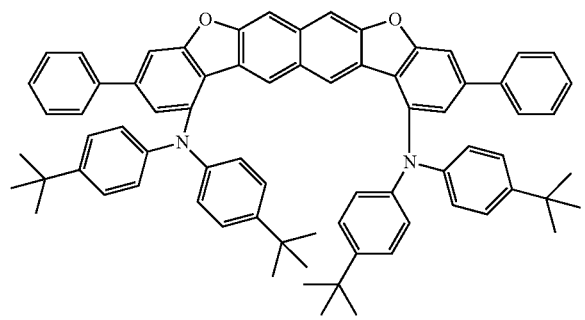
Compound 29
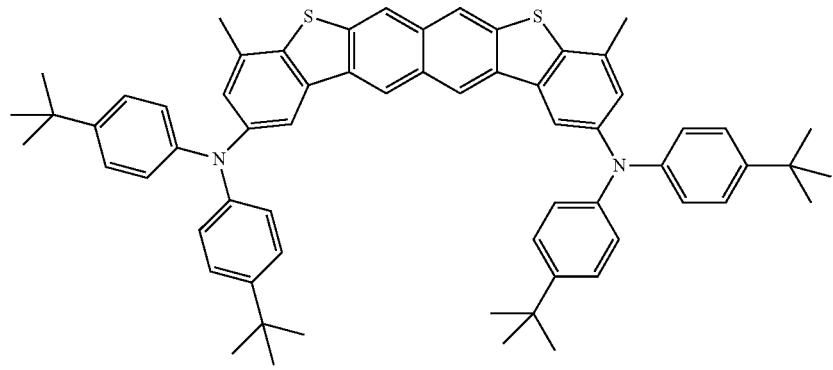
Compound 30
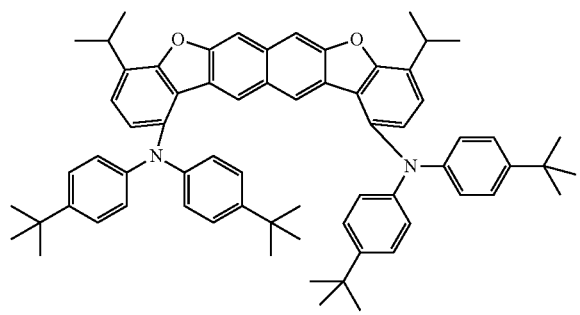

Compound 31
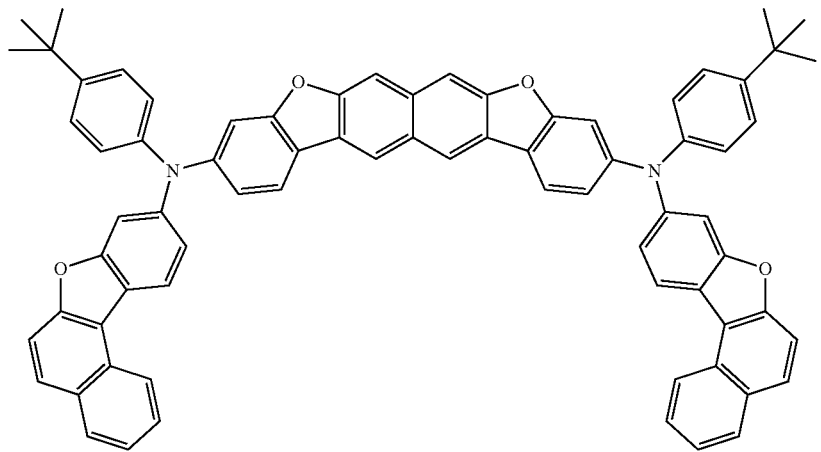
Compound 32
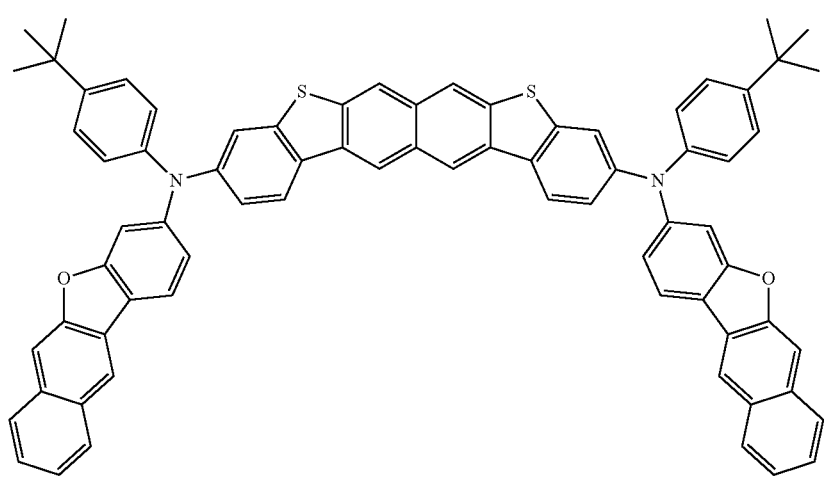
Compound 33
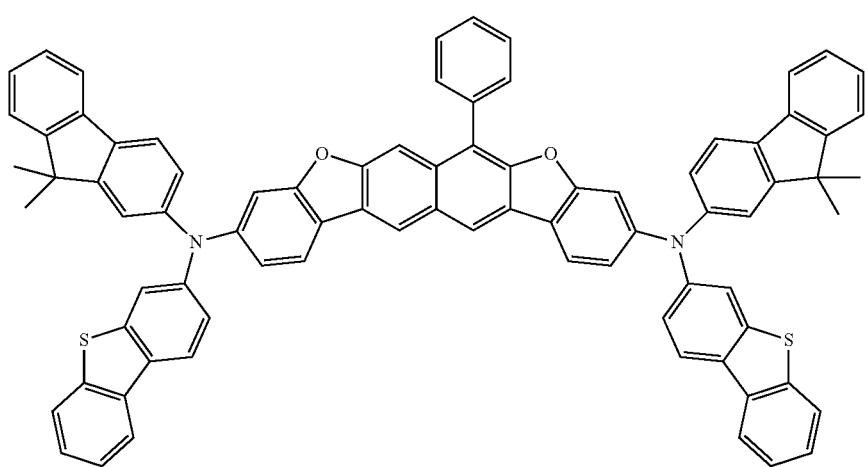

-continued
Compound 34
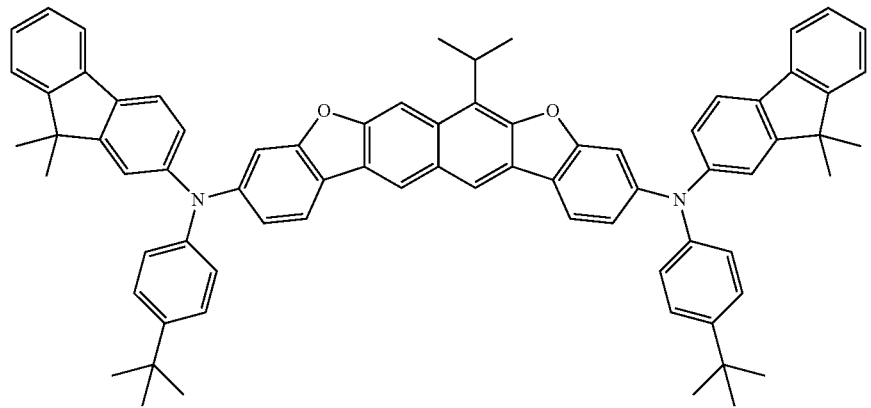
Compound 35
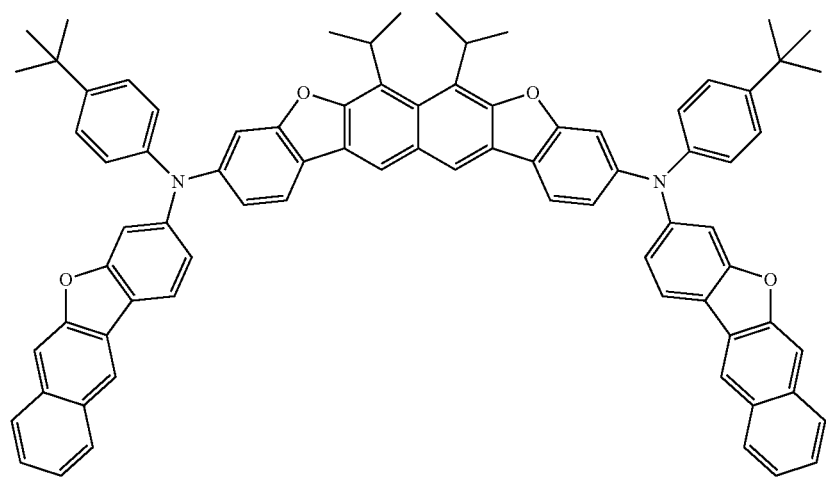
Compound 36
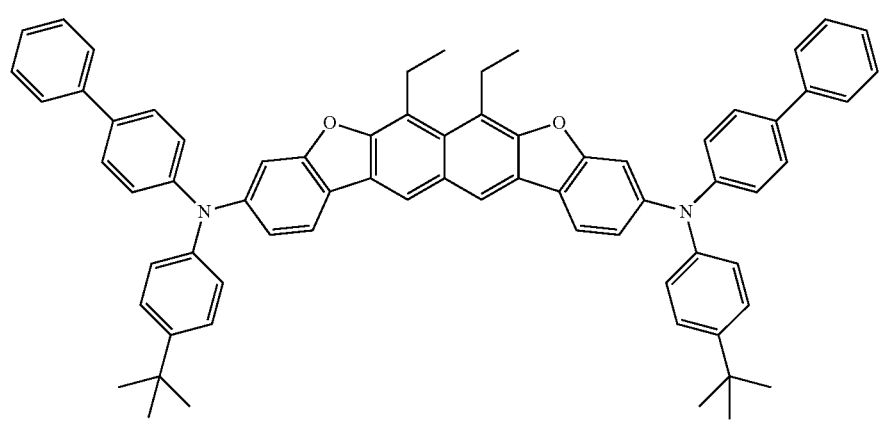

Compound 37
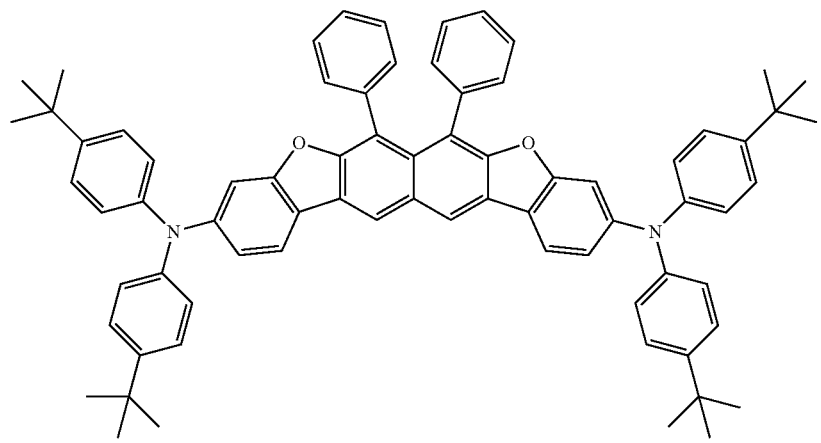
Compound 38
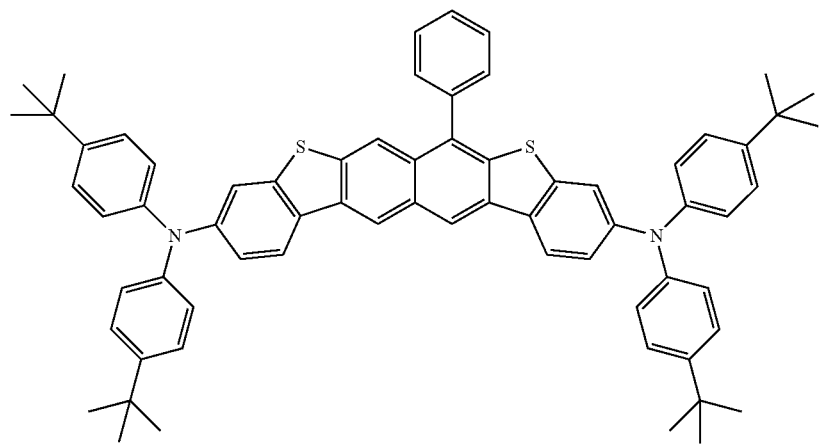
Compound 39
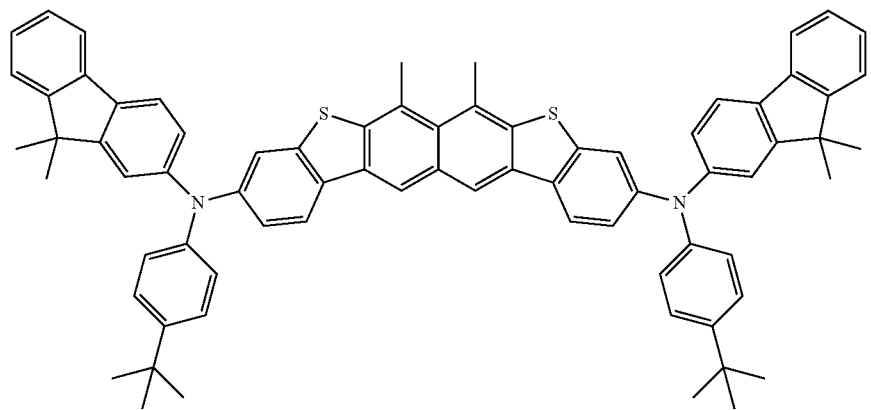
Compound 40
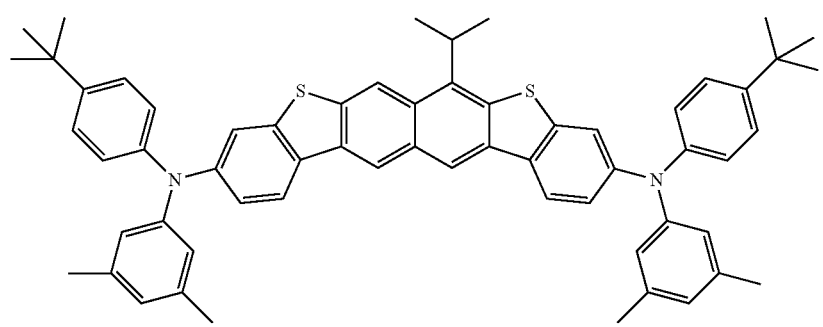

-continued
Compound 41
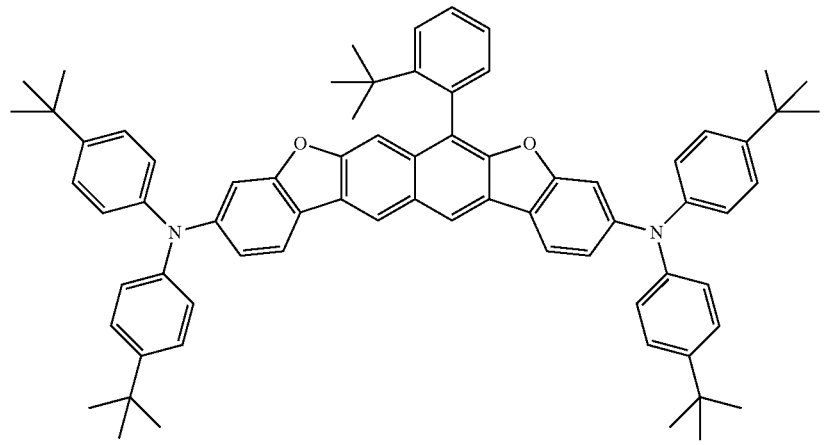
Compound 42
Compound 43

-continued
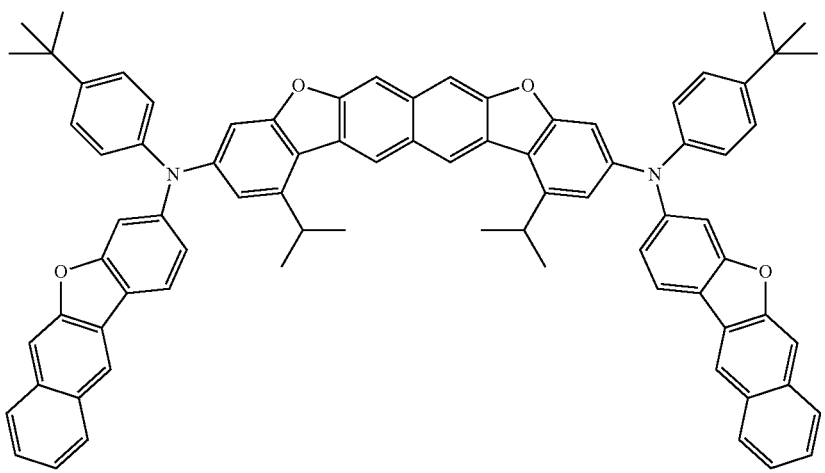
Compound 44
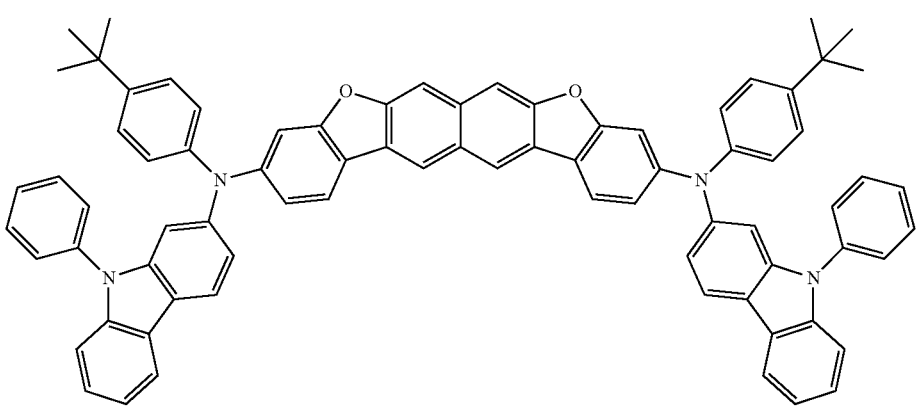
Compound 45
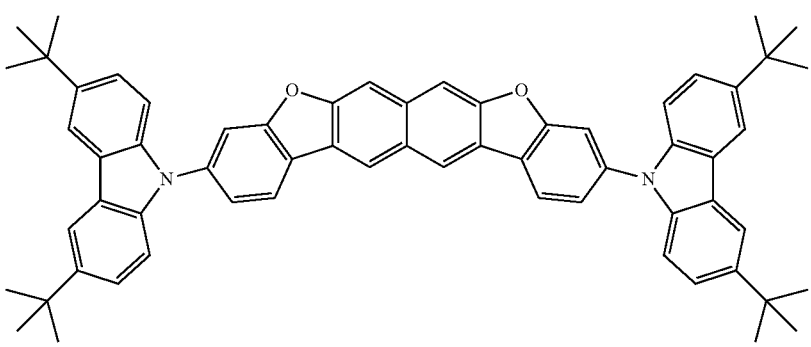
Compound 46

-continued
Compound 47
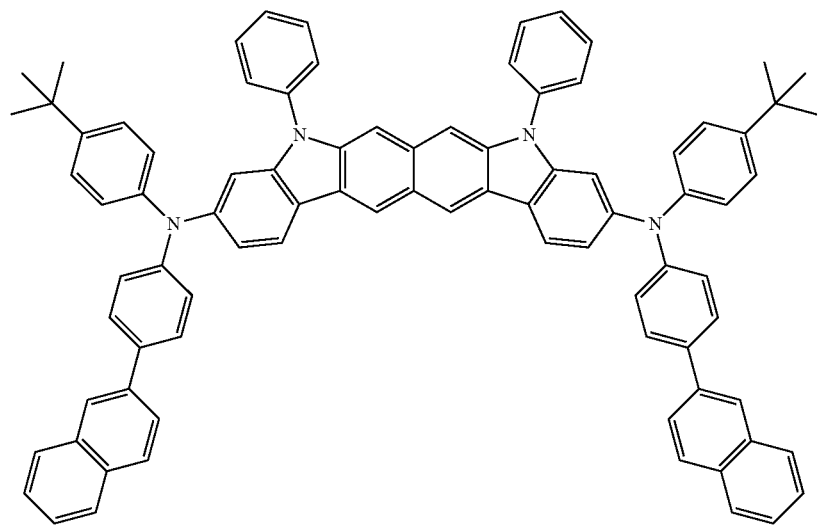
Compound 48
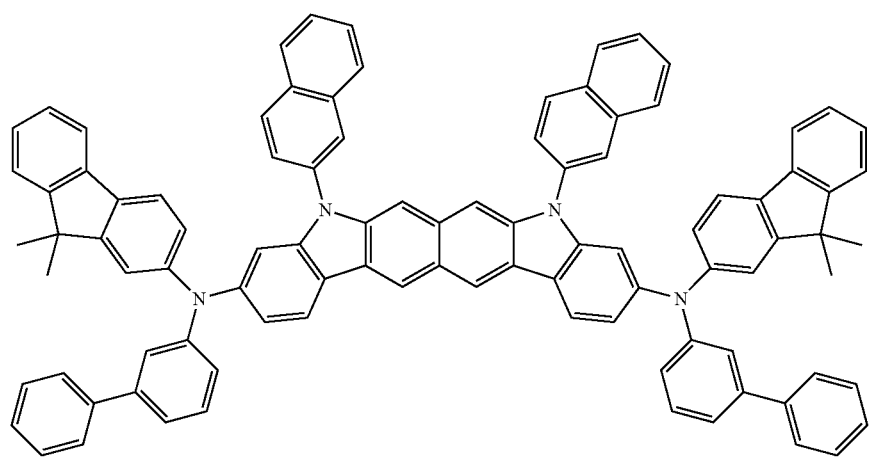
Compound 49
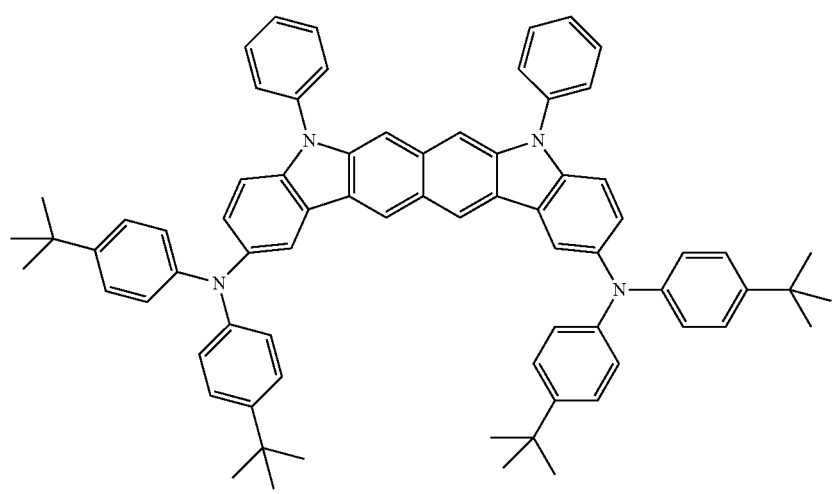

Compound 50
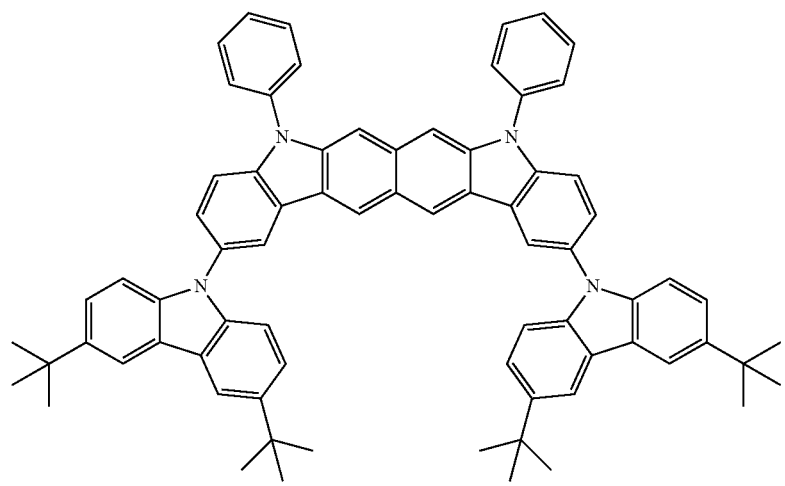
Compound 51
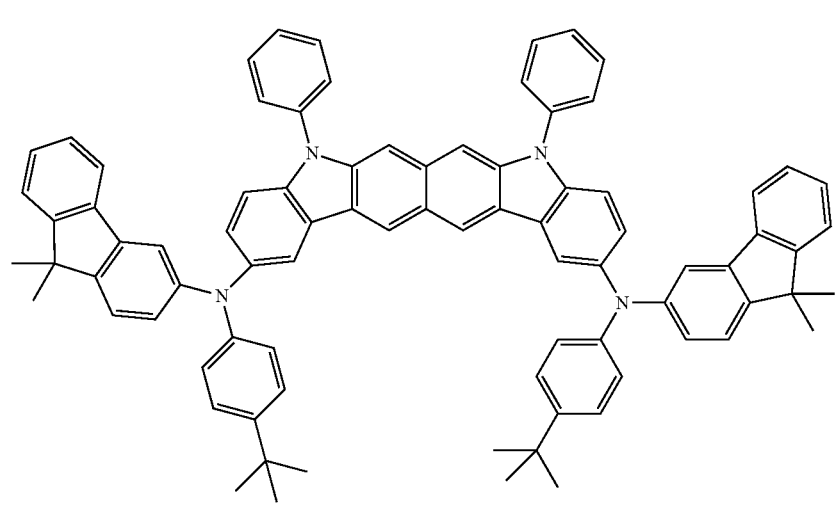
Compound 52
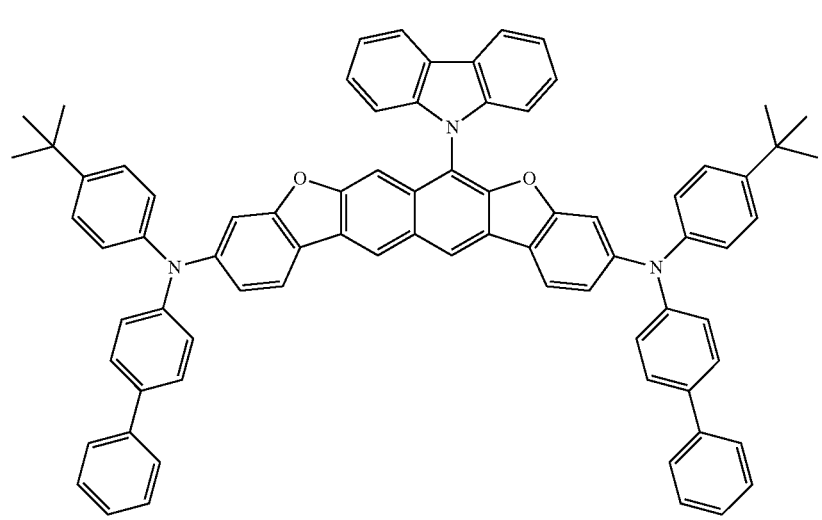

Compound 53
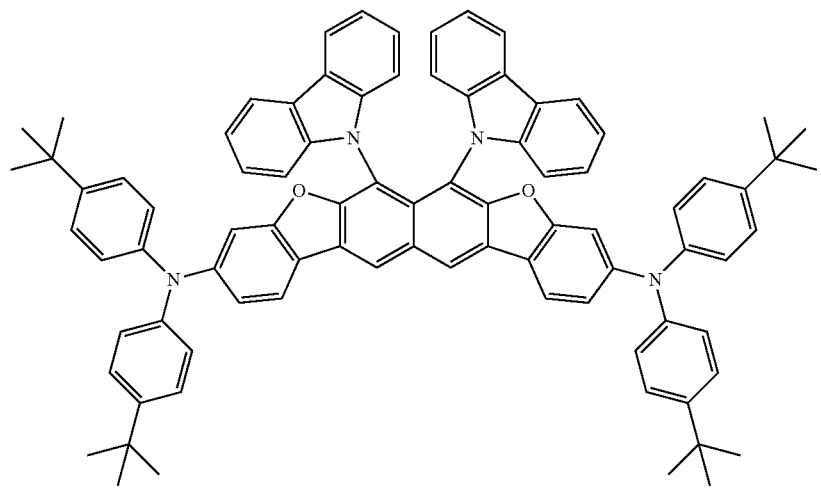
Compound 54
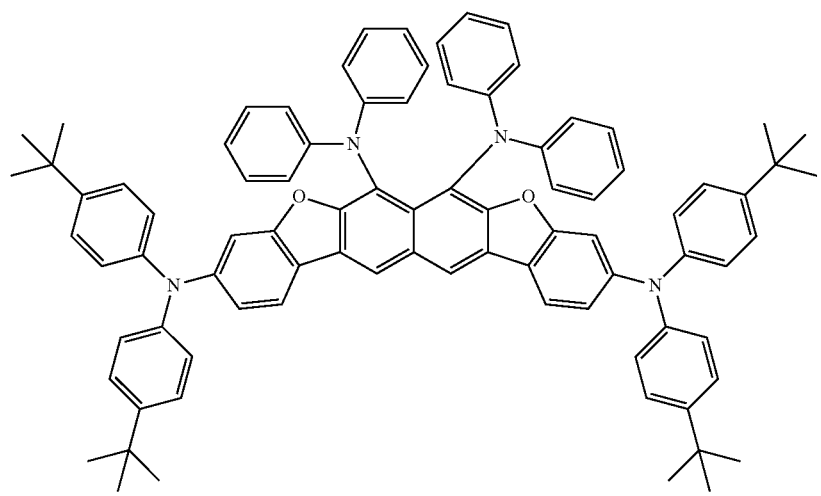
Compound 55
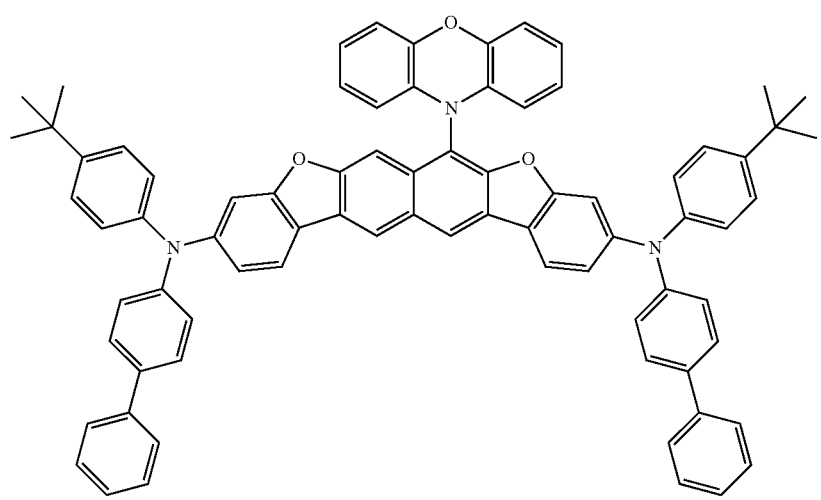

-continued
Compound 56
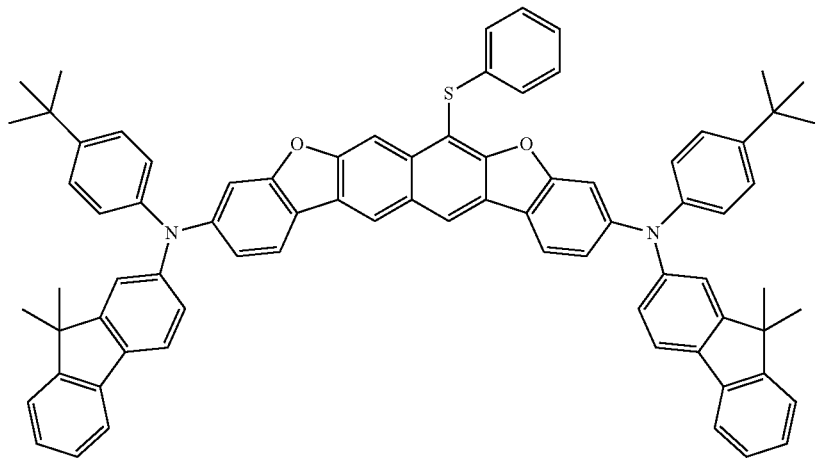
Compound 57
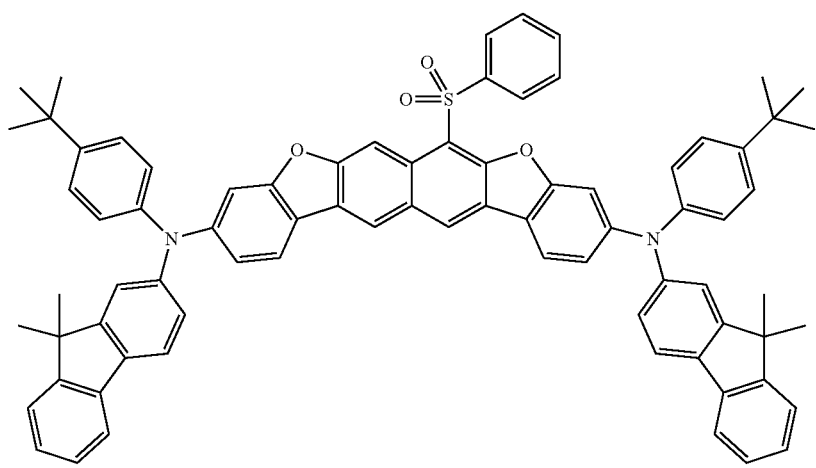
Compound 58
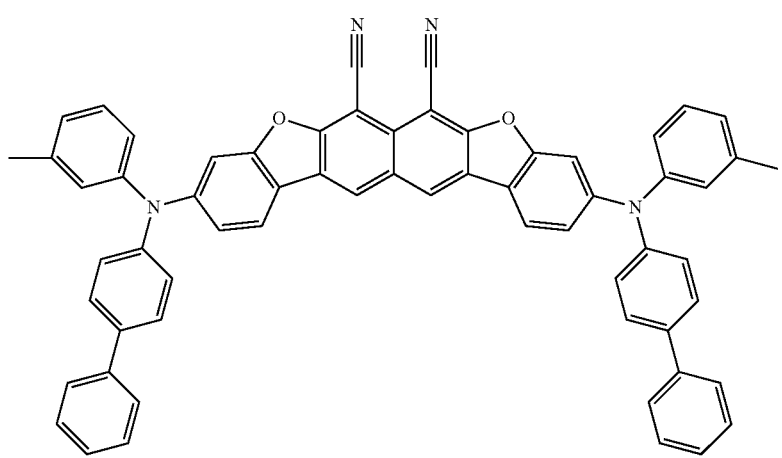

-continued
Compound 59
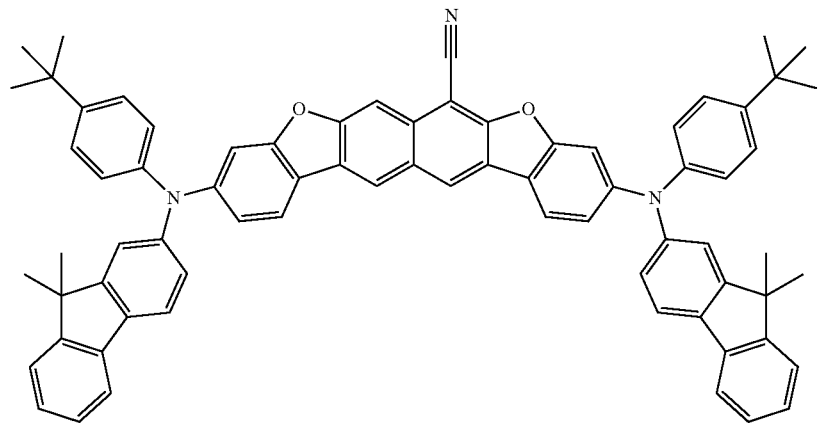
Compound 60
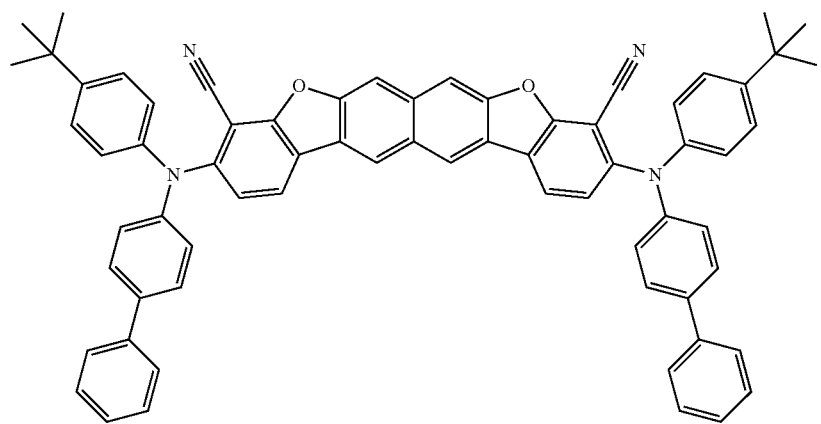
Compound 61
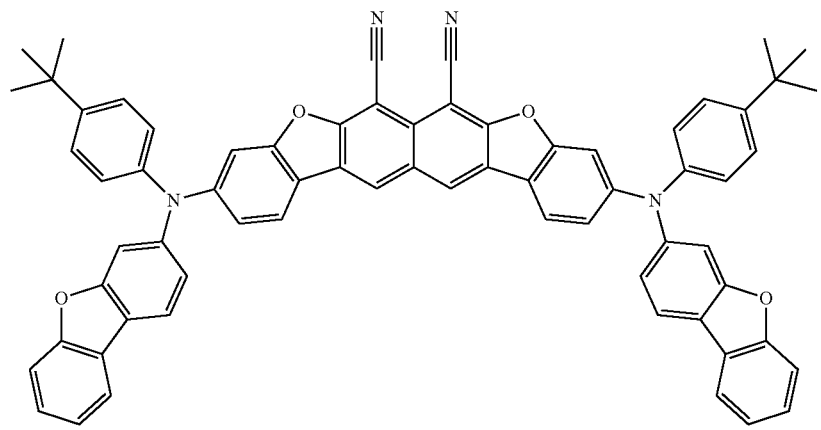
Compound 62
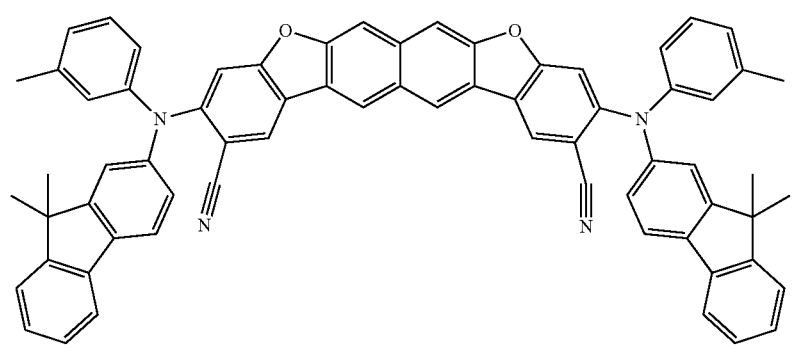

Compound 63
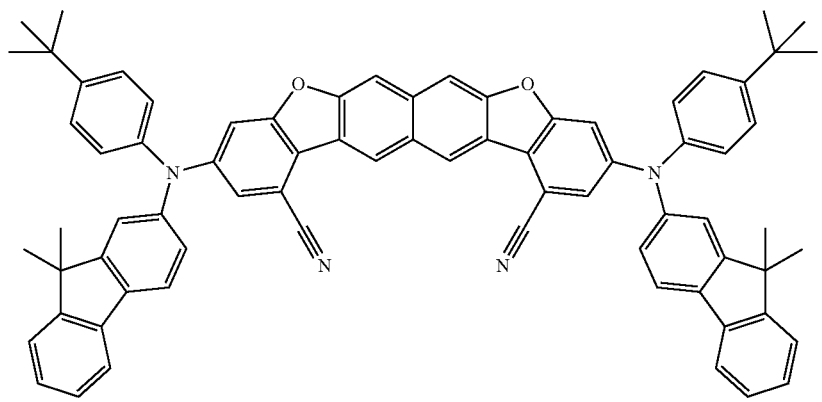
Compound 64
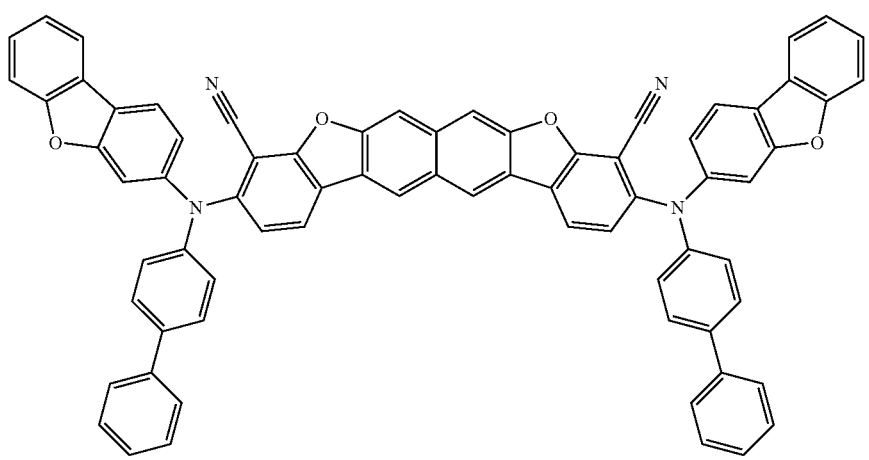
Compound 65
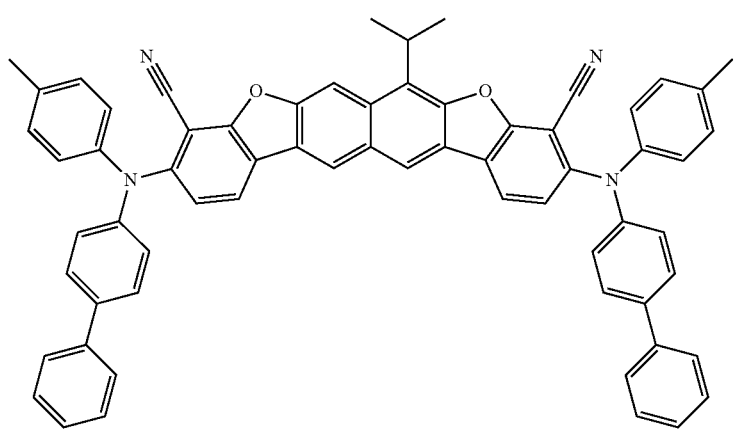

Compound 66
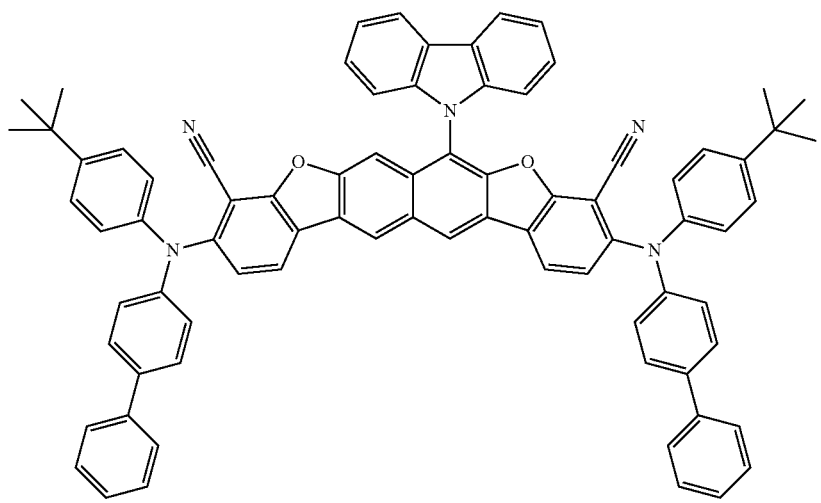
Compound 67
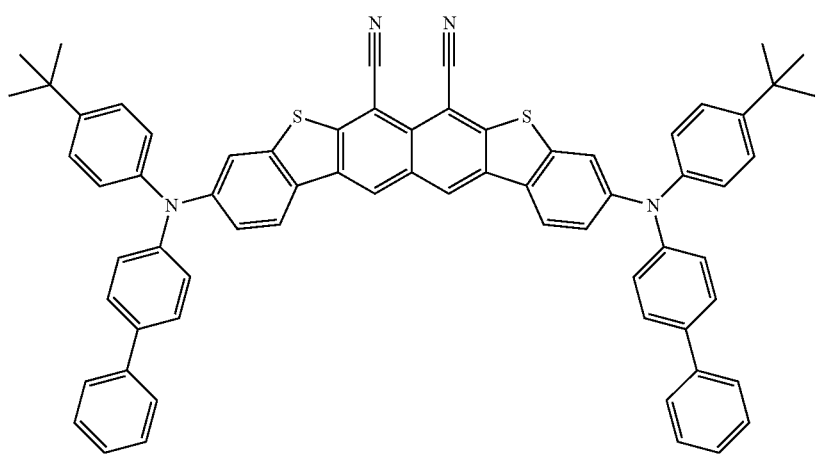
Compound 68
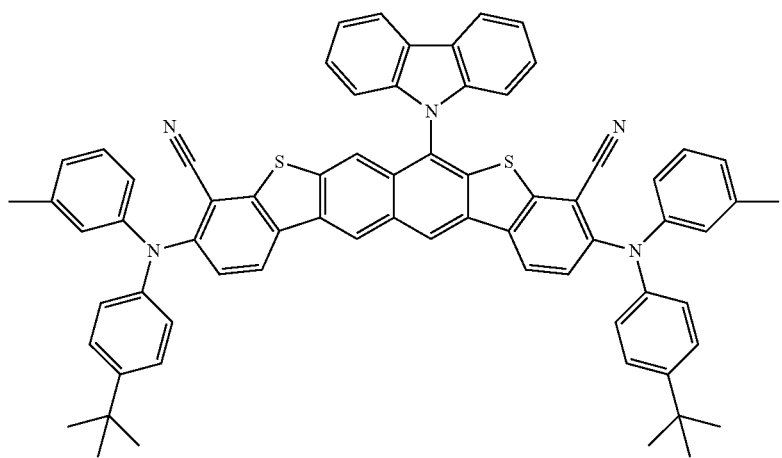

-continued
Compound 69
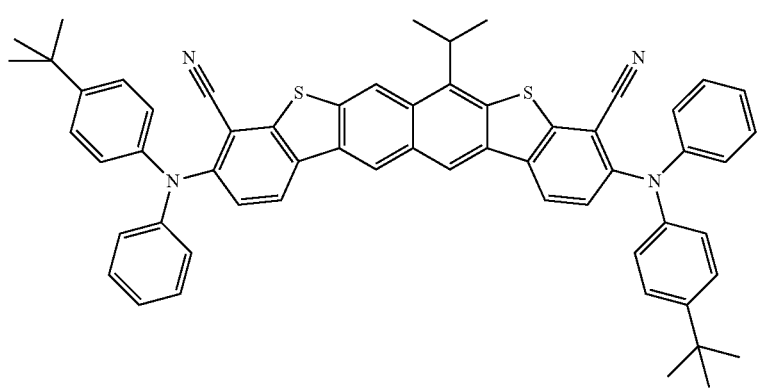
Compound 70
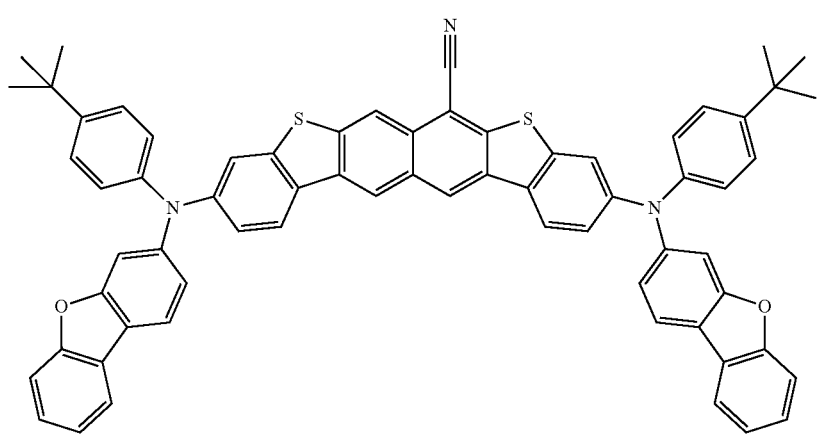
Compound 71
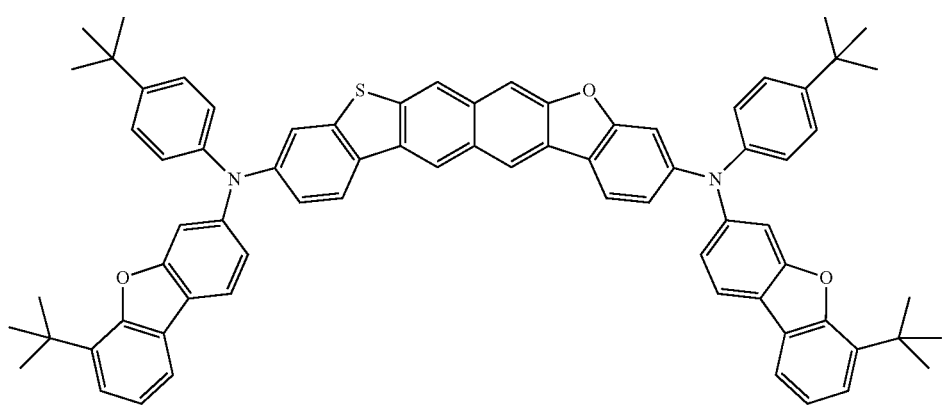
Compound 72
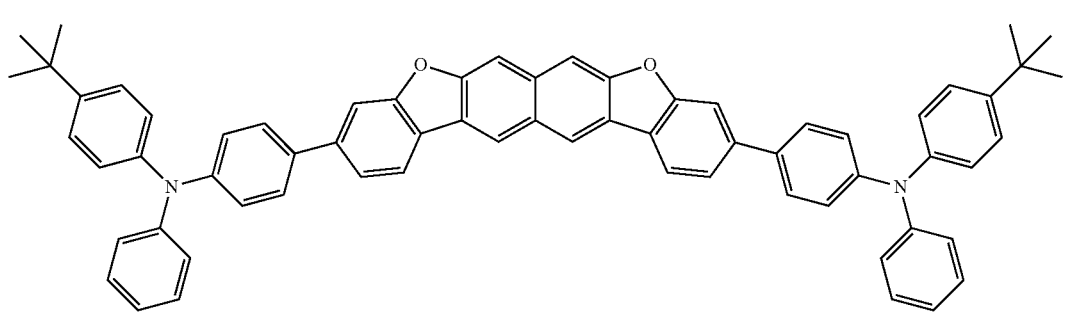
3. The organic light emitting device of claim 1, wherein the organic material layer comprises a hole injection layer or a hole transfer layer, and the hole injection layer or the hole transfer layer comprises the compound.

4. The organic light emitting device of claim 1, wherein the organic material layer comprises an electron transfer layer or an electron injection layer, and the electron transfer layer or the electron injection layer comprises the compound.

5. The organic light emitting device of claim 1, wherein the organic material layer comprises a light emitting layer, and the light emitting layer comprises the compound.

6. The organic light emitting device of claim 1, wherein the organic material layer comprises an electron blocking layer or a hole blocking layer, and the electron blocking layer or the hole blocking layer comprises the compound.

7. An organic light emitting device, comprising:
a first electrode;
a second electrode provided opposite to the first electrode; and
one or more organic material layers provided between the first electrode and the second electrode,
wherein one or more layers of the organic material layers comprise the compound of Chemical Formula 1:

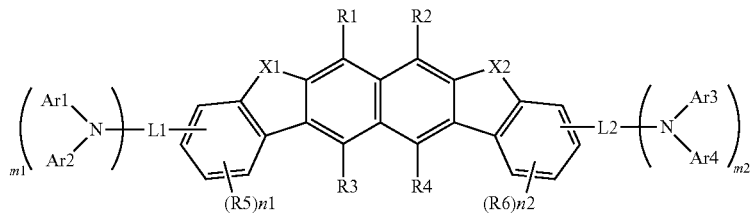

wherein, in Chemical Formula 1:
X1 and X2 are the same as or different from each other, and each independently is O, S, CRaRb or NRc;

Ra, Rb, Rc and R1 to R6 are the same as or different from each other, and each independently is hydrogen, deuterium, a halogen group, a cyano group, a sulfide group, a sulfonyl group, a substituted or unsubstituted alkyl group, a substituted or unsubstituted cycloalkyl group, a substituted or unsubstituted arylamine group, a substituted or unsubstituted aryl group, or a substituted or unsubstituted heteroaryl group;

Ar1 to Ar4 are the same as or different from each other, and each independently is a substituted or unsubstituted aryl group or a substituted or unsubstituted heteroaryl group, or adjacent groups bond to each other to form a substituted or unsubstituted ring;

L1 and L2 are the same as or different from each other, and each independently is a direct bond or a substituted or unsubstituted arylene group;

n1 and n2 are each an integer of 0 to 3, and when n1 and n2 are each 2 or greater, substituents in the parentheses are the same as or different from each other; and m1 and m2 are each an integer of 1 to 4, and m1+m2≥2 and n1+n2≤6; and wherein one of the organic material layers comprises a light emitting layer, and the light emitting layer comprises a compound of Chemical Formula 1B:

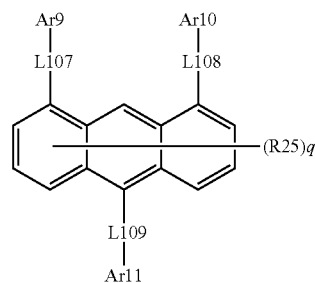

wherein in Chemical Formula 1B:
L107 to L109 are the same as or different from each other, and each independently is a direct bond, a substituted or unsubstituted arylene group, or a substituted or unsubstituted heteroarylene group;

Ar9 to Ar11 are the same as or different from each other, and each independently is a substituted or unsubstituted aryl group or a substituted or unsubstituted heteroaryl group;

R25s are the same as or different from each other, and each independently is hydrogen, deuterium, a halogen group, a nitrile group, a nitro group, a substituted or unsubstituted alkyl group, a substituted or unsubstituted cycloalkyl group, a substituted or unsubstituted silyl group, a substituted or unsubstituted phosphine oxide group, a substituted or unsubstituted aryl group, or a substituted or unsubstituted heteroaryl group;

q is an integer of 0 to 7; and
when q is 2 or greater, substituents in the parentheses are the same as or different from each other.

8. The organic light emitting device of claim 7, wherein L107 to L109 are the same as or different from each other, and each independently is a direct bond or selected from among the following structures:

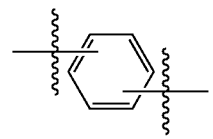

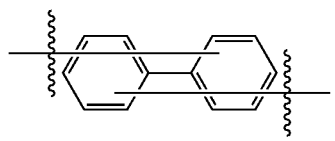

-continued
LC3
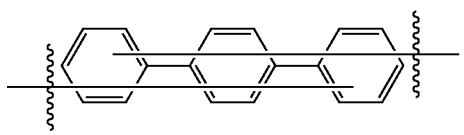
LC4
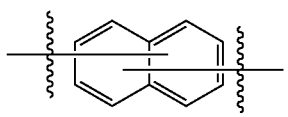
LC5
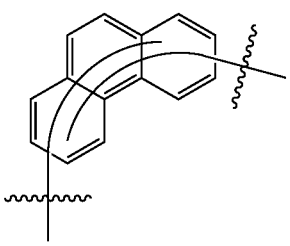
LC6
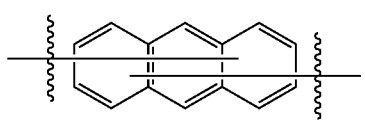
LC7
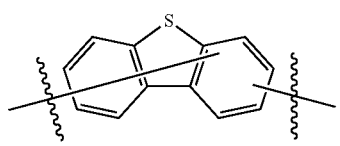
LC8
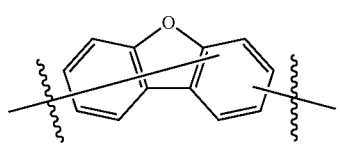
LC9
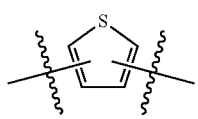
LC10
LC11
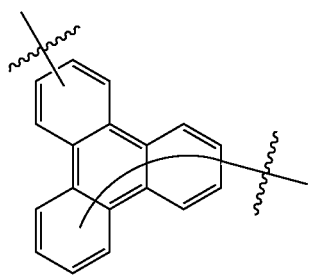
-continued
LC12
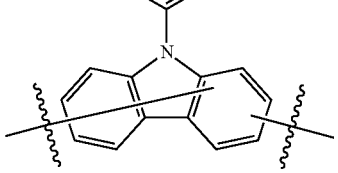
LC13
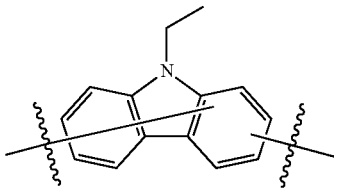
LC14
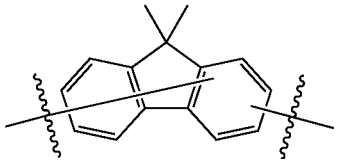
LC15
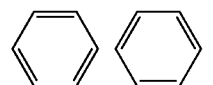
9. The organic light emitting device of claim 7, wherein Ar9 to Ar11 are the same as or different from each other, and each independently is selected from among the following structures:
RB1
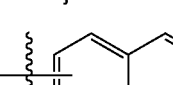
RB2
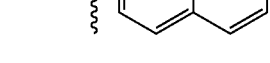
RB3
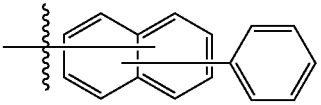
RB4